(12) United States Patent
De Jersey et al.

(10) Patent No.: US 9,200,020 B2
(45) Date of Patent: Dec. 1, 2015

(54) 6-OXOPURINE PHOSPHORIBOSYLTRANSFERASE INHIBITORS

(71) Applicants: THE UNIVERSITY OF QUEENSLAND, St. Lucia, Queensland (AU); INSTITUTE OF ORGANIC CHEMISTRY AND BIOCHEMISTRY ASCR, V.V.I., Prague (CZ)

(72) Inventors: John De Jersey, Chapel Hill (AU); Luke William Guddat, Kenmore (AU); Dana Hockova, Prague (CZ); Dianne Therese Keough, Chelmer (AU)

(73) Assignees: THE UNIVERSITY OF QUEENSLAND, St. Lucia, Queensland (AU); INSTITUTE OF ORGANIC CHEMISTRY AND BIOCHEMISTRY ASCR, V.V.I., Prague (CZ)

( * ) Notice: Subject to any disclaimer, the term of this patent is extended or adjusted under 35 U.S.C. 154(b) by 0 days.

(21) Appl. No.: 14/399,316

(22) PCT Filed: May 7, 2013

(86) PCT No.: PCT/AU2013/000467
§ 371 (c)(1),
(2) Date: Nov. 6, 2014

(87) PCT Pub. No.: WO2013/166545
PCT Pub. Date: Nov. 14, 2013

(65) Prior Publication Data
US 2015/0099722 A1   Apr. 9, 2015

Related U.S. Application Data

(60) Provisional application No. 61/643,419, filed on May 7, 2012.

(51) Int. Cl.
| | |
|---|---|
| C07D 473/18 | (2006.01) |
| A61K 31/683 | (2006.01) |
| A61K 31/675 | (2006.01) |
| C07F 9/6561 | (2006.01) |
| A61K 45/06 | (2006.01) |
| A61K 31/662 | (2006.01) |
| A61K 31/663 | (2006.01) |
| A61K 31/664 | (2006.01) |

(52) U.S. Cl.
CPC .......... *C07F 9/65616* (2013.01); *A61K 31/662* (2013.01); *A61K 31/663* (2013.01); *A61K 31/664* (2013.01); *A61K 31/675* (2013.01); *A61K 31/683* (2013.01); *A61K 45/06* (2013.01); *C07D 473/18* (2013.01)

(58) Field of Classification Search
CPC ... C07D 473/18; A61K 31/683; A61K 31/675
See application file for complete search history.

(56) References Cited

PUBLICATIONS

International Search Report for PCT/AU2013/000467 mailed May 23, 2013, three (3) pages.
Efimov et al., "Synthesis and Evaluation of Some Properties of Chimeric Oligomers Containing PNA and Phosphono-PNA Residues." *Nucleic Acids Research*, 1998, 26(2), pp. 566-575.
Keough et al., "Inhibition of Hypoxanthine-Guanine Phosphoribosyltransferase by Acyclic Nucleoside Phosphonates: A New Class of Antimalarial Therapeutics." *Journal of Medicinal Chemistry*, 2009, 52(14), pp. 4391-4399.
Hockova et al., "Synthesis of Novel N-Branched Acyclic Nucleoside Phosphonates As Potent and Selective Inhibitors of Human, Plasmodium falciparum and Plasmodium vivax 6-Oxopurine Phosphoribosyltransferases." *Journal of Medicinal Chemistry*, 2012, 55(13), pp. 6209-6223.

*Primary Examiner* — Timothy Thomas
(74) *Attorney, Agent, or Firm* — Nixon & Vanderhye P.C.

(57) ABSTRACT

The invention relates to compounds which are useful as inhibitors of 6-oxopurine phosphoribosyltransferases such as hypoxanthine-guanine-(xanthine) phosphoribosyltransferase (HG(X)PRT).

14 Claims, No Drawings

6-OXOPURINE PHOSPHORIBOSYLTRANSFERASE INHIBITORS

This application is the U.S. national phase of International Application No. PCT/AU2013/000467 filed 7 May 2013 which designated the U.S. and the claims benefit of U.S. Provisional Application No. 61/643,419 filed 7 May 2012, the entire contents of each of which are hereby incorporated by reference.

FIELD OF THE INVENTION

The invention relates to compounds which are useful as inhibitors of 6-oxopurine phosphoribosyltransferases such as hypoxanthine-guanine-(xanthine) phosphoribosyltransferase (HG(X)PRT). Inhibitors of these enzymes may be used in the prevention or treatment of microbial infections, including infections caused by protozoal and bacterial species. The compounds of the invention are particularly suited to the prevention or treatment of infections caused by *Plasmodium* spp. which are responsible for malaria.

BACKGROUND OF THE INVENTION

The 6-oxopurine phosphoribosyltransferases (PRTases) (EC:2.4.2.8 HG(X)PRT and/or XGPRT EC:2.4.22) are necessary for both survival and reproduction of many microorganisms (including protozoa and certain bacteria) because, unlike mammalian cells, such microorganisms are auxotrophic for the purine ring. Thus, these microorganisms depend on these enzymes for the synthesis of the 6-oxopurine nucleoside monophosphates required for RNA/DNA production. On the other hand, humans possess two metabolic pathways to synthesise nucleoside monophosphates: de novo and salvage. Partial inhibition of the human enzyme should not have any serious side-effects. This is based on the fact that humans with an inherited genetic defect which results in only 3% of normal activity of this enzyme lead normal lives.

Accordingly the 6-oxopurine PRTases represent a target with therapeutic potential. The reactions catalysed by these enzymes are shown in Scheme 1.

Scheme 1. The reaction catalysed by HG(X)PRT.

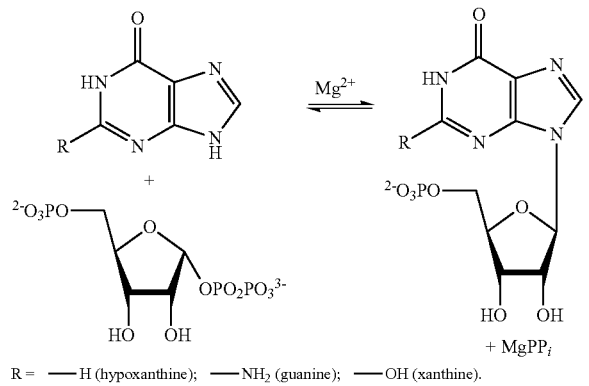

R = —H (hypoxanthine); —NH$_2$ (guanine); —OH (xanthine).

6-Oxopurine phosphoribosyltransferase is the generic name for enzymes which add a phosphoribosyl group from PRib-PP onto the N9 atom of a 6-oxopurine to form a nucleoside monophosphate. The 6-oxopurine PRTases found in nature vary in their specificities for the three naturally occurring 6-oxopurines, hypoxanthine, guanine and xanthine. The specific names given to 6-oxopurine PRTases denote this specificity. For example, the human enzyme is called hypoxanthine guanine PRTase (abbrev. HGPRT) because it can efficiently use both hypoxanthine and guanine as substrates. The *Plasmodium falciparum* enzyme is called HGXPRT because it can use xanthine in addition to hypoxanthine and guanine as substrates.

Some organisms (including human, other mammals and *Plasmodium* species) encode and synthesize only one 6-oxopurine PRTase. Other organisms encode and synthesize two 6-oxopurine PRTases. Of these enzymes, the best characterized are *Escherichia coli* XGPRT and HPRT (Guddat, L. W., S., Martin, J. L., Keough, D. T. and de Jersey, J. (2002) Crystal structures of free, IMP-, and GMP-bound *Escherichia coli* hypoxanthine phosphoribosyltransferase. *Protein Sci.* 11: 1626-1638). As the abbreviations indicate, the former enzyme prefers guanine and xanthine while the latter prefers hypoxanthine.

The 6-oxopurine PRTases are members of purine salvage pathways present in all or virtually all species. These pathways contain a variety of enzymes. Their function is to make all of the required purine nucleotides (for RNA and DNA synthesis and for other purposes) using preformed purines.

Many organisms (including humans and many microorganisms) can produce purine bases from simple precursor molecules by the pathway known as de novo synthesis. Organisms which lack the de novo pathway and depend absolutely on the activity of one 6-oxopurine PRTase for the synthesis of purine nucleotides and which are human or animal pathogens are therefore the prime targets for 6-oxopurine PRTase inhibitors. Such organisms include several protozoan parasites including the *Plasmodium* species responsible for human malaria and *Helicobacter pylori* the causative organisms of gastric ulcers. For bacterial strains, especially those resistant to current antibiotics, inhibitors of the 6-oxopurine PRTases are potential leads for the development of novel antibiotics. It is also proposed that combination therapy which includes the co-administration with inhibitors of the de novo pathway (such as azaserine) will be a successful therapy.

Acyclic nucleoside phosphonates (ANPs) are reverse transcriptase inhibitors and several ANP-based drugs are in current clinical use for the treatment of serious viral infections (e.g. Viread®, Vistide®, Hepsera®). These compounds consist of a nucleobase, either 6-aminopurine or pyrimidine, linked to a phosphonate group by an acyclic linker. 2-(Phosphonoethoxy)ethyl guanine (PEEG) and 2-(phosphonoethoxy)ethyl hypoxanthine (PEEHx) are good inhibitors of both human HGPRT and *Plasmodium falciparum* HGXPRT (PfHGXPRT):

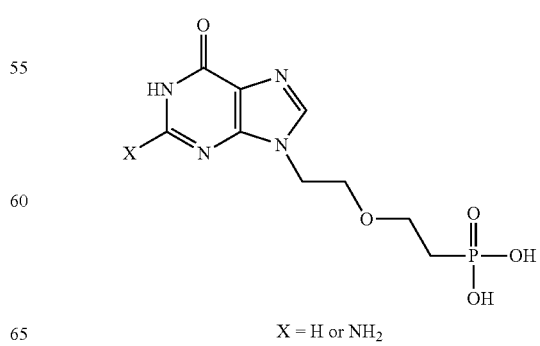

X = H or NH$_2$

PEEG and PEEHx have $K_i$ values for human HGPRT of 1 μM and 3.6 μM respectively, and 0.1 μM and 0.3 μM for PfHGXPRT. ANPs are believed to be metabolically stable due to the presence of a phosphonate P—C linkage instead of a P—O phosphoester, making them resistant towards phosphomonoesterases and nucleotidases. ANPs are also believed to be stable because the bond between the purine and the linker is stable, in contrast to the bond between the purine and the ribose in purine nucleotides.

There are four major species of Plasmodium that infect humans and result in symptoms of malaria: *falciparum, vivax, malariae* and *ovale. Plasmodium falciparum* (pf) and *Plasmodium vivax* (Pv) are the most lethal and widespread with both species infecting around 500 million people per year, resulting in at least 1 million deaths per annum, mainly children. Drugs such as artemisinin and combination therapies, quinine, chloroquine, primaquine, are the only known treatments for malaria but, because of increasing resistance to these drugs as well as cost-effectiveness, there is an urgent need for the discovery of new targets and therapeutic leads for the development of potent anti-malarials. Likewise, there is an ongoing need for new agents that are effective against a range of other pathogenic microorganisms.

SUMMARY OF THE INVENTION

It has now been found that a new series of ANPs are potent inhibitors of 6-oxopurine phosphoribosyltransferases such as hypoxanthine-guanine-(xanthine) phosphoribosyltransferase (HG(X)PRT). The new series differs most significantly from other ANPs in that they comprise a nitrogen atom which replaces the oxygen atom in the acyclic portion of the molecule. Without wishing to be bound by theory this nitrogen atom provides a branching point in the acyclic portion of the molecule such that the molecule may bind at three closely spaced subsites of the target. This increases the binding potential which leads to a significant improvement in the affinity and/or selectivity for 6-oxopurine phosphoribosyltransferases such as hypoxanthine-guanine-(xanthine) phosphoribosyltransferase (HG(X)PRT). Additionally, the nitrogen atom enables groups to be appended in a modular fashion, enabling the construction of a diverse range of molecular architectures with a diverse range of chemical groups, using a range of readily accessible synthetic techniques. Furthermore, the aza-compounds of the invention substantially avoid problems associated with resolving the stereoisomers of the carbo-analogs of the compounds of the invention.

Accordingly in one aspect the present invention provides a compound of formula:

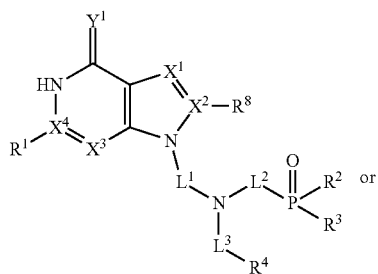

or

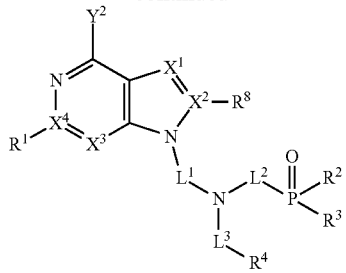

wherein:
$L^1$ and $L^2$ are each independently selected from $C_{1-4}$alkylene, $C_{2-4}$alkenylene and $C_{2-4}$alkynylene wherein $L^1$ and/or $L^2$ are each independently optionally substituted with one or more $C_{1-4}$alkyl, $C_{2-4}$alkenyl or $C_{2-4}$alkynyl;
$L^3$ is selected from $C_{1-7}$alkylene, $C_{2-7}$alkenylene and $C_{2-7}$alkynylene wherein $L^3$ is optionally substituted with one or more groups selected from OH, $C_{1-4}$alkyl, $C_{2-4}$alkenyl or $C_{2-4}$alkynyl;
$R^1$ is alkyl, aryl, heteroaryl, alkenyl, alkynyl, arylalkyl heteroarylalkyl, $NR^7_2$, halogen, $OR^7$, H or $NH_2$;
$R^2$ and $R^3$ are independently selected from OH, $OR^7$, $SR^7$, $NHR^7$, $NR^7_2$, and $R^p$;
$R^4$ is $NH_2$, NHOH, $N_3$, $NHR^7$, $NR^7_2$, $C(O)NHR^7$. $C(O)NR^7_2$, SH, $SR^7$, CHO, alkyl, alkenyl, alkynyl, aryl, heteroaryl, cycloalkyl, heterocycloalkyl optionally substituted with one or, more OH and/or $CH_2OH$, $C(O)R^7$, $OR^7$, $COOR^7$, CN, COOH, OH, $P(O)R^5R^6$ or —O— $C_{1-2}$alkylene-$P(O)R^5R^6$;
$R^5$ and $R^6$ are independently selected from OH, $OR^7$, $SR^7$, $NHR^7$, $NR^7_2$, and $R^p$;
$R^8$ is selected from H, alkyl, aryl, heteroaryl, $NR^7_2$, halogen, $OR^7$;
wherein $R^p$ is a prodrug substituent and wherein the or each $R^7$, where present, is independently selected from alkyl, alkenyl, alkynyl, aryl, acyl and arylalkyl optionally containing one or more heteroatoms;
$X^1$ is selected from N or CH;
$X^2$ is C or $X^2$—$R^8$ forms N;
$X^3$ is selected from N or CH;
$X^4$ is C or $X^4$—$R^1$ forms N;
$Y^1$ where present is selected from S and O, and $Y^2$ where present is selected from halogen;
wherein the combined number of non-hydrogen atoms in $L^1$ and $L^2$ excluding the number of atoms in the optional substituent(s), where present, is between 3 and 5; and
wherein the combined number of non-hydrogen atoms in $L^3$ and $R^4$ excluding the number of atoms in the optional substituent(s), where present, and excluding the number of atoms in $R^5$ and $R^6$ is less than or equal to 8,
or a pharmaceutically acceptable salt thereof.

$R^p$ is a prodrug substituent. As used herein the term prodrug refers to a masked form of a compound of the invention such that drug absorption and/or drug delivery into the target organism is typically enhanced. For example, the highly polar phosphonate group (wherein $R^2$ and $R^3$ are OH) may be masked with a more lipophilic group to enhance transport across cell membranes. The prodrug may be unmasked by cellular enzymes (including lipases, esterases, reductases, oxidases, nucleases or amidases) or by chemical cleavage such as hydrolysis to release the compound of the invention after the prodrug has entered a cell in the target of interest.

It has been found that the prodrugs of the compounds of the invention may provide certain advantages over the correspondingly unmasked compounds of the invention, such as improved levels of uptake into the microorganism (prodrugs are not inhibitors of the enzymes activity or are weakly inhibitory). Examples of substituents which may be used to form prodrugs according to the invention include those substituents that may be cleaved in vivo to provide the compound of the invention with a phosphonate residue. For example, a phosphoramidate moiety formed by condensing the amine group of an amino acid with a phosphonate (or activated form thereof) may undergo hydrolysis in vivo to reform the phosphonate group. Accordingly, in some embodiments $R^p$ may be an amino acid residue (including an ester derivative of an amino acid residue) or $R^p$ may be an optionally substituted alkoxy group.

In one aspect the invention provides the use of a compound of the invention, or a pharmaceutically acceptable salt thereof, in the inhibition of a 6-oxopurine phosphoribosyltransferase enzyme such as hypoxanthine-guanine-(xanthine) phosphoribosyltransferase (HG(X)PRT).

The compounds of the invention are particularly well suited to preventing or treating infections caused by those organisms that are auxotrophic for the purine ring present in nucleosides, and thus rely, or substantially rely, on the salvage pathway to provide the purine moiety for reproduction. In some embodiments such microorganisms possess no de novo, or substantially no de novo, pathway for purine synthesis.

In one aspect the invention provides the use of a compound of the invention, or a pharmaceutically acceptable salt thereof, in the preparation of a medicament for the prevention or treatment of a microbial infection. In another aspect, the invention provides a method of preventing or treating a microbial infection comprising administering a therapeutically effective amount of a compound of the invention, or a pharmaceutically acceptable salt thereof, to a subject in need thereof. In a still further aspect the invention provides a compound according to the invention, or a pharmaceutically acceptable salt thereof, for use in the prevention or treatment of a microbial infection.

In yet a further aspect the invention provides a pharmaceutical composition comprising a therapeutically effective amount of a compound of the invention, or a pharmaceutically acceptable salt thereof, together with at least one pharmaceutically acceptable carrier or diluent. The invention also provides a combination comprising a therapeutically effective amount of a compound of the invention, or a pharmaceutically acceptable salt thereof, together with at least one other therapeutic agent.

In some embodiments, the compounds of the invention are selective inhibitors for PfHGXPRT and/or PvHGPRT over human HGPRT.

DETAILED DESCRIPTION OF THE INVENTION

Prodrugs substituents include, but are not limited to: proteins; antibiotics (and antibiotic fragments); amino acids (D- and/or L-) including derivatives thereof (such as esters and amides), attached to the —P(O)— moiety in the compounds of the invention via a nitrogen atom or an oxygen atom; peptides (up to 10 amino acids) attached to the —P(O)— moiety in the compounds of the invention via a nitrogen atom or an oxygen atom; drug moieties attached to the —P(O)— moiety in the compounds of the invention via a nitrogen atom or an oxygen atom; steroids; cholesterols; folic acids; vitamins; polyamines; carbohydrates; polyethylene glycols (PEGs); cyclosaligenyls; substituted 4 to 8-membered rings, with or without heteroatom substitutions, with 1,3-phosphodiester, 1,3-phosphoramidate/phosphoester or 1,3-phosphoramidate attachments; acylthioethoxy, (SATE) $RCOSCH_2CH_2O$—; $RCOSCH_2CH_2O$—W—O—; $RCOSCH_2CH_2O$—W—S—; $RCOSCH_2CH_2O$—W—NH—; acyloxymethoxy, $RCOOCH_2O$—; $RCOOCH_2O$—W—O—; $RCOOCH_2O$—W—S—; $RCOOCH_2O$—W—NH—; alkoxycarbonyloxymethoxy, $ROCOOCH_2O$—; $ROCOOCH_2O$—W—O—; $ROCOOCH_2O$—W—S—; $ROCOOCH_2O$—W—NH—; acylthioethyldithioethoxy (DTE) $RCOSCH_2CH_2SSCH_2CH_2O$—; $RCOSCH_2CH_2SSCH_2CH_2O$—W—O—; $RCOSCH_2CH_2SSCH_2CH_2O$—W—S—; $RCOSCH_2CH_2SSCH_2CH_2O$—W—NH—; acyloxymethylphenylmethoxy (PAOB) $RCO_2$—$C_6H_4$—$CH_2$—O—; $RCO_2$—$C_6H_4$—$CH_2$—O—W—O—; $RCO_2$—$C_6H_4$—$CH_2$—O—W—S—; $RCO_2$—$C_6H_4$—$CH_2$—O—W—NH—; $RCO_2$—; 1,2-O-diacyl-glyceryloxy, $RCOO$—$CH_2$—CH(OCOR)—$CH_2O$—; 1,2-O-dialkyl-glyceryloxy, RO—$CH_2$—CH(OR)—$CH_2O$—; 1,2-S-dialkyl-glyceryloxy, RS—$CH_2$—CH(SR)—$CH_2O$—; 1-O-alkyl-2-O-acyl-glyceryloxy, RO—$CH_2$—CH(OCOR)—$CH_2O$—; 1-S-alkyl-2-O-acyl-glyceryloxy, RS—$CH_2$—CH(OCOR)—$CH_2O$—; 1-O-acyl-2-O-alky-glyceryloxy, RCOO—$CH_2$—CH(OR)—$CH_2O$—; 1-O-acyl-2-S-alkyl-glyceryloxy, RCOO—$CH_2$—CH(SR)—$CH_2O$—; any substituent attached via a nitrogen or oxygen atom to the compound of the invention that liberates the phosphonate in vivo, wherein W is selected from alkyl, aryl, arylalkyl or a heterocycle and R is selected from alkyl, alkenyl, alkynyl, aryl, acyl and arylalkyl optionally containing one or more heteroatoms and Y is selected from F, Cl, Br, alkyl, alkenyl, and alkynyl optionally containing one or more heteroatoms.

Preferably the prodrug is a group attached to the —P(O)— moiety in the compounds of the invention via a nitrogen atom or an oxygen atom. Prodrug substituents can include a residue of an amino acid, including derivatives thereof (such as esters and amides). Especially preferred prodrugs of the compounds of the invention are phosphoramidates formed from an alkyl ester of phenylalanine attached via a nitrogen atom to the —P(O)— moiety (such as the isopropyl or ethyl ester of phenylalanine, particularly (L)-phenylalanine) and phosphoesters formed from an alkyl group such as $RCOSCH_2CH_2O$— (eg SATE), lipophilic esters (eg Hostetler esters) and pivaloyloxymethyl esters (POM).

In a further aspect the present invention provides a compound of formula:

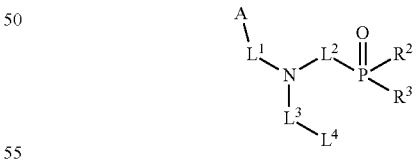

wherein A is selected from one of the following:

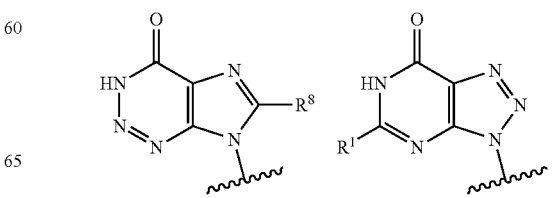

-continued

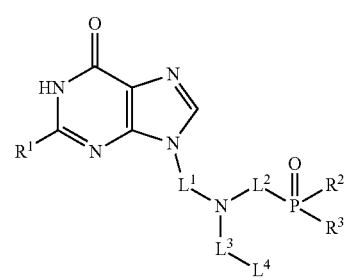

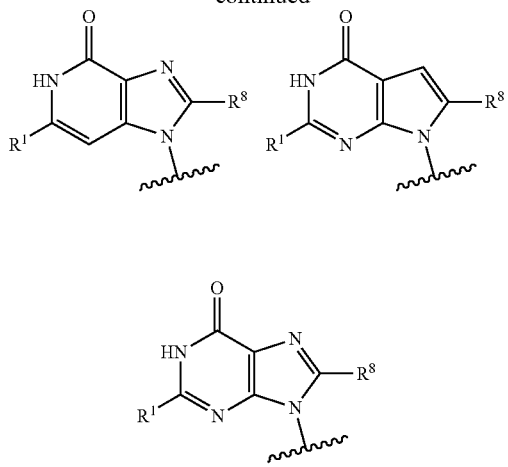

and wherein:

L¹ and L² are each independently selected from $C_{1-4}$alkylene, $C_{2-4}$alkenylene and $C_{2-4}$alkynylene wherein L¹ and/or L² are each independently optionally substituted with one or more $C_{1-4}$alkyl;

L³ is selected from $C_{1-7}$alkylene, $C_{2-7}$alkenylene and $C_{2-7}$alkynylene wherein L³ is optionally substituted with one or more groups selected from OH and C)$_{\_4}$alkyl;

R¹ where present is alkyl, aryl, heteroaryl, alkenyl, alkynyl, arylalkyl, heteroarylalkyl, $NR^7_2$, halogen, $OR^7$, H or $NH_2$;

R² and R³ are independently selected from OH, $OR^7$, $SR^7$, $NHR^7$, $NR^7_2$, and $R^p$;

R⁴ is $NH_2$, NHOH, $N_3$, $NHR^7$, $NR^7_2$, $C(O)NHR^7$, $C(O)NR^7_2$, SH, $SR^7$, CHO, alkyl, alkenyl, alkynyl, aryl, heteroaryl, cycloalkyl, heterocycloalkyl optionally substituted with one or more OH and/or $CH_2OH$, $C(O)R^7$, $OR^7$, $COOR^7$, CN. COOH, OH, $P(O)R^5R^6$ or —O—$C_{1-2}$alkylene-P(O) $R^5R^6$;

R⁵ and R⁶ are independently selected from OH, $OR^7$, $SR^7$, $NHR^7$, $NR^7_2$, and $R^p$;

R⁸ is selected from fl, alkyl, aryl, heteroaryl, $NR^7_2$, halogen, $OR^7$;

wherein $R^p$ is a prodrug substituent and wherein the or each R⁷, where present, is independently selected from alkyl, alkenyl, alkynyl, aryl, acyl and arylalkyl optionally containing one or more heteroatoms;

X¹ is selected from N or CH;

X² is C or X²—R⁸ forms N;

X³ is selected from N or CH;

X⁴ is C or X⁴—R¹ forms N;

wherein the combined number of non-hydrogen atoms in L¹ and L² excluding the number of atoms in the optional substituent(s), where present, is between 3 and 5; and wherein the combined number of non-hydrogen atoms in L³ and R⁴ excluding the number of atoms in the optional substituent(s), where present, and excluding the number of atoms in R⁵ and R⁶ is less than or equal to 8, or a pharmaceutically acceptable salt thereof.

In another aspect the invention provides a compound of formula:

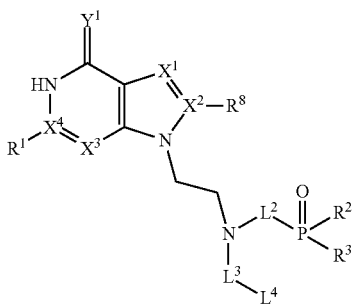

wherein:

L¹ and L² are each independently selected from $C_{1-4}$alkylene optionally substituted with one or more $C_{1-4}$alkyl;

L³ is selected from $C_{1-7}$alkylene optionally substituted with one or more groups selected from OH and $C_{1-4}$alkyl;

R¹ is H or $NH_2$;

R² and R³ are independently selected from OH, $OR^7$, $SR^7$, $NHR^7$, $NR^7_2$, and $R^p$;

R⁴ is $NH_2$, NHOH, $N_3$, $NHR^7$, $NR^7_2$, $C(O)NHR^7$, $C(O)NR^7_2$, SH, $SR^7$, CHO, alkyl, alkenyl, alkynyl, aryl, heteroaryl, cycloalkyl, heterocycloalkyl optionally substituted with one or more OH and/or $CH_2OH$, $C(O)R^7$, $OR^7$, $COOR^7$, CN, COOH, OH, $P(O)R^5R^6$ or —O—$C_{1-2}$alkylene-P(O) $R^5R^6$;

R⁵ and R⁶ are independently selected from OH, $OR^7$, $SR^7$, $NHR^7$, $NR^7_2$, and $R^p$, wherein $R^p$ is a prodrug substituent and wherein the or each R⁷, where present, is independently selected from alkyl, alkenyl, alkynyl, aryl, acyl and arylalkyl optionally containing one or more heteroatoms;

wherein the combined number of non-hydrogen atoms in L¹ and L² excluding the number of atoms in the optional substituent(s), where present, is between 3 and 5; and wherein the combined number of non-hydrogen atoms in L³ and R⁴ excluding R⁵ and R⁶ is less than or equal to 8, or a pharmaceutically acceptable salt thereof.

In the compounds of the invention L¹ is selected from $C_{1-4}$alkylene, $C_{2-4}$alkenylene and $C_{2-4}$alkynylene wherein L¹ is optionally substituted with one or more $C_{1-4}$alkyl, $C_{2-4}$alkenyl or $C_{2-4}$alkynyl. In some embodiments, L¹ is $C_{1-4}$alkylene optionally substituted with one or more $C_{1-4}$alkyl. For example, L¹ may be $C_{1-3}$alkylene, preferably ethylene. In those embodiments where L¹ is ethylene the compounds of the invention may be represented by any one of the following formulae:

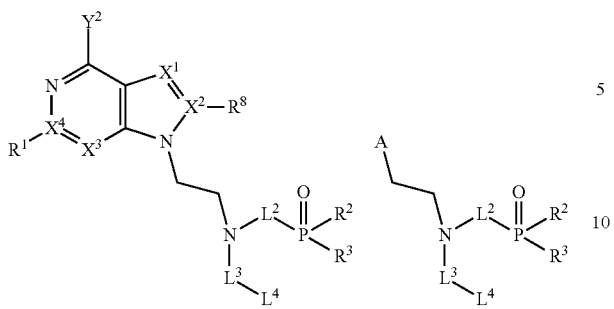

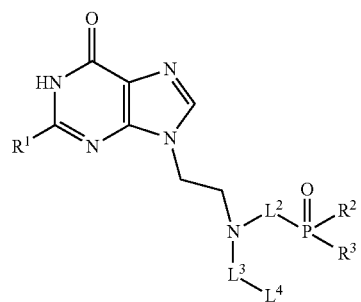

In the compounds of the invention $L^2$ is selected from $C_{1-4}$alkylene, $C_{2-4}$alkenylene and $C_{2-4}$alkynylene wherein $L^1$ is optionally substituted with one or more $C_{1-4}$alkyl, $C_{2-4}$alkenyl or $C_{2-4}$alkynyl. In some embodiments, $L^1$ is $C_{1-4}$alkylene optionally substituted with one or more $C_{1-4}$alkyl. For example, $L^2$ may be $C_{1-3}$alkylene, preferably ethylene. In those embodiments where $L^2$ is ethylene the compounds of the invention may be represented by any one of the following formulae:

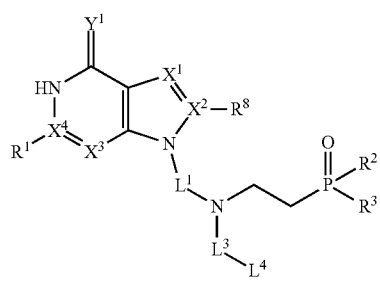

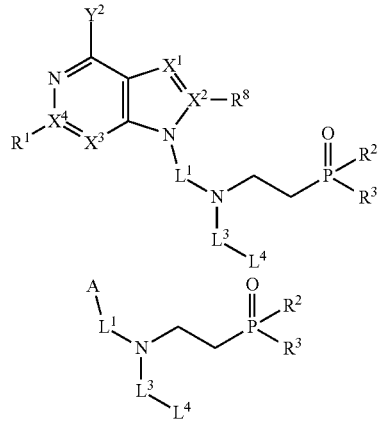

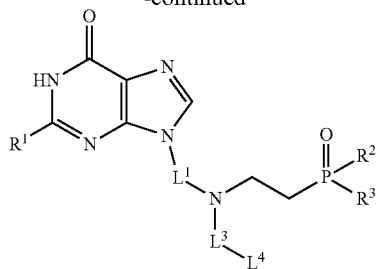

In the compounds of the invention the combined number of non-hydrogen atoms in $L^1$ and $L^2$ excluding the number of atoms in the optional substituent(s), where present, is between 3 and 5. Without wishing to be bound by theory, it is believed that this represents the optimal spacing of the —P(O)$R^2R^3$ group from the purine moiety for binding to 6-oxopurine phosphoribosyltransferases such as hypoxanthine-guanine-(xanthine) phosphoribosyltransferase (HG(X) PRT). For example, when $L^1$ is ethylene and $L^2$ is methylene the combined number of non-hydrogen atoms in $L^1$ and $L^2$ is 3. By way of further example, when $L^1$ is 2-methylpropylene and $L^2$ is ethylene the combined number of non-hydrogen atoms in $L^1$ and $L^2$ excluding the number of atoms in the methyl substituent on the propylene group is 5. Preferably the combined number of non-hydrogen atoms in $L^1$ and $L^2$ excluding the number of atoms in the optional substituent(s), where present, is 4. For example when $L^1$ is ethylene and $L^2$ is ethylene then the combined number of non-hydrogen atoms in $L^1$ and $L^2$ is 4. In such embodiments the compounds of the invention may be represented by any one of the following formulae:

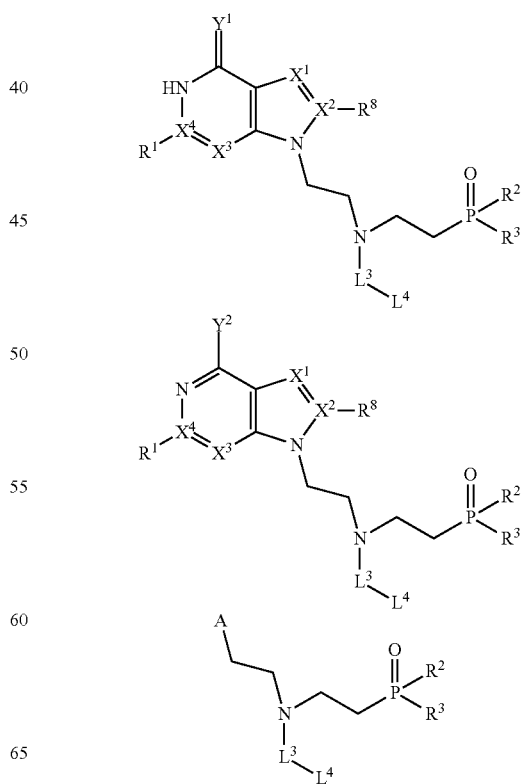

-continued

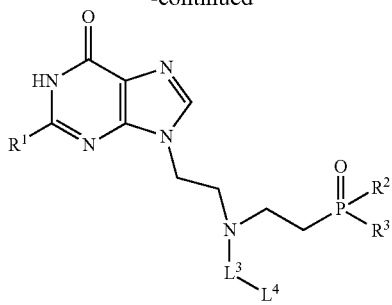

In the compounds of the invention $L^3$ is selected from $C_{1-7}$alkylene, $C_{2-7}$alkenylene and $C_{2-7}$alkynylene wherein $L^3$ is optionally substituted with one or more groups selected from OH, $C_{1-4}$alkyl, $C_{2-4}$alkenyl or $C_{2-4}$alkynyl. In some embodiments $L^3$ is $C_{1-7}$alkylene optionally substituted with one or more OH or $C_{1-4}$alkyl. For example, $L^3$ may be $C_{1-4}$alkylene, such as methylene, ethylene or propylene.

In the compounds of the invention $R^1$ is alkyl, aryl, heteroaryl, alkenyl, alkynyl, arylalkyl, heteroarylalkyl, $NR^7_2$, halogen, $OR^7$, H or $NH_2$. In some embodiments $R^1$ is H or $NH_2$.

In the compounds of the invention $R^2$ and $R^3$ are independently selected from OH, $OR^7$, $SR^7$, $NHR^7$, $NR^7_2$, and $R^P$. $R^P$ is a prodrug substituent. In some embodiments $R^2$ and $R^3$ are independently selected from. OH, $OR^7$ and $R^P$. In preferred embodiments, $R^2$ and $R^3$ are independently selected from OH, —O$^i$Pr, —OPr, —OEt, —OMe and $R^P$ In the compounds of the invention $R^4$ is $NH_2$, NHOH, $N_3$, $NHR^7$, $NR^7_2$, $C(O)NHR^7$, $C(O)NR^7_2$, SH, $SR^7$, CHO, alkyl, alkenyl, alkynyl, aryl, heteroaryl, cycloalkyl, heterocycloalkyl optionally substituted with one or more OH and/or $CH_2OH$, $C(O)R^7$, $OR^7$, $COOR^7$, CN, COOH, OH, $P(O)R^5R^6$ or —O—$C_{1-2}$alkylene-$P(O)R^5R^6$. In some embodiments $R^4$ is $C(O)R^7$, $OR^7$, $COOR^7$, CN, COOH, OH, $P(O)R^5R^6$, —O—$C_{1-2}$alkylene-$P(O)R^5R^6$. In yet further embodiments, $R^4$ is $COOR^7$, CN, COOH, OH, $P(O)R^5R^6$, —O—$C_{1-2}$alkylene-$P(O)R^5R^6$. In some embodiments $R^4$ is —COOEt or —COOMe. In other embodiments $R^4$ is —O—$C_{1-2}$alkylene-$P(O)R^5R^6$, preferably —O—$CH_2$—$P(O)R^5R^6$.

In the compounds of the invention $R^5$ and $R^6$ are independently selected from OH, $OR^7$, $SR^7$, $NHR^7$, $NR^7_2$, and $R^P$. $R^P$ is a prodrug substituent. In some embodiments $R^5$ and $R^6$ are independently selected from OH, $OR^7$ and $R^P$. In preferred embodiments, $R^5$ and $R^6$ are independently selected from OH, —O$^i$Pr, —OPr, —OEt, —OMe and $R^P$.

In the compounds of the invention the or each $R^7$, where present, is independently selected from alkyl, alkenyl, alkynyl, aryl, acyl and arylalkyl optionally containing one or more heteroatoms. In preferred embodiments, $R^7$ is alkyl, preferably $C_{1-3}$alkyl, more preferably $C_{1-2}$alkyl.

In the compounds of the invention $R^8$ is selected from H, alkyl, aryl, heteroaryl, $NR^7_2$, halogen, $OR^7$. Preferably $R^8$ is selected from H, alkyl and halogen, more preferably $R^8$ is selected from H, $C_{1-4}$alkyl and halogen. In some embodiments $R^8$ is H.

It is believed that the $R^4$ group appended via the $L^3$ group assists the compounds of the invention to provide excellent affinity and/or selectivity for 6-oxopurine phosphoribosyltransferases such as hypoxanthine-guanine-(xanthine) phosphoribosyltransferase (HG(X)PRT). In some embodiments the $R^4$ group interacts with the binding subsite of the enzyme target through one or more of the following interactions: electrostatic, hydrophobic, aromatic stacking, hydrogen bonding. In some embodiments the $R^4$ group is electron rich. Furthermore, it is believed that the spacing of the $R^4$ group from the purine moiety is important such that in the compounds of the invention the combined number of non-hydrogen atoms in $L^3$ and $R^4$ excluding $R^5$ and $R^6$ is less than or equal to 8. By way of example when $L^3$ is $C_7$alkylene and $R^4$ is OH the combined number of non-hydrogen atoms in $L^3$ and $R^4$ is 8. By way of further example, when $L^3$ is $C_3$alkylene (eg 1,3-propylene) and $R^4$ is —COOEt the combined number of non-hydrogen atoms in $L^3$ and $R^4$ is 8.

In the compounds of the invention. $Y^1$ where present is selected from S and O, and $Y^2$ where present is selected from halogen. In preferred embodiments the compound of the invention has the following formula where $Y^1$ is selected from S and O:

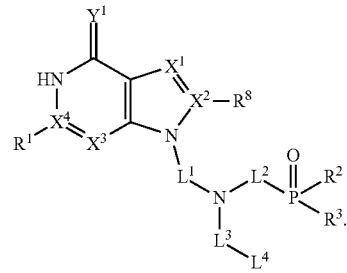

In even more preferred embodiments $Y^1$ is O.

It will be understood that the compounds of the invention may exist in a plurality of equivalent tautomeric forms. For the sake of clarity the compounds have been depicted as single tautomers, despite all such tautomeric forms being considered within the scope of the invention.

In the compounds of the invention A is selected from one of the following:

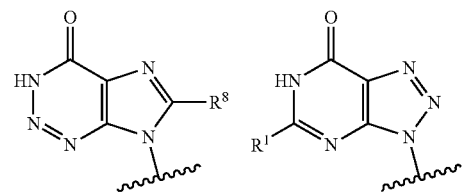

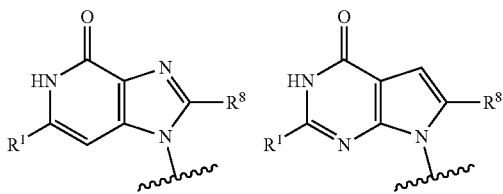

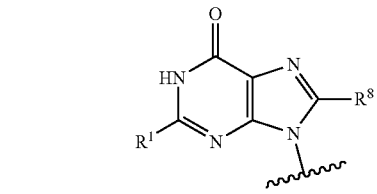

In some embodiments, A is:

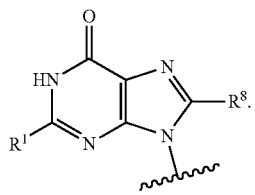

The term "alkyl" includes saturated aliphatic groups, including straight-chain alkyl groups (e.g., methyl, ethyl, propyl, butyl, pentyl, hexyl, heptyl, octyl, nonyl, decyl, etc.) and branched-chain alkyl groups (isopropyl, tert-butyl, isobutyl, etc.). In some embodiments "alkyl" refers to straight chained alkyl. The expression "$C_{x-y}$alkyl", wherein x is 1-5 and y is 2-10 indicates an alkyl group (straight- or branched-chain) containing the specified number of carbon atoms. For example, the expression $C_{1-4}$alkyl includes, but is not limited to, methyl, ethyl, propyl, butyl, isopropyl, tert-butyl and isobutyl. The term "alkylene" refers to a divalent alkyl group.

In one embodiment, a straight chain or branched chain alkyl has 10 or fewer carbon atoms (ie $C_{1-10}$). In some embodiments a straight chain or branched chain alkyl has 6 or fewer carbon atoms (ie $C_{1-6}$). In some embodiments a straight chain or branched chain alkyl has 3 or fewer carbon atoms (ie $C_{1-3}$).

The term "cycloalkyl" includes saturated cyclic aliphatic groups (cyclopropyl, cyclopentyl, cyclohexyl, cycloheptyl, cyclooctyl). The term $C_{3-6}$cycloalkyl includes, but is not limited to, cyclopropyl, cyclopentyl, and cyclohexyl. Likewise, preferred cycloalkyls have from 4-7 carbon atoms in their ring structure, and more preferably have 5 or 6 carbons in the ring structure. As used herein the term "heterocycloalkyl" refers to a cycloalkyl group containing one or more endocyclic heteroatoms.

The term "alkenyl" includes unsaturated aliphatic groups analogous in length and possible substitution to the alkyls described above, but which contain at least one double bond. For example, the term "alkenyl" includes straight-chain alkenyl groups (e.g., ethenyl, propenyl, butenyl, pentenyl, hexenyl, heptenyl, octenyl, nonenyl, decenyl, etc.) and branched-chain alkenyl groups. In some embodiments "alkenyl" refers to straight chained alkenyl. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms. The term "alkenylene" refers to a divalent alkenyl group.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.) and branched-chain alkynyl groups. In some embodiments "alkynyl" refers to straight chained alkynyl. In certain embodiments, a straight chain or branched chain alkynyl group has 6 or fewer carbon atoms in its backbone (e.g., $C_2$-$C_6$ for straight chain, $C_1$-$C_6$ for branched chain). The term $C_2$-$C_6$ includes alkynyl groups containing 2 to 6 carbon atoms. The term "alkynylene" refers to a divalent alkynyl group.

The term "amine" or "amino" should be understood as being broadly applied to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom.

The term "amide," "amido" or "aminocarbonyl" includes compounds or moieties which contain a nitrogen atom which is bound to the carbon of a carbonyl or a thiocarbonyl group.

The term "aryl" refers to aromatic monocyclic (eg phenyl) or polycyclic groups (e.g., tricyclic, bicyclic, e.g., naphthalene, anthryl, phenanthryl). Aryl groups can also be fused or bridged with alicyclic or heterocyclic rings which are not aromatic so as to form a polycycle (e.g., tetralin, methylenedioxyphenyl).

The term "heteroaryl", as used herein, represents a monocyclic or bicyclic ring, typically of up to 7 atoms in each ring, wherein at least one ring is aromatic and contains from 1 to 4 heteroatoms selected from the group consisting of O, N and S. Heteroaryl groups within the scope of this definition include but are not limited to benzimidazole (otherwise known as benzoimadazole), acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indoiyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indoiyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoiine, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyt, quinoxalinyl, tetrahydropyranyl, tetrazolyl, tetrazolopyridyl, thiadiazolyl, thiazolyl, thienyl, triazolyl, azetidinyl. 1,4-dioxanyl, hexahydroazepinyl, piperazinyl, piperidinyl, pyridin-2-onyl, pyrrolidinyl, moφpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom. A referred to herein "heterocycloalkyl" refers to a saturated heterocyclyl group. In some embodiments the heterocycloalkyl group is optionally substituted with one or more OH and/or $CH_2OH$. An example of such a group is the simple sugar ribose.

The term "acyl" includes compounds and moieties which contain the acyl radical (CH$_3$CO—) or a carbonyl group such as CH$_3$CH$_2$CH$_2$CO—.

The term "alkoxy" includes substituted and unsubstituted alkyl, alkenyl, and alkynyl groups covalently linked to an oxygen atom. Examples of alkoxy groups include methoxy, ethoxy, isopropyloxy (isopropoxy), propoxy, butoxy, and pentoxy groups and may include cyclic groups such as cyclopentoxy.

The term "carbonyl" or "carboxy" includes compounds and moieties which contain a carbon connected with a double bond to an oxygen atom, and tautomeric forms thereof. Examples of moieties that contain a carbonyl include aldehydes, ketones, carboxylic acids, amides, esters, anhydrides, etc. The term "carboxy moiety" or "carbonyl moiety" refers to groups such as "alkylcarbonyl" groups wherein an alkyl group is covalently bound to a carbonyl group, "alkenyl carbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide), aminocarbonyloxy moieties, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. moieties.

The term "thiocarbonyl" or "thiocarboxy" includes compounds and moieties which contain a carbon connected with a double bond to a sulfur atom. The term "thiocarbonyl moiety" includes moieties that are analogous to carbonyl moieties. For example, "thiocarbonyl" moieties include aminothiocarbonyl, wherein an amino group is bound to the carbon atom of the thiocarbonyl group, furthermore other thiocarbonyl moieties include, oxythiocarbonyls (oxygen bound to the carbon atom), aminothiocarbonylamino groups, etc.

The term "ester" includes compounds and moieties that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "hydroxy" or "hydroxyl" includes groups with an —OH.

The term "halogen" includes fluorine, chlorine, bromine and iodine. In some embodiments halogen refers to fluorine or chlorine.

The terms "polycyclyl" or "polycyclic radical" include moieties with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings.

The term "heteroatom" includes atoms of any element other than carbon or hydrogen. Preferred heteroatoms are nitrogen, oxygen, sulfur and phosphorus. Particularly preferred heteroatoms are nitrogen and oxygen.

As used herein, the term "optionally substituted" typically refers to where a hydrogen atom on a group has been substituted with a non-hydrogen group. Unless the context requires otherwise, such as where the optional substituent has been explicitly referred to, examples of optional subtituents are detailed below. Any optionally substituted group may bear one, two, three or more optional substituents.

In some embodiments the optional substituents are selected from: optionally substituted $C_{1-6}$alkyl; optionally substituted $C_{6-10}$aryl; halogen; —OH; —NH$_2$; —NO$_2$; —SO$_2$NH$_2$; —COOH; —COO($C_{1-6}$alkyl); —NHCOO ($C_{1-6}$alkyl); —NH—COR$^a$ wherein R$^a$ is H or $C_{1-6}$alkyl; —NR$^a$R$^b$ wherein R$^a$ is H or $C_{1-6}$alkyl and R$^b$ is H or $C_{1-6}$alkyl; —C(O)NR$^a$R$^b$, wherein R$^a$ is H or $C_{1-6}$alkyl and R$^b$ is H, $C_{1-6}$alkyl; —C(O)R$^a$ wherein R$^a$ is H or $C_{1-6}$alkyl; or –Y-Q wherein:
  Y is selected from: —O—, —NH—, —N($C_{1-6}$alkyl)-, —NHSO$_2$—, —SO$_2$NH—, —NHCONH—, —NH-CON($C_{1-6}$alkyl)—, —S(O)$_q$— wherein q is 0, 1 or 2, —C(O)NH—, —C(O)N(CH$_3$)—, —NHC(O)—, —C(O)—, —NHC(NH)NH—, or absent, and
  Q is selected from: optionally substituted $C_{6-10}$aryl; optionally substituted 5-10 membered $C_{1-9}$heteroaryl; optionally substituted 3-10 membered $C_{1-9}$heterocyclyl; optionally substituted $C_{3-10}$cycloalkyl; optionally substituted $C_{1-6}$alkyl; optionally substituted $C_{1-6}$alkylacyl; optionally substituted $C_{2-6}$alkenyl; optionally substituted $C_{2-6}$alkynyl; and hydrogen.

In other embodiments the optional substituents are selected from: optionally substituted $C_{1-6}$alkyl; optionally substituted $C_{6-10}$aryl; halogen; —OH; —NH$_2$; —COOH; —COO($C_{1-6}$alkyl); —NR$^a$R$^b$ wherein R$^a$ is H or $C_{1-6}$alkyl and R$^b$ is H or $C_{1-6}$alkyl; —NH—COR$^a$ wherein R$^a$ is H or $C_{1-6}$alkyl; —C(O)NR$^a$R$^b$, wherein R$^a$ is H or $C_{1-6}$alkyl, and R$^b$ is H, $C_{1-6}$alkyl; C(O)R$^a$ wherein R$^a$ is H or $C_{1-6}$alkyl; or —Y-Q, wherein:
  Y is selected from: —O—, —NH—, —N($C_{1-6}$alkyl)-, —NHCONH—, —S—, —C(O)NH—, —C(O)N(CH$_3$)—, —NHC(O)—, —C(O)—, —NHC(NH)NH—, or absent, and
  Q is selected from: $C_{6-10}$aryl optionally substituted with —OH; 5-10 membered $C_{1-9}$heteroaryl; 3-10 membered $C_{1-9}$heterocyclyl; $C_{3-10}$cycloalkyl; $C_{1-6}$alkyl; $C_{1-6}$alkylacyl; $C_{2-6}$alkenyl; $C_{2-6}$alkynyl; and hydrogen.

Additionally, any number of the listed functional groups and molecules may be combined to create a larger molecular architecture. For example, the terms "phenyl," "carbonyl" (or "=O"), "—O—," "—OH," and $C_1$alkyl and $C_3$alkylene (i.e., —CH$_3$ and —CH$_2$CH$_2$CH$_2$—) can be combined to form a 3-methoxy-4-propoxybenzoic acid substituent. In another example the terms aryl and alkyl can be combined to form an arylalkyl group, an example of which is a phenylmethyl group, otherwise known as a benzylic group. It is to be understood that when combining functional groups and molecules to create a larger molecular architecture, hydrogens can be removed or added, as required to satisfy the valence of each atom.

It is to be understood that all of the compounds of the invention described above will further include bonds between adjacent atoms and/or hydrogens as required to satisfy the valence of each atom. That is, double bonds and/or hydrogen atoms are typically added to provide the following number of total bonds to each of the following types of atoms: carbon: four bonds; nitrogen: three bonds; oxygen: two bonds; and sulfur: two, four or six bonds. It is also to be understood that definitions given to the variables of the generic formulae described herein will result in molecular structures that are in agreement with standard organic chemistry definitions and knowledge, e.g., valency rules.

Whilst it is preferable that the compounds of the invention contain no asymmetric carbon atoms to assist with purification/isolation, it will be noted that the structures of some of the compounds of this invention include asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein may be obtained through art recognized synthesis strategies. It will also be noted that the substituents of some of the compounds of this invention include isomeric cyclic structures. It is to be understood accordingly that constitutional isomers of particular substituents are included within the scope of this invention, unless indicated otherwise. For example, the term "tetrazole" includes tetrazole, 2H-tetrazole, 3H-tetrazole, 4H-tetrazole and 5H-tetrazole.

The skilled person will appreciate that there are a range of techniques available to produce achiral compounds of the invention in racemic, enantioenriched or enantiopure forms. For example, enantioenriched or enantiopure forms of the compounds may be produced through stereoselective synthesis and/or through the use of chromatographic or selective recrystallisation techniques. In some embodiments the compounds of the invention may be prepared by appending a natural or unnatural amino acid to the phosphonate group to form a prodrug. Accordingly, a racemic mixture of amino acids may be used to prepare a racemic mixture of a compound of the invention, an enantioenriched amino acid may be used to prepare an enantioenriched mixture of a compound of the invention and an enantiopure amino acid may be used to prepare an enantiopure compound of the invention.

The compounds and methods of the present invention may be used in the treatment and/or prevention of a range of microbial infections. As used herein, treatment may include alleviating or ameliorating the symptoms, diseases or conditions associated with the microbial infection being treated, including reducing the severity and/or frequency of the microbial infection. As used herein, prevention may include preventing or delaying the onset of, inhibiting the progression of, or halting or reversing altogether the onset or progression of the particular symptoms, disease or condition associated with a microbial infection.

The terms "microbial", "microorganism", etc includes any microscopic organism or taxonomically related macroscopic organism within the categories algae, bacteria, fungi and protozoa or the like. Preferably the microorganism is a bacteria or protozoa, most preferably a protozoa. In this respect the present invention is predicated, in part, on the susceptibility of microorganisms to inhibition of 6-oxopurine phosphoribosyltransferases such as the hypoxanthine-guanine-(xanthine) phosphoribosyltransferase (HG(X)PRT) enzyme involved in the purine salvage pathway. Accordingly the compounds of the invention are particularly well suited to those organisms that are auxotrophic for the purine ring present in nucleosides, and thus rely, or substantially rely, on the salvage pathway to provide the purine moiety for reproduction. To this end it is understood that there are known techniques (such as genomic sequencing or gene deletion experiments) that may be used to determine whether a Microorganism is reliant, or substantially reliant, on the salvage pathway for reproduction. In some embodiments the compounds of the invention are particularly well suited to preventing or treating a microbial infection caused by a microorganism that cannot sustain itself in the absence of the salvage pathway. In some embodiments such microorganisms possess no de novo, or substantially no de novo, pathway for purine synthesis.

The bacterial infection may be caused by one or more species selected from one or more of the Gram-negative bacterial genera: *Acinetobacter; Actinobacillus; Bartonella; Bordetella; Brucella; Burkholderia; Campylobacter; Cyanobacteria; Enterobacter; Erwinia; Escherichia; Francisella; Helicobacter; Hemophilus; Klebsiella; Legionella; Moraxella; Morganella; Mycobacterium; Neisseria; Pasteurella; Proteus; Providencia; Pseudomonas; Salmonella; Serratia; Shigella; Stenotrophomonas; Treponema; Vibrio*; and *Yersinia*. Specific examples include, but are not limited to, infections caused by *Helicobacter pylori* and uropathogenic *Escherichia coli*.

The bacterial infection may be caused by one or more species selected from one or more of the Gram-positive bacterial genera: *Actinobacteria; Bacillus; Clostridium; Corynebacterium; Enterococcus; Listeria; Nocardia; Staphylococcus*; and *Streptococcus*.

Protozoal infections include, but are not limited to, infections caused by *Leishmania, Toxoplasma, Plasmodia* (which are understood to be the causative agent(s) of malarial infection), *Theileria, Anaplasma, Giardia, Tritrichomonas, Trypanosoma, Schistosoma. Coccidia*, and *Babesia*. Specific examples include *Plasmodium falciparum, Plasmodium vivax, Plasmodium malariae, Plasmodium knowlesi, Plasmodium ovale* and *Giardia lamblia*.

In this respect, it is believed that the compounds of the invention are particularly well suited to the prevention or treatment of infections caused by *Plasmodia* spp. (especially *Plasmodium falciparum* and *Plasmodium vivax*), *Giardia* spp. (especially *Giardia lamblia*), *Trypanosoma* spp., *Schistosoma* spp., *Helicobacter* spp. (such as *Helicobacter pylori*), *Mycobacterium tuberculosis*, and certain uropathogenic *Escherichia coli*.

It will be understood that certain nucleosides may modulate the activity of one or more kinases, including certain nucleosides bearing saccharide and/or polyphosphate moieties (for example diphosphate or triphosphate moieties). To the extent that it is preferable that the compounds of the invention do not adversely modulate the activity of one or more kinases, such compounds do not fall within the scope of the invention.

Examples of microbial infections include bacterial or fungal wound infections, mucosal infections, enteric infections, septic conditions, pneumonia, trachoma, ornithosis, trichomoniasis, fungal infections and salmonellosis, such as in veterinary practice. The compounds of the invention may also be used for the treatment of resistant microbial species or in various fields where antiseptic treatment or disinfection of materials is required, for example, surface disinfection.

The term "subject" is intended to include organisms such as mammals, e.g. humans, dogs, cows, horses, pigs, sheep, goats, cats, mice, rabbits, rats, and transgenic non-human animals. In certain embodiments, the subject is a human, e.g. a human suffering from, at risk of suffering from, or potentially capable of suffering from a microbial infection. In another embodiment, the subject is a cell.

The compounds of the invention may be in crystalline form or as solvates (e.g. hydrates) and it is intended that both forms are within the scope of the present invention. The term "solvate" is a complex of variable stoichiometry formed by a solute (in this invention, a compound of the invention) and a solvent. Such solvents should preferably not interfere with the biological activity of the solute. Solvents may be, by way of example, water, acetone, ethanol or acetic acid. Methods of solvation are generally known within the art.

The present invention also provides a pharmaceutical composition comprising a therapeutically effective amount of a compound as hereinbefore defined, or a pharmaceutically acceptable salt thereof, together with at least one pharmaceutically acceptable carrier or diluent.

Pharmaceutically acceptable acid addition salts may be prepared from inorganic and organic acids. Examples of inorganic acids include hydrochloric acid, hydrobromic acid, sulfuric acid, nitric acid, phosphoric acid and the like. Examples of organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. For example, the nitrogen atom in the acyclic portion of the compounds of the invention may undergo reaction with an acid to form the acid addition salt.

Pharmaceutically acceptable base addition salts may be prepared from inorganic and organic bases. Corresponding counterions derived from inorganic bases include the sodium, potassium, lithium, ammonium, calcium and magnesiim salts. Organic bases include primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. For example, where the compound of the invention possesses a phosphonate group the compound may undergo reaction with a base to form the base addition salt.

Acid/base addition salts tend to be more soluble in aqueous solvents than the corresponding free acid/base forms.

The term "composition" is intended to include the formulation of an active ingredient with encapsulating material as carrier, to give a capsule in which the active ingredient (with or without other carrier) is surrounded by carriers.

While the compounds as hereinbefore described, or pharmaceutically acceptable salt thereof, may be the sole active ingredient administered to the subject, the administration of other active ingredient(s) with the compound is within the scope of the invention. For example, the compound could be administered with one or more therapeutic agents in combination. The combination may allow for separate, sequential or simultaneous administration of the compound as hereinbefore described with the other active ingredient(s). The combination may be provided in the form of a pharmaceutical composition.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the compound care should be taken to ensure that the activity of the compound is not destroyed in the process and that the compound is able to reach its site of action without being destroyed. In some circumstances it may be necessary to protect the compound by means known in the art, such as, for example, micro encapsulation or coating (such as the use of enteric coating). Similarly the route of administration chosen should be such that the compound reaches its site of action.

Those skilled in the art may readily determine appropriate formulations for the compounds of the present invention using conventional approaches. Identification of preferred pH ranges and suitable excipients, for example antioxidants, is routine in the art. Buffer systems are routinely used to provide pH values of a desired range and include carboxylic acid buffers for example acetate, citrate, lactate and succinate. A variety of antioxidants are available for such formulations including phenolic compounds such as BHT or vitamin E, reducing agents such as methionine or sulphite, and metal chelators such as EDTA.

The compounds as hereinbefore described, or pharmaceutically acceptable salt thereof, may be prepared in parenteral dosage forms, including those suitable for intravenous, intrathecal, and intracerebral or epidural delivery. The pharmaceutical forms suitable for injectable use include sterile injectable solutions or dispersions, and sterile powders for the extemporaneous preparation of sterile injectable solutions. They should be stable under the conditions of manufacture and storage and may be preserved against reduction or oxidation and the contaminating action of microorganisms such as bacteria or fungi.

The solvent or dispersion medium for the injectable solution or dispersion may contain any of the conventional solvent or carrier systems for the compound, and may, contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolarity, for example, sugars or sodium chloride. Preferably, the formulation for injection will be isotonic with blood. Prolonged absorption of the injectable compositions can be brought about by the use in the compositions of agents delaying absorption, for example, aluminium monostearate and gelatin. Pharmaceutical forms suitable for injectable use may be delivered by any appropriate route including intravenous, intramuscular, intracerebral, intrathecal, epidural injection or infusion.

Sterile injectable solutions are prepared by incorporating the active compound in the required amount in the appropriate solvent with various of the other ingredients such as those enumerated above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

Other pharmaceutical forms include oral and enteral formulations of the present invention, in which the active compound may be formulated with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal or sublingual tablets, troches, capsules, elixirs, suspensions, syrups, wafers, and the like. The amount of active compound in such therapeutically useful compositions is such that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil, of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations, including those that allow specific delivery of the active compound to specific regions of the gut.

Liquid formulations may also be administered enterally via a stomach or oesophageal tube.

Enteral formulations may be prepared in the form of suppositories by mixing with appropriate bases, such as emulsifying bases or water-soluble bases. It is also possible, but not necessary, for the compounds of the present invention to be administered topically, intranasally, intravaginally, intraocularly and the like.

The present invention also extends to any other forms suitable for administration, for example topical application such as creams, lotions and gels, or compositions suitable for inhalation or intranasal delivery, for example solutions, dry powders, suspensions or emulsions.

The compounds of the present invention may be administered by inhalation in the form of an aerosol spray from a pressurised dispenser or container, which contains a propellant such as carbon dioxide gas, dichlorodifluoromethane, nitrogen, propane or other suitable gas or combination of gases. The compounds may also be administered using a nebuliser.

Pharmaceutically acceptable vehicles and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate the compositions in dosage unit form for ease of administration and uniformity of dosage. Dosage unit form as used herein refers to physically discrete units suited as unitary dosages for the mammalian subjects to be treated; each unit containing a predetermined qUantity of active material calculated to produce the desired therapeutic effect in association with the required pharmaceutically acceptable vehicle. The specification for the novel dosage unit forms of the invention arc dictated by and directly dependent on (a) the unique characteristics of the active material and the particular therapeutic effect to be achieved, and (b) the limitations inherent in the art of compounding active materials for the treatment of disease in living subjects having a diseased condition in which bodily health is impaired as herein disclosed in detail.

As mentioned above the principal active ingredient may be compounded for convenient and effective administration in therapeutically effective amounts with a suitable pharmaceutically acceptable vehicle in dosage unit form. A unit dosage form can, for example, contain the principal active compound in amounts ranging from 0.25 µg to about 200 mg. Expressed in proportions, the active compound may be present in concentrations ranging from about 0.25 µg to about 200 mg/mL of carrier. In the case of compositions containing supplementary active ingredients, the dosages are determined by reference to the usual dose and manner of administration of the said ingredients.

The terms "therapeutically effective amount" and "effective amount" refer to that amount which is sufficient to effect treatment, as defined below, when administered to an animal, preferably a mammal, more preferably a human in need of such treatment. The therapeutically effective amount or effective amount will vary depending on the subject and nature of symptom, disease or condition being treated, the severity of the symptom, disease or condition and the manner of administration, and may be determined routinely by one of ordinary skill in the art.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The invention will now be described with reference to some specific examples and drawings. However, it is to be understood that the particularity of the following description is not to supercede the generality of the invention as hereinbefore described.

EXAMPLES

One general synthetic approach to construction of the acyclic portion of the compounds of the invention comprised an aza-Michael addition reaction wherein vinylphosphonate was reacted with an amino group to form a β-aminophosphonate moiety. Whilst there are a number of different solvents and catalysts available for this reaction it was found that water without any catalyst or organic co-solvent was effective. Thus, aza-Michael addition of diethyl vinylphosphonate to one equivalent of 2-aminoethanol produced desired phosphonate 1 (77% yield) together with bisphosphonate 2a (8% yield) as shown in Scheme 2.

Scheme 2

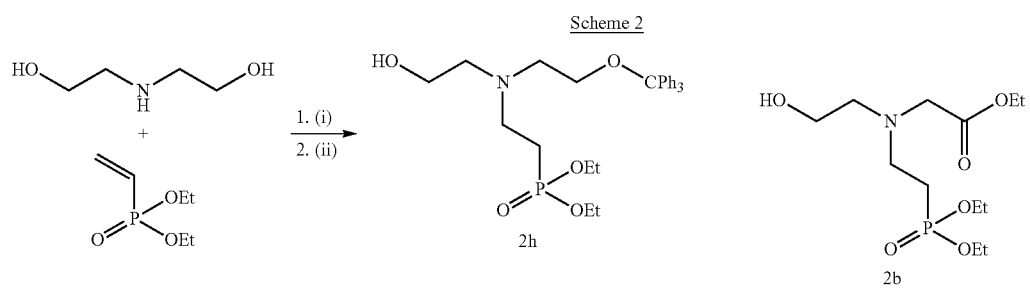

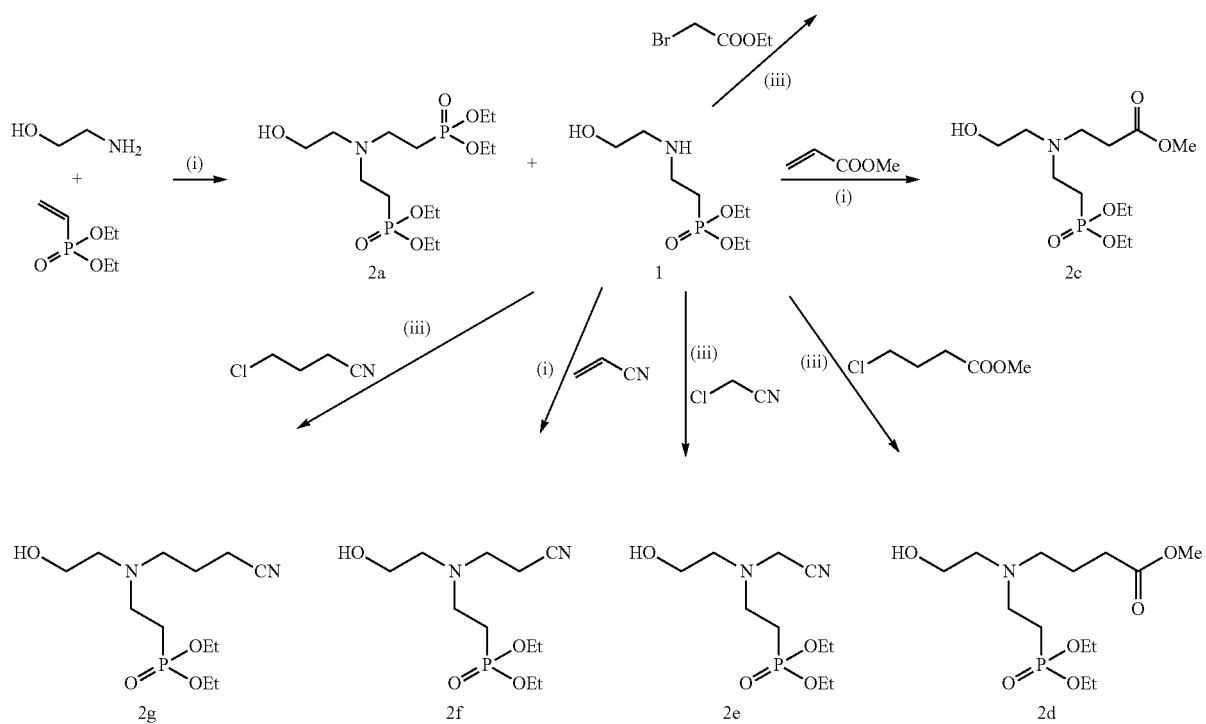

(i) H₂O, r.t.; (ii) TrCl, Et₃N, DMAP, CH₂Cl₂; (iii) K₂CO₃, MeCN

Diethyl 2-(2-hydroxyethylamino)ethylphosphonate 1 was used as the starting material for the synthesis of a series of branched phosphonates 2b-2g (Scheme 2). Two types of reactions were used to introduce suitable substituents to the NH-group of the phosphonate 1: a) alkylation with the corresponding halogen derivative was used to attach a one-carbon or three-carbon chain bearing a cyano or carboxylic ester group (compounds 2b, 2d, 2e and 2g, isolated yields 64-77%); b) a further aza-Michael addition of methyl acrylate or acrylonitrile to the phosphonate 1 was employed to prepare compounds 2c and 2f with a two-carbon chain (isolated yields 50% and 78%). To complement the series, a protected hydroxyethyl derivative 2h was synthesized by aza-Michael addition of diethyl vinylphosphonate to diethanolamine followed by tritylation of one of the hydroxy groups. (Scheme 2).

The series of hydroxyderivatives 2a-2h prepared by the above mentioned straightforward approach was used to introduce branched acyclic moieties to the $N^9$-position of 6-chloropttrine or 2-amino-6-chloropurine (Scheme 3) via Mitsunobu reaction. 6-Chloropurine phosphonates 3a-3h were produced in good yields (about 80%). In the case of 2-amino-6-chloropurine phosphonates 4a-4g, the Mitsunobu reaction had to be followed by heating in water/tetrahydrofuran to decompose the triphenylphosphoranylidene intermediate rising from the presence of the free amino group. Anomalous behavior was observed for the tritylated derivative 4h: the triphenylphosphoranylidene intermediate was very stable when the trityl group was present. After deprotection under acidic conditions (the 6-chloro group was unexpectedly completely preserved), the triphenylphosphoranylidene 4i was decomposed using standard procedures.

The chlorine atom of phosphonates 3a-3h and 4a-4g, 4i was next displaced with hydroxyl by nucleophilic aromatic substitution in acidic conditions (75% aqueous trifluoroacetic acid) to form hypoxanthine and guanine phosphonates 5a-5g and 6a-6g, 6i. The tritylated derivative 3h was simultaneously deprotected to give the hydroxyderivative 5i. Instead of direct Mitsunobu reaction of 6-oxopurines with poor regioselectivity, this two-step approach was used for the preparation of 9-substituted hypoxanthine and guanine to avoid the separation of $N^7$ and $N^9$ regioisomers.

Scheme 3
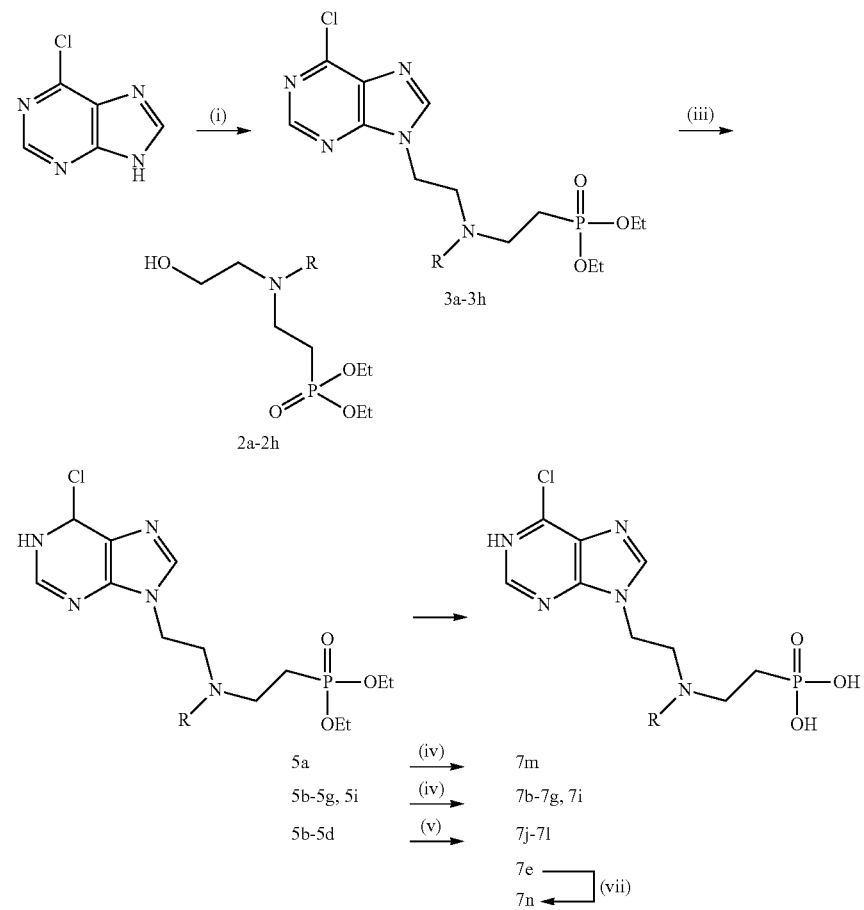
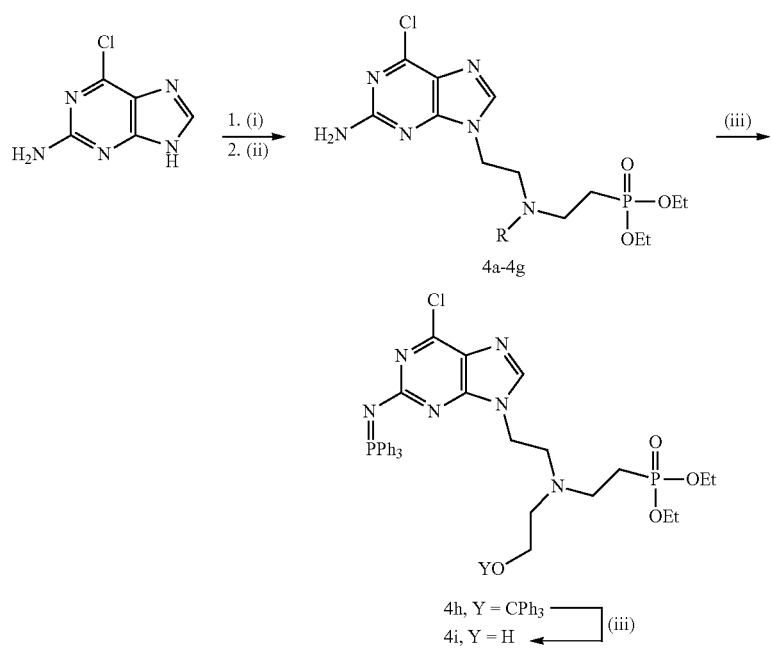

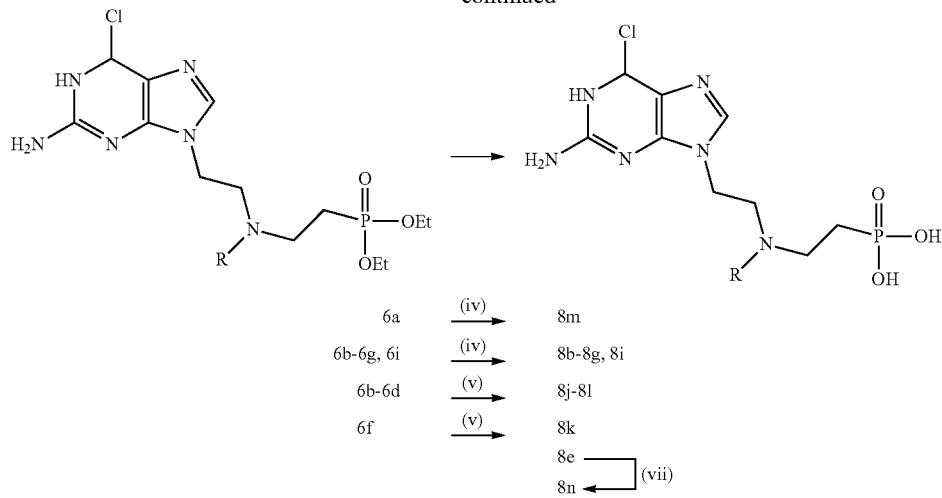

| | | |
|---|---|---|
| 6a | (iv) | 8m |
| 6b-6g, 6i | (iv) | 8b-8g, 8i |
| 6b-6d | (v) | 8j-8l |
| 6f | (v) | 8k |
| 8e | (vii) | |
| 8n | | | a: R = CH₂CH₂PO(OEt)₂
b: R = CH₂COOEt
c: R = (CH₂)₂COOMe
d: R = (CH₂)₃COOMe
e: R = CH₂CN
f: R = (CH₂)₂CN
g: R = (CH₂)₃CN
h: R = (CH₂)₂OCPh₃
i: R = (CH₂)₂OH
j: R = CH₂COOH
k: R = (CH₂)₂COOH
l: R = (CH₂)₃COOH
m: R = CH₂CH₂PO(OH)₂
n: R = H (i) PPh₃, DIAD, THF; (ii) addition of H₂O, heating; (iii) 75% aqueous trifluoroacetic acid; (iv) Me₃SiBr, MeCN, DMF, 2,6-lutidine: (v) 1. aqueous NaOH, THF, MeOH: 2. Me₃SiBr, MeCN, DMF. 2,6-lutidine; (vi) 1. aqueous NaOH, MeOH: 2. Me₃SiBr. MeCN, DMF. 2,6-lutidine; (vii) DMF, heating To form free phosphonic acids 7b-7g, 7i and 8b-8g, 8i, ester groups of diethyl phosphonates 5b-5g, 5i and 6b-6g, 6i were cleaved under standard conditions using Me₃SiBr/acetonitrile followed by hydrolysis; 2,6-lutidine was added to neutralize contamination of bromotrimethylsilane by HBr. In the tetraethyl bisphosphonates 5a and 6a, both phosphonate moieties were simultaneously deprotected and free bisphosphonic acids 7m and 8m were obtained. Alkaline hydrolysis of carboxylic acid esters 5b-5d, 6b and 6d with aqueous sodium hydroxide followed by cleavage of phosphonate esters under the above mentioned conditions afforded the corresponding phosphonic acids 7j-7l, 8j and 8l with free carboxylic acid moiety in the side chain. The phosphonic acid 8k was prepared by the alkaline hydrolysis of the cyanoderivative 6f again followed by cleavage of the phosphonate ester (Scheme 3).

During the purification of the cyanomethyl phosphonic acids 7e and 8e, partial cleavage of the side-chain was observed at higher temperature. To complement the series of target ANPs, these unstable cyanomethyl derivatives were refluxed in dimethylformamide for several days to obtain compounds 7n and 8n with an unsubstituted NH-moiety (Scheme 3). All target ANPs described above, 7b-7g, 7i-7n, 8b-8g and 8i-8n, were purified by preparative HPLC or ion-exchange chromatography.

Example 1

9-[(N-(2-Ethoxy-2-oxoethyl)-N-(2-phosphonethyl))-2-aminoethyl]guanine

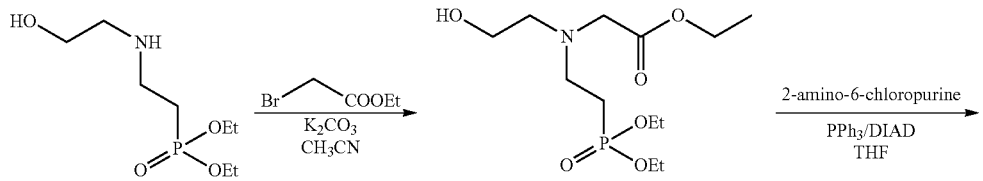

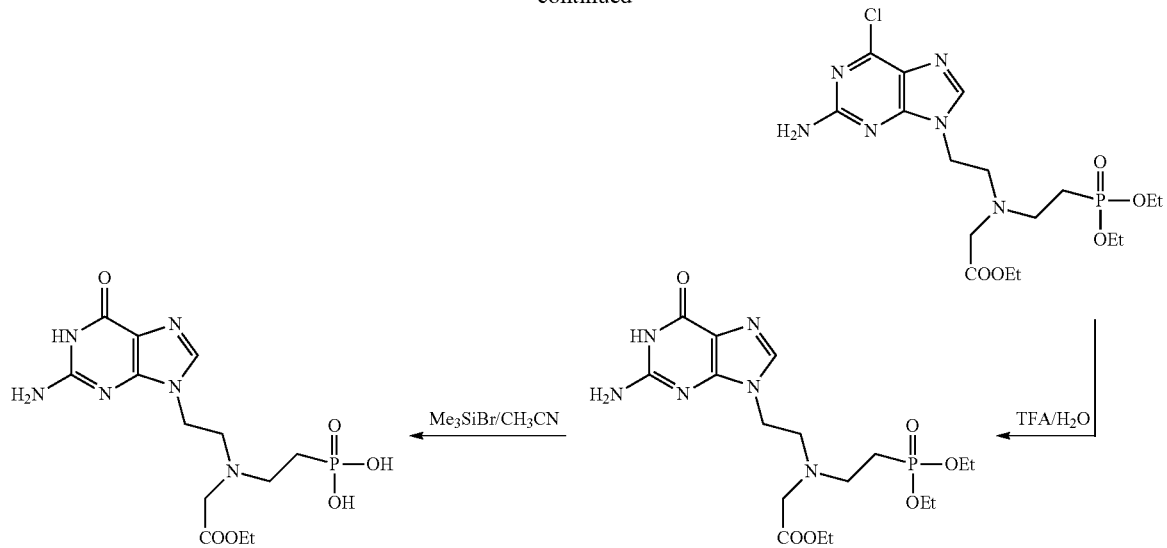

The mixture of diethyl 2-(2-hydroxyethylamino)ethylphosphonate (6 g, 26.7 mmol) and $K_2CO_3$ (3.7 g, 26.7 mmol) in dry acetonitrile (80 ml) was cooled to −10° C. and ethyl bromoacetate (6.7 g, 40 mmol) was added. The reaction mixture was stirred at −10° C. for 1 h and then at room temperature for 2 days. The solvent was then removed by evaporation. Water and $CHCl_3$ were added, the organic layer separated, washed with brine and dried over anhydrous $MgSO_4$. After filtration, solvent was evaporated and the residue was purified by column chromatography on silica gel ($CHCl_3$-MeOH), the ethyl 2-((2-(diethoxyphosphoryl)ethyl)(2-hydroxyethyl)amino)acetate was obtained in 64% yield (5.32g).

To a solution of triphenylphosphine (6.3 g, 24 mmol) in dry THF (100 ml) cooled to −30° C. under argon atmosphere diisopropylazadicarboxylate (DIAD, 4.4 ml, 23 mmol) was added slowly. The mixture was stirred for 30 minutes and this preformed complex was added to 2-amino-6-chloropurine (3.8 g, 22.6 mmol), dry THF (70 ml) and ethyl 2-((2-(diethoxyphosphoryl)ethyl)(2-hydroxyethyl)amino)acetate (3.5 g, 11.2 mmol) at −30° C. under argon. The resulting mixture was slowly warmed to room temperature and stirred for 48 h. Then water (30 ml) was added and the mixture was heated at 80° C. for 30 h. Solvent was evaporated the residue was codistilled with toluene or ethanol and the crude mixture purified by chromatography on silica gel (MeOH—$CHCl_3$). Diethyl 9-[(N-(2-ethoxy-2-oxoethyl)-N-(2-phosphonoethyl))-2-aminoethyt]-2-amino-6-chloropurine was isolated in 47% yield (2.44 g).

This intermediate (1.85 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—$CHCl_3$) diethyl 9-[(N-(2-ethoxy-2-oxoethyl)-N-(2-phosphonoethyl))-2-aminoethyl]guanine was obtained in 95% yield (1.69 g).

A mixture of this diethyl ester (0.89 g, 2 mmol), acetonitrile (20 ml), 2,6-lutidine (0.1 ml) and $BrSiMe_3$ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N-(2-Ethoxy-2-oxoethyl)-N-(2-phosphonoethyl))-2-aminoethyl]guanine was obtained as a white solid in 35% yield (0.27 g).

$^1$H NMR (DMSO-$d_6$): 10.54 s, 1 H (NH); 7.70 s, 1 H (H-8); 6.43 s, 2 H ($NH_2$); 4.05 q, 2 H, J=7.1 (Et); 3.97 t, 2 H, J(1',2')=6.0 (H-1'); 3.39 s, 2 H (H-5'); 2.88 t, 2 H, =6.0 (H-2'); 2.79 dd, 2 H, J=7.4 and 16.0 (H-3'); 1.56 in, 2 H (H-4'); 1.17 t, 3 H, J=7.1 (Et). $^{13}$C NMR (DMSO-$d_6$): 170.78 (CO); 156.74 (C-6); 153.38 (C-2); 151.06 (C-4); 137.89 (C-8); 116.11 (C-5); 59.82 (Et); 53.81, 52.28 and 48.05 (C-2', C-5' and C-3'); 40.94 (C-1'); 26.23, J(P,C)=131.7 (C-4'); 14.05 (Et). Anal. Calcd for $C_{13}H_{21}N_6O_6P \cdot 2/3H_2O$: C, 39.00; H, 5.62; N, 20.99. Found: C, 38.85; H. 5.55; N, 20.92. MS (ESI−): m/z=387 [M−H]$^−$.

Example 2

9-[(N-(3-Methoxy-3-oxopropyl)-N-(2-phosphonoethyl))-2-aminoethyl]guanine

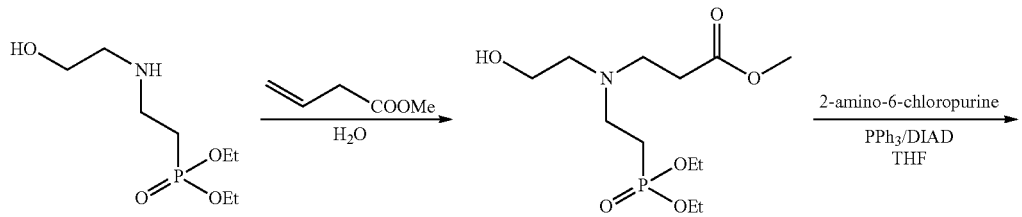

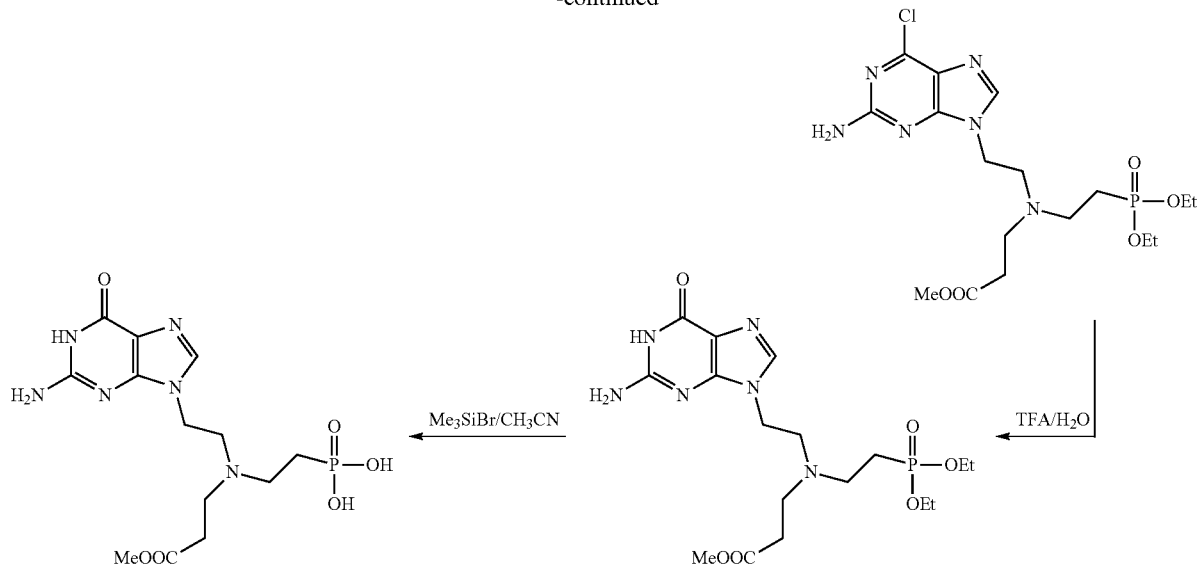

Methyl acrylate (4.5 g, 45 mmol) was added to the solution of diethyl 2-(2-hydroxyethylamino)ethylphosphonate (6.75 g, 30 mmol) in water (70 ml). The reaction mixture was stirred overnight at room temperature, evaporated and the residue codistilled with toluene. The resulting methyl 3((2-(diethoxyphosphoryl)ethyl)(2-hydroxyethyl)amino)propanoate was purified by column chromatography on silica gel (CHCl$_3$-MeOH), the product was obtained as yellow oil in 50% yield (4.67 g). To a solution of triphenylphosphine (6.3 g, 24 mmol) in dry THF (100 ml) cooled to −30° C. under argon atmosphere diisopropylazadicarboxylate (DIAD, 4.4 ml, 23 mmol) was added slowly. The mixture was stirred for 30 minutes and this preformed complex was added to 2-amino-6-chloropurine (3.8 g, 22.6 mmol), dry THF (70 ml) and 3-((2-(diethoxyphosphoryl)ethyl)(2-hydroxyethyl) amino)propanoate (3.5 g, 11.2 mmol) at −30° C. under argon. The resulting mixture was slowly warmed to room temperature and stirred for 48 h. Then water (30 ml) was added and the mixture was heated at 80° C. for 30 h. Solvent was evaporated the residue was codistilled with toluene or ethanol and the crude mixture purified by chromatography on silica gel (MeOH—CHCl$_3$). Diethyl 9-[(N-(3-methoxy-3-oxopropyl)-N-(2-phosphonoethyl))-2-aminoethyl]-2-amino-6-chloropurine was isolated in 59% yield (3.06 g).

This intermediate (1.85 g, 4 mmol) was dissolved in trifluoroacetic acid (aqueous, 75%, 20 ml) and stirred overnight. The solvent was evaporated and the residue codistilled with water (3×) and ethanol. After chromatography On silica gel (MeOH—CHCl$_3$) diethyl 9-[(N-(3-methoxy-3-oxopropyl)-N-(2-phosphonoethyl))-2-aminoethyl]guanine was obtained in 73% yield (1.30 g).

A mixture of this diethyl ester (0.89 g, 2 mmol), acetonitrile (20 ml), dimethylformamide (6 ml), 2,6-lutidine (0.1 ml) and BrSiMe$_3$ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N-(3-Methoxy-3-oxopropyl)-N-(2-phosphonoethyl))-2-aminoethyl]guanine was obtained as a white solid in 31% yield (0.24 g). $^1$H NMR (DMSO-d$_6$): 10.55 s, 1 H (NH); 7.62 s, 1 H (H-8); 6.46 s, 2 H (NH$_2$); 3.98 t, 2 H, J(1',2')=6.1 (H-1'); 3.54 s, 3 H (Me); 2.75 m, 6 H (H-2', H-3', H-5'); 2.36 t, 2 H, J(6',5')=6.9 (H-6'); 1.67 m, 2 H (H-4'). $^{13}$C NMR (DMSO-d$_6$): 172.04 (CO); 156.66 (C-6); 153.32 (C-2); 150.93 (C-4); 137.66 (C-8); 116.24 (C-5); 51.14 (Me); 51.94, 48.13, 47.31 (C-2', C-5' and C-3'); 40.59 (C-1'); 31.45 (C-6'); 24.58 d, J(P,C)=131.5 (C-4'). Anal. Calcd for C$_{13}$H$_{21}$N$_6$O$_6$P.H$_2$O: C, 38.43; H, 5.71; N, 20.68. Found: C, 38.13; H, 5.86; N, 20.48. MS (ESI-): m/z=387 [M−H]$^-$.

Example 3

9-[(N-(4-Methoxy-4-oxobutyl)-N-(2-phosphonoethyl))-2-aminoethyl]guanine

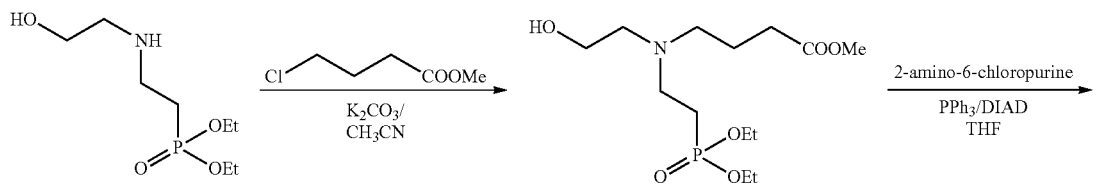

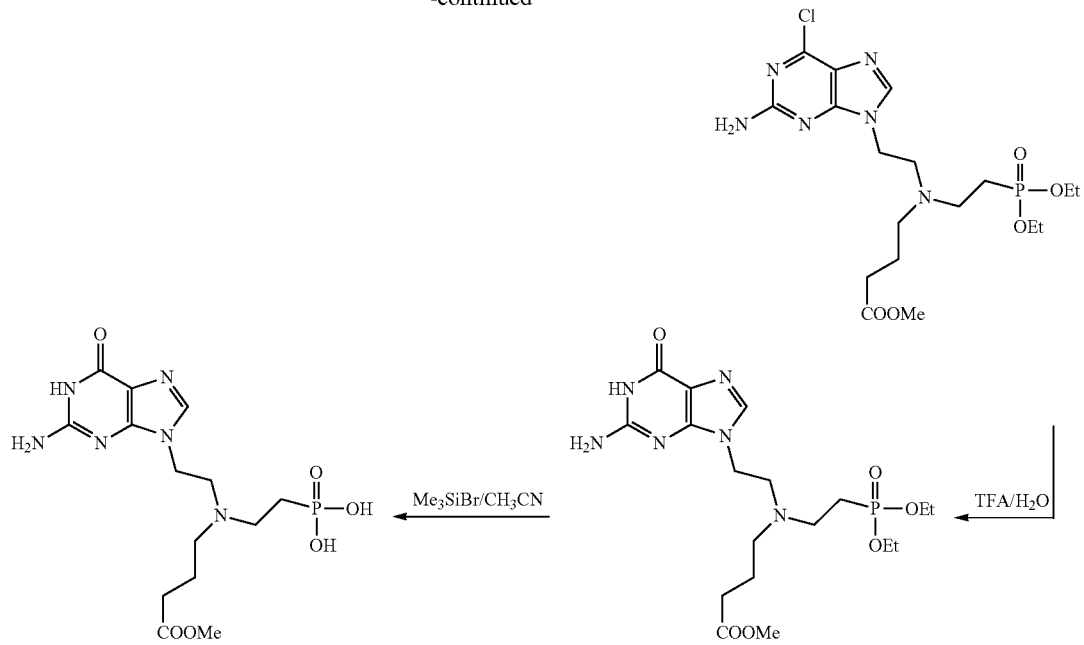

The mixture of diethyl 2-(2-hydroxyethylamino)ethylphosphonate (6 g, 26.7 mmol) and K$_2$CO$_3$ (3.7 g, 26.7 mmol) in dry acetonitrile (80 ml) was cooled to −10° C. and methyl 4-chlorobutyrate (5.5 g, 40 mmol) was added. The reaction mixture was stirred at −10° C. for 1 h and then heated at 80° C. for 70 h. The solvent was then removed by evaporation. Water and CHCl$_3$ were added, the organic layer separated, washed with brine and dried over anhydrous MgSO$_4$. After filtration, solvent was evaporated and the residue was purified by column chromatography on silica gel (CHCl$_3$-MeOH), the methyl 34(2-(diethoxyphosphoryp])ethyl)(2-hydroxyethyl)amino)butanoate was obtained in 77% yield (6.68 g).

To a solution of triphenylphosphine (6.3 g, 24 mmol) in dry THF (100 ml) cooled to −30° C. under argon atmosphere diisopropylazadicarboxylate (DIAD, 4.4 ml, 23 mmol) was added slowly. The mixture was stirred for 30 minutes and this preformed complex was added to 2-amino-6-chloropurine (3.8 g, 22.6 mmol), dry THF (70 ml) and methyl 3-((2-(diethoxyphosphoryl)ethyl)(2-hydroxyethyl)amino)butanoate (3.64 g, 11.2 mmol) at −30° C. under argon. The resulting mixture was slowly warmed to room temperature and stirred for 48 h. Then water (30 ml) was added and the mixture was heated at 80° C. for 30 h. Solvent was evaporated the residue was codistilled with toluene or ethanol and the crude mixture purified by chromatography on silica gel (MeOH—CHCl$_3$). Diethyl 9-[(N-(4-methoxy-4-oxobutyl)-N-(2-phosphonoethyl))-2-aminoethyl]-2-amino-6-chloropurine was isolated in 80% yield (4.27 g).

This intermediate (1.91 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) diethyl 9-[(N-(4-methoxy-4-oxobutyl)-N-(2-phosphonoethyl))-2-aminoethyl]guanine was obtained in 57% yield (1.04 g).

A mixture of this diethyl ester (0.92 g, 2 mmol), acetonitrile (20 ml), 2,6-lutidine (0.1 nil) and BrSiMe$_3$ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N-(4-Methoxy-4-oxobutyl)-N-(2-phosphonoethyl))-2-aminoethyl]guanine was obtained as a white foam in 58% yield (0.47 g).

$^1$H NMR (DMSO-d$_6$): 10.66 s, 1 H (NH); 7.69 s, 1 H (H-8); 6.56 s, 2 H (NH$_2$); 4.11 t, 2 H, J(1',2')=5.4 (H-1'); 3.56 s, 3 H (Me); 3.02 t, 2 H, J(2',1')=5.4 (H-2'); 2.96 dd, 2 H, J=15.0 and 8.3 (H-3'); 2.68 t, 2 H, J(5',6')=6.6 (H-5'); 2.23 t, 2 H, J(7',6')=7.2 (H-7'); 1.71 m, 2 H (H-4'), 1.63 m, 2 H (H-6'). $^{13}$C NMR (DMSO-d$_6$): 172.88 (CO); 156.65 (C-6); 153.46 (C-2); 150.96 (C-4); 137.54 (C-8); 116.28 (C-5); 51.13 (Me); 51.50, 51.26 and 47.83 (C-2', C-3' and C-5'); 30.30 (C-7'); 24.10 d, J(P,C)=129.3 (C-4'), 20.61 (C-6'). Anal. Calcd for C$_{14}$H$_{23}$N$_6$O$_6$P.H$_2$O: C, 40.00; H, 5.99; N. 19.99. Found: C, 39.99; H, 5.91; N, 19.77. MS (ESI): m/z=401 [M−H]$^-$.

Example 4

9-[(N-(2-Cyanomethyl)-N-(2-phosphonoethyl))-2-aminoethyl]guanine

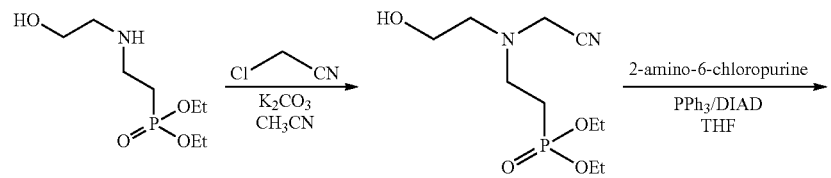

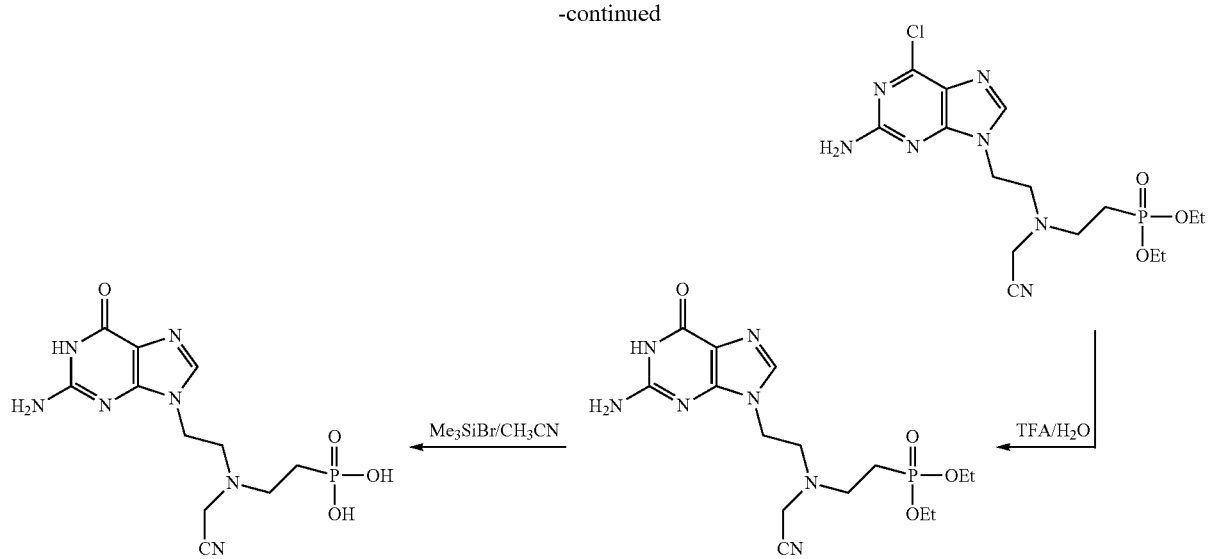

The mixture of diethyl 2-(2-hydroxyethylamino)ethylphosphonate (6 g, 26.7 mmol) and K$_2$CO$_3$ (3.7 g, 26.7 mmol) in dry acetonitrile (80 ml) was cooled to −10° C. and chloroacetonitrile (3.0 g, 40 mmol) was added. The reaction mixture was stirred at −10 for 1 h and then at room temperature for 2 days. The solvent was then removed by evaporation. Water and CHCl$_3$ were added, the organic layer separated, washed with brine and dried over anhydrous MgSO$_4$. After filtration, solvent was evaporated and the residue was purified by column chromatography on silica gel (CHCl$_3$-MeOH), the diethyl 2-(2-cyanomethylamino)ethylphosphonate was obtained in 65% yield (4.58 g).

To a solution of triphenylphosphine (6.3 g, 24 mmol) in dry THF (100 ml) cooled to −30° C. under argon atmosphere diisopropylazadicarboxylate (DIAD, 4.4 ml, 23 mmol) was added slowly. The mixture was stirred for 30 minutes and this preformed complex was added to 2-amino-6-chloropurine (3.8 g, 22.6 mmol), dry THF (70 ml) and diethyl 2-(2-cyanomethylamino)ethylphosphonate (2.96 g, 11.2 mmol) at −30° C. under argon. The resulting mixture was slowly warmed to room temperature and stirred for 48 h. Then water (30 ml) was added and the mixture was heated at 80° C. for 30 h. Solvent was evaporated the residue was codistilled with toluene or ethanol and the crude mixture purified by chromatography on silica gel (MeOH—CHCl$_3$). Diethyl 9-[(N-(2-cyanomethyl)-N-(2-phosphonoethyl))-2-aminoethyl]-2-amino-6-chloropurine was isolated in 73% yield (3.40 g).

This intermediate (1.85 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) diethyl 9-[(N-(2-cyanotnethyl)-N-(2-phosphonoethyl))-2-aminoethyl]guanine was obtained in 95% yield (1.51 g).

A mixture of this diethyl ester (0.89 g, 2 mmol), acetonitrile (20 ml), dimethylformamide (10 ml), 2,6-lutidine (0.1 ml) and BrSiMe$_3$ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N-(2-Cyanomethyl)-N-(2-phosphonoethyl))-2-aminoethyl]guanine was obtained as a white solid in 89% yield (0.61 g). $^1$H NMR (DMSO-d$_6$): 11.39 s. 1 H (NH); 9.05 s, 1 H (H-8); 7.07 s, 2H (NH$_2$); 4.19 t, 2 H, J(1',2')=5.2 (H-1'); 3.82 s, 2 H (H-5'); 4.19 t, 2 H, J(2',1')=5.2 (H-2'); 2.71dd, 2 H, J=8.5 and 16.8 (H-3'); 1.65 m, 2 H (H-4'). $^{13}$C NMR (DMSO-d$_6$): 155.02 (C-6); 153.73 (C-2); 149.81 (C-4); 137.49 (C-8); 116.08 (CN and C-5); 51.68 and 47.78 (C-2' and C-3'); 41.80 and 41.27 (C-1' and C-5'); 25.74 d, J(P,C)=134.2 (C-4'). Anal. Calcd for C$_{11}$H$_{16}$N$_7$O$_4$P.MeOH: C, 38.61; H, 5.40; N, 26.26. Found: C, 38.12; H, 5.15; N, 26.39. MS (ESI−): m/z=340 [M−H]$^-$.

Example 5

9-[(N-(2-Cyanaethyl)-N-(2-phosphonoethyl))-2-aminoethyl]guanine

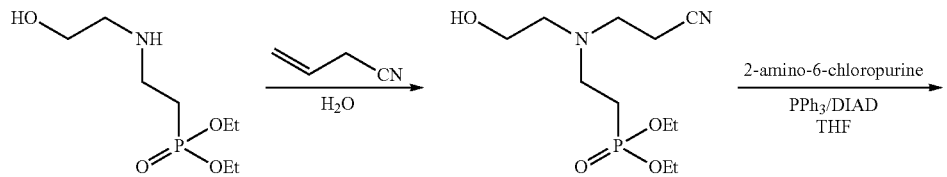

-continued

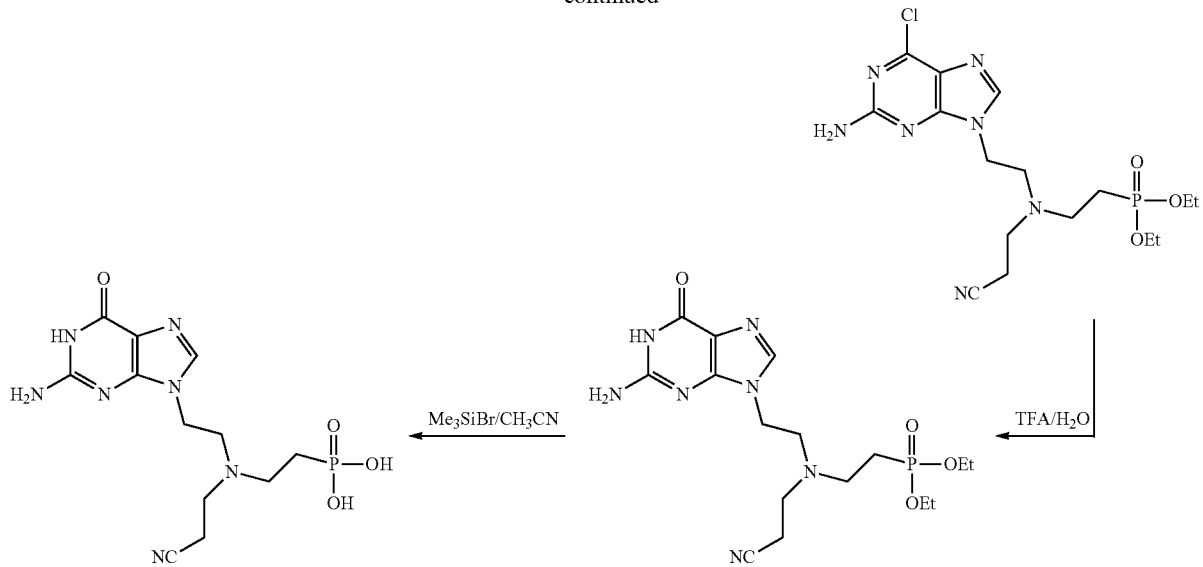

Acrylonitrile (3.02 g, 45 mmol) was added to the solution of diethyl 2-(2-hydroxyethylamino)ethylphosphonate (6.75 g, 30 mmol) in water (70 ml). The reaction mixture was stirred overnight at room temperature, evaporated and the residue codistilled with toluene. The resulting diethyl 2-(2-cyanoethylamino)ethylphosphonate was purified by column chromatography on silica gel (CHCl$_3$-MeOH), the product was obtained in 78% yield (6.51 g).

To a solution of triphenylphosphine (6.3 g, 24 mmol) in dry THF (100 ml) cooled to −30 °C. under argon atmosphere diisopropylazadicarboxylate (DIAD, 4.4 ml, 23 mmol) was added slowly. The mixture was stirred for 30 minutes and this preformed complex was added to 2-amino-6-chloropurine (3.8 g, 22.6 mmol), dry THF (70 ml) and diethyl 2-(2-cyanoethylamino)ethylphosphonate (3.11 g, 11.2 mmol) at −30° C., under argon. The resulting mixture was slowly warmed to room temperature and stirred for 48 h. Then water (30 ml) was added and the mixture was heated at 80° C. for 30 h. Solvent was evaporated the residue was codistilled with toluene or ethanol and the crude mixture purified by chromatography on silica gel (MeOH—CHCl$_3$). Diethyl 9-[(N-(2-cyanoethyl)-N-(2-phosphonoethyl))-2-aminoethyl]-2-amino-6-chloropurine was isolated in 78% yield (3.76 g).

This intermediate (1.72 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) diethyl 9-[(N-(2-cyanoethyl)-N-(2-phosphonoethyl))-2-aminoethyl]guanine was obtained in 95% yield (1.56 g).

A mixture of this diethyl ester (0.82 g, 2 mmol), acetonitrile (20 ml), dimethylformamide (4 ml), 2,6-lutidine (0.1 ml) and BrSiMe$_3$ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N-(2-Cyanoethyl)-N-(2-phosphonoethyl))-2-aminoethyl]guanine was obtained as a white foam in 36% yield (0.26 g). $^1$H NMR (DMSO-d$_6$): 10.53 s, 1 H (NH); 7.70 s, 1 H (H-8); 6.44 s, 2 H (NH$_2$); 3.97 t, 2 H, J(1',2')=6.3 (H-1*); 2.73 m, 6 H (H-2', H-3' and H-5'); 2.53 t, 2 H, J(6', 5')=6.5 (H-6'); 1.59 m, 2 H (H-4'). $^{13}$C NMR (DMSO-d$_6$): 156.69 (C-6); 153.34 (C-2); 150.99 (C-4); 137.65 (C-8); 119.94 (CN); 116.26 (C-5); 51.90, 48.31 and 47.24 (C-2', C-5' and C-3'); 40.89 (C-1'); 25.14 d, J(P,C)=131.4 (C-4'); 15.56 (C-6'). Anal. Calcd for C$_{12}$H$_{18}$N$_7$O$_4$P.MeOH: C, 40.31; H, 5.72; N, 25.31. Found: C, 40.22; H, 5.78; N, 25.09. MS (ESI−): m/z=354 [M−H]$^-$.

Example 6

9-[(N-(2-Cyanopropyl)-N-(2-phosphonoethyl))-2-aminoethyl]guanine

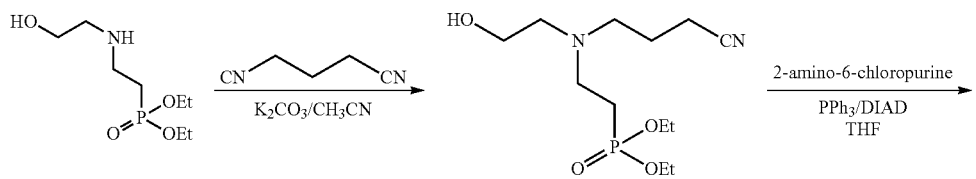

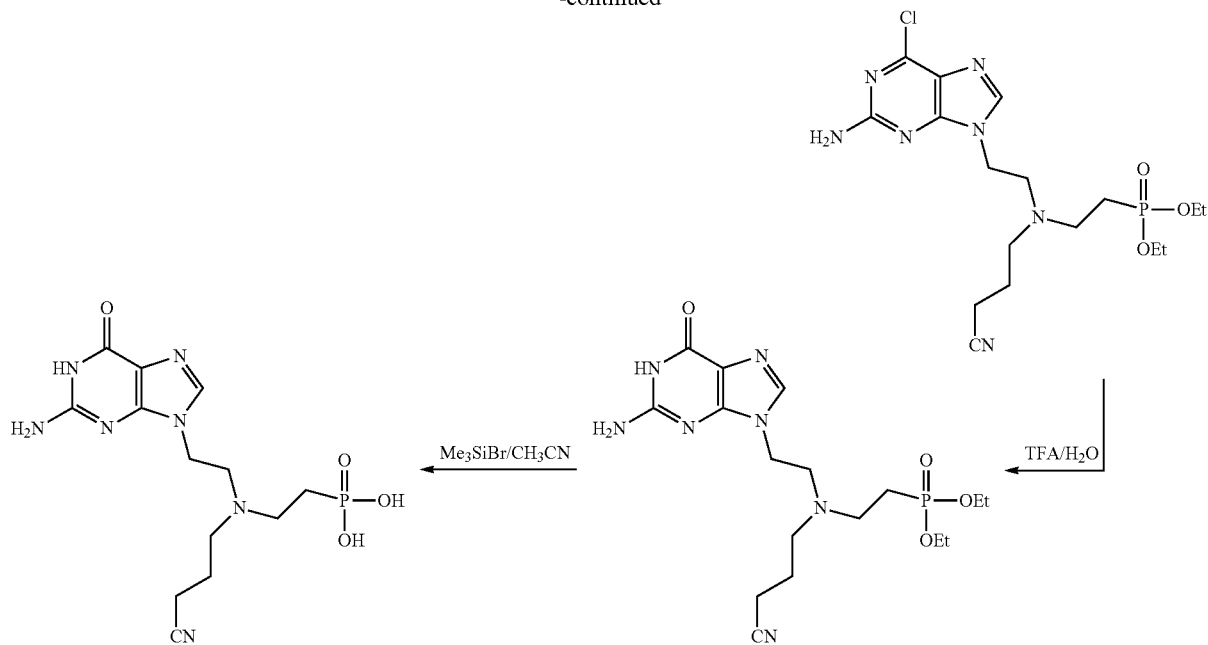

The mixture of diethyl 2-(2-hydroxyethylamino)ethylphosphonate (6 g, 26.7 mmol) and K$_2$CO$_3$ (3.7 g, 26.7 mmol) in dry acetonitrile (80 ml) was cooled to –10° C. and 4-chlorobutyronitrile (4.16 g, 40 mmol) was added. The reaction mixture was stirred at –10° C. for 1 h and then heated at 80° C. for 70 h. The solvent was then removed by evaporatation. Water and CHCl$_3$ were added, the organic layer separated, washed with brine and dried over anhydrous MgSO$_4$. After filtration, solvent was evaporated and the residue was purified by column chromatography on silica gel (CHCl$_3$-MeOH), the diethyl 2-(2-cyanopropylamino)ethylphosphonate was obtained in 69% yield (5.38 g).

To a solution of triphenylphosphine (6.3 g, 24 mmol) in dry THF (100 ml) cooled to –30° C. under argon atmosphere diisopropylazadicarboxylate (DIAD, 4.4 ml, 23 mmol) was added slowly. The mixture was stirred for 30 minutes and this preformed complex was added to 2-amino-6-chloropurine (3.8 g, 22.6 mmol), dry THF (70 ml) and diethyl 2-(2-cyanopropylamino)ethylphosphonate (3.27 g, 11.2 mmol) at –30° C. under argon. The resulting mixture was slowly warmed to room temperature and stirred for 48 h. Then water (30 nil) was added and the mixture was heated at 80° C. for 30 h. Solvent was evaporated the residue was codistilled with toluene or ethanol and the crude mixture purified by chromatography on silica gel (MeOH—CHCl$_3$). Diethyl 9-[(N-(2-cyanopropyl)-N-(2-phosphonoethyl))-2-aminoethyl]-2-amino-6-chloropurine was isolated in 66% yield (3.28 g).

This intermediate (1.78 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) diethyl 9-[(N-(2-cyanopropyl)-N-(2-phosphonoethyl))-2-aminoethyl]guanine was obtained in 95% yield (1.62 g).

A mixture of this diethyl ester (0.85 g, 2 mmol), acetonitrile (20 ml), dimethylformamide (14 ml), 2,6-lutidine (0.1 ml) and BrSiMe$_3$ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N-(2-Cyanopropyl)-N-(2-phosphonoethyl))-2-aminoethyl]guanine was obtained as a white solid in 58% yield (0.43 g). $^1$H NMR (DMSO-d$_6$): 10.61 s, 1 H (NH); 7.71 s, 1 H (H-8); 6.50 s, 2 H (NH$_2$); 4.06 t, 2H, =5.8 (H-1'); 2.89 m. 2 H(H-2'); 2.86 m, 2 H (11-3'); 2.62 t, 2 H, J(5',6')=6.8 (H-5'); 2.34 t, 2 H, J(7',6')=7.2 (H- 7'); 1.70 m, 2 H (H-4'); 1.67 m. 2 H $^{13}$C NMR (DMSO-d$_6$): 156.60 (C-6); 153.41 (C-2); 150.96 (C-4); 137.60 (C-8); 120.27 (CN); 116.21 (C-5); 51.74, 50.86 and 47.47 (C-2', C-3' and C-5'); 40.23 (C-1'); 24.23 d, J(P,C)=130.73 (C-4'); 21.96 (C-6'); 13.51 (C-6'). Anal. Calcd for C$_{13}$H$_{20}$N$_7$O$_4$P.3/2H$_2$O: C, 39.40; H, 5.85; N. 24.74. Found: C, 39.12; H, 5.46; N, 24.33. MS (ESI): m/z=368 [M+H]$^+$.

Example 7

9-[(N-(Carboxymethyl)-N-(2-phosphonoethyl))-2-aminoethyl]guanine

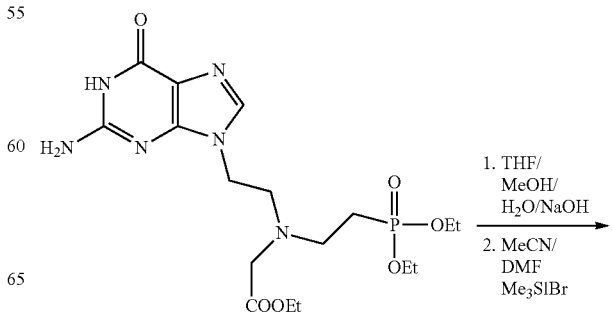

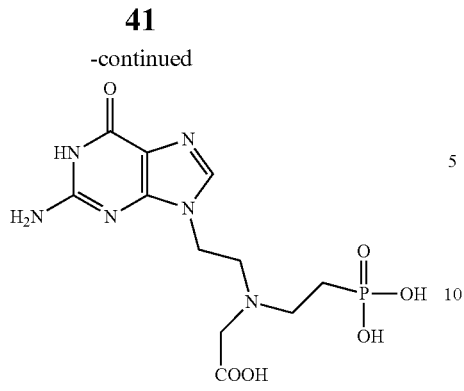

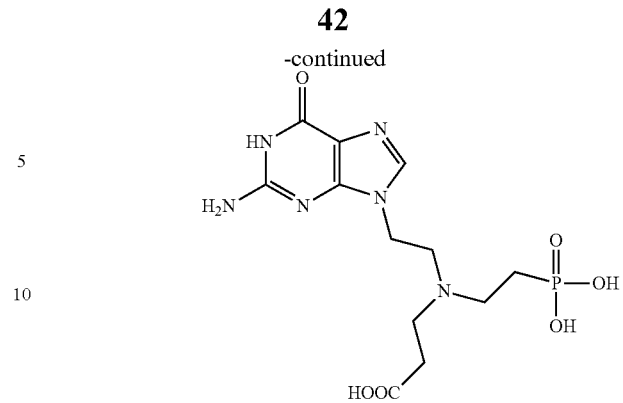

A mixture of diethyl 9-[(N-(2-ethoxy-2-oxoethyl)-N-(2-phosphonoethyl))-2-aminoethyl]guanine (intermediate from Example 1, 0.44 g, 1 mmol), tetrahydrofuran (10 ml), methanol (10 ml) and aqueous NaOH (10 M, 0.2 ml) was refluxed for 2 h and then stirred at room temperature overnight. After evaporation and codistillation with toluene/ethanol and acetonitrile, the residue was dissolved in acetonitrile (20 ml) and dimethylformamide (8 ml). 2,6-Lutidine (0.1 ml) and BrSiMe$_3$ (1 ml) were added and the mixture was stirred for 2 days at room temperature. After evaporation and codistillation with acetonitrile, the residue was treated with aqueous methanol (2:1, 30 ml) for 1 h, evaporated and codistilled with water. The residue was purified by preparative HPLC (water-methanol). 9-[(N-(Carboxymethyl)-N-(2-phosphonoethyl))-2-aminoethyl]guanine was obtained as white solid in 54% yield (0.19 g). $^1$H NMR (DMSO-d$_6$): 10.58 s, 1 H (NH); 7.73 s, 1 H (H-8); 6.46 s, 2 H (NH$_2$); 4.00 t, 2 H, =6.1 (H-1'); 3.34 s, 2 H (H-5'); 2.93 t, 2 H, J(2',1')=6.1 (H-2'); 2.84 dd, 2 H, J=8.1 and 16.1 (H-3'); 1.61 m, 2 H (H-4'); 1.17 t, 3 H, J=7.1 (Et). $^{13}$C NMR (DMSO-d$_6$): 172.13 (CO); 156.70 (C-6); 153.43 (C-2); 151.00 (C-4); 137.88 (C-8); 116.06 (C-5); 54.01, 52.51 and 48.18 (C-2', C-5' and C-3'); 40.78 (C-1'); 25.97, J(P,C)=133.6 (C-4'). Anal. Calcd for C$_{11}$H$_{17}$N$_6$O$_6$P.3/2H$_2$O: C, 34.11; H, 5.21; N, 21.70. Found: C, 33.82; H, 5.19; N, 21.29. MS (ESI−): m/z=359 [M−H]$^-$.

Example 8

9-[(N-(2-Carboxyethyl)-N-(2-phosphonoethyl))-2-aminoethyl]guanine

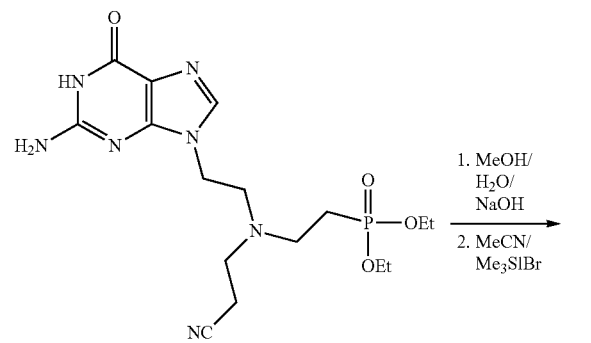

A mixture of diethyl 9-[(N-(2-cyanoethyl)-N-(2-phosphonoethyl))-2-aminoethyl]guanine (intermediate from Example 5, 0.41 g, 1 mmol), methanol (15 ml) and aqueous NaOH (25%, 3 ml) was refluxed for 4 h and then stirred at room temperature overnight. After evaporation and codistillation with toluene/ethanol and acetonitrile, the residue was dissolved in acetonitrile (20 ml). 2,6-Lutidine (0.1 ml) and BrSiMe$_3$ (1 ml) were added and the mixture stirred for 2 days at room temperature. After evaporation and codistillation with acetonitrile, the residue was treated with aqueous methanol (2:1, 30 ml) for 1 h and evaporated. The residue was purified by preparative HPLC (water-methanol), yield 45% (0.16 g), white solid. $^1$H NMR (D$_2$O): 7.64 s, 1 H (H-8); 4.73 t, 2 H, J(1',2')=6.0 (H-1'); 3.84 t, 2 H, J(2',1')=6.0 (H-2'); 3.62 t, J(5',6')=6.5, 2 H (H-5'); 3.58 m, 2 H (H-3'); 2.92 t, 2 H, J(6',5')=6.5 (H-6'); 2.08 m, 2 H (H-4'). $^{13}$C NMR (DMSO-d$_6$): $^{13}$C NMR (D$_2$O): 174.21 (CO); 156.44 (C-6); 155.32 (C-2); 151.01 (C-4); 138.57 (C-8); 116.21 (C-5); 51.80, 50.29 and 49.72 (C-2', C-3' and C-5'); 40.29 (C-1'); 28.54 (C-6'); 22.62 d, J(P,C)=129.3 (C-4'). Anal. Calcd. for C$_{12}$H$_{19}$N$_6$O$_6$P.4/3H$_2$O: C, 36.18; H, 5.48; N, 21.10. Found: C, 36.41; H, 5.23; N, 20.86. MS (ESI−): m/z=373 [M−H]$^-$.

Example 9

9-[(N-(Carboxypropyl)-N-(2-phosphonoethyl))-2-aminoethyl]guanine

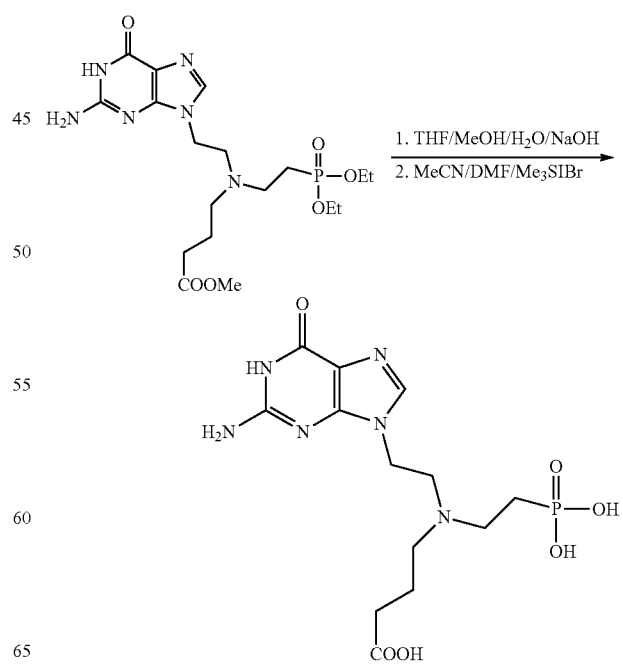

A mixture of diethyl 9-[(N-(4-methoxy-4-oxobutyl)-N-(2-phosphonoethyl))-2-aminoethyl]guanine (intermediate from Example 3, 0.46 g, 1 mmol), tetrahydrofuran (10 ml), methanol (10 ml) and aqueous NaOH (10 M. 0.2 ml) was refluxed for 2 h and then stirred at room temperature overnight., After evaporation and codistillation with toluene/ethanol and acetonitrile, the residue was dissolved in acetonitrile (20 ml) and dimethylformamide (8 ml). 2,6-Lutidine (0.1 ml) and BrSiMe$_3$ (1 ml) were added and the mixture was stirred for 2 days at room temperature. After evaporation and codistillation with acetonitrile, the residue was treated with aqueous methanol (2:1, 30 ml) for 1 h, evaporated and codistilled with water. The residue was purified by preparative HPLC (water-methanol). 9-[(N-(Carboxymethyl)-N-(2-phosphonoethyl))-2-aminoethyl]guanine was obtained as white solid in 58% yield (0.23 g). NMR (DMSO-d$_6$): 10.61 s, 1 H (NH); 7.68 s, 1 H (H-8); 6.54 s, 2 H (NH$_2$); 4.08 t, 2 H, J(1',2')=5.8 (H-1'); 2.95 t, 2 H, J(2',1')=5.8 (H-2'); 2.89 m, 2 H (H-3'); 2.63 t, 2 H, J(5',6')=7.0 (H-5'); 2.17 t, 2 H, J(7',6')=7.2 (H-7'); 1.68 m, 2 H (H-4'), 1.60 m, 2 H (H-6'). $^{13}$C NMR (DMSO-d$_6$): 174.08 (CO); 156.64 (C-6); 153.42 (C-2); 1'51.00 (C-4); 137.53 (C-8); 116.27 (C-5); 51.78, 51.50 and 47.85 (C-2', C-3' and C-5'); 39.99 (C-1'); 30.87 (C-7'); 24.30 d, J(P,C)=132.91 (C-4'), 20.96 (C-6'). Anal. Calcd for C$_{13}$H$_{21}$N$_6$O$_6$P.H$_2$O: C, 38.43; H, 5.71; N, 20.68. Found: C, 38.51; H, 5.64; N, 20.53. MS (ESI−): m/z=387 [M−H]−.

Example 10

9-[(N-(2-Hydroxyethyl)-N-(2-phosphonoethyl))-2-aminoethyl]guanine

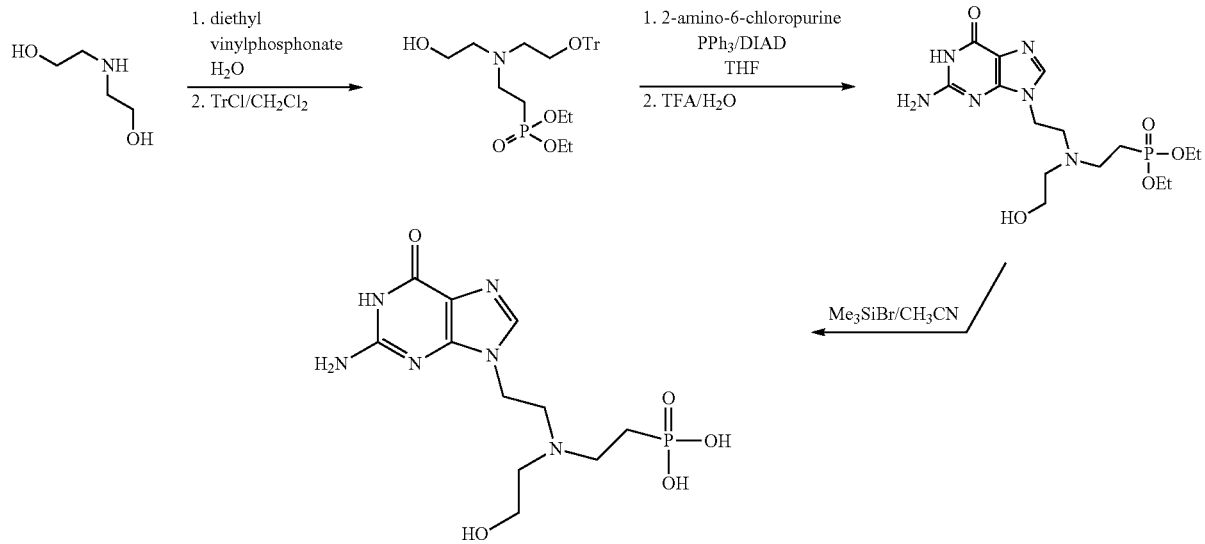

The mixture of diethanolamine (2.1 g, 20 mmol), H$_2$O (50 ml) and diethyl vinylphosphonate (3.3 g, 20 mmol) was stirred at room temperature overnight. The solvent was evaporated and the residue codistilled with ethanol. The residue was purified by chromatography on silica gel (CHCl$_3$-MeOH) to obtain diethyl 2-(bis(2-hydroxyethyl)amino)ethylphosphonate, yield 5.03 g (93%). This intermediate (3.4 g, 12.6 mmol) was dissolved in CH$_2$Cl$_2$ (50 ml), a catalytic amount of dimethylaminopyridine was added followed by Et$_3$N (1.2 ml) and then tritylchloride (3.5 g, 14.5 mmol) dissolved in CH$_2$Cl$_2$ (30 ml) was added drop-wise. The reaction mixture was stirred overnight at room temperature and solvent evaporated. The residue was purified by column chromatography on silica gel (CHCl$_3$-MeOH) to afford diethyl 2((2-hydroxyethyl)(2-(trityloxy)ethyl)amino)ethylphosphonate as yellowish oil (6.01 g, 93%). To a solution of triphenylphosphine (6.3 g, 24 mmol) in dry THF (100 ml) cooled to −30° C. under argon atmosphere diisopropylazadicarboxylate (DIAD, 4.4 ml, 23 mmol) was added slowly. The mixture was stirred for 30 minutes and this preformed complex was added to 2-amino-6-chloropurine (3.8 g, 22.6 mmol), dry THF (70 ml) and diethyl 2-((2-hydroxyethyl)(2-(trityloxy)ethyl)amino)ethylphosphonate (5.72 g, 11.2 mmol) at −30° C. under argon. The resulting mixture was slowly warmed to room temperature and stirred for 48 h. Then water (30 ml) was added and the mixture was heated at 80° C. for 30 h. Solvent was evaporated the residue was codistilled with toluene or ethanol and the crude mixture purified by chromatography on silica gel (MeOH—CHCl$_3$). This intermediate was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) the diethyl 9-[(N-(2-hydroxyethyl)-N-(2-phosphonoethyl))-2-aminoethyl]guanine was obtained in 50% yield (2.25 g).

A mixture of this diethyl ester (0.80 g, 2 mmol), acetonitrile. (20 ml), dimethylformamide (14 ml), 2,6-lutidine (0.1 ml) and BrSiMe$_3$ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N-(2-Hydroxyethyl)-N-(2-phosphonoethyl))-2-aminoethyl]guanine was obtained as a white solid in 62% yield (0.43 g). $^1$H NMR (DMSO-d$_6$): 10.74 s, 1 H (NH); 7.75 s, 1 H (H-8); 6.62 s, 2 H (NH$_2$); 4.27 t, 2 H, J(1',2')=6.2 (H-1'); 3.64 t, 2 H, J(6',5')=5,4 (H-6'); 3.38 t, 2 H, J(2',1')=6.2 (H-2'); 3.27 m, 2 H(H-3'); 3.11 t. 2 H, J=5.4 (H-5'); 1.90 m, 2 H (H-4'). $^{13}$C NMR (DMSO-d$_6$): 157.01 (C-6); 153.95 (C-2); 151.26 (C-4); 137.87 (C-8); 116.58 (C-5); 56.29 (C-6'), 54.62, 51.98 and 59.11 (C-5', C-2' and C-3'); 38.89 (C-1'); 23.64 d, J(P,C)=130.8 (C-4'). Anal. Calcd for C$_{11}$H$_{19}$N$_6$O$_5$P.H$_2$O: C, 36.27; H, 5.81; N, 23.07. Found: C, 35.99; H, 5.65; N. 22.72. MS (ESI−): m/z=345 [M−H]−.

Example 11

9-[(N,N-(Bis-2-phosphonoethyl))-2-aminoethyl]guanine

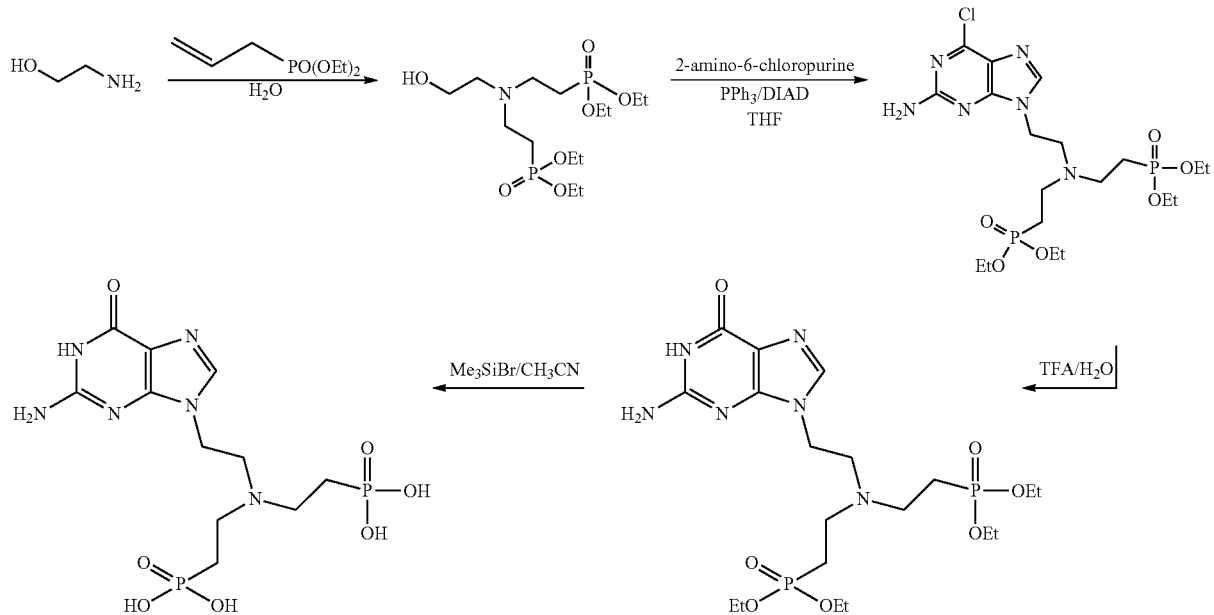

The mixture of 2-aminoethanol (3.57 g, 58 mmol), H₂O (80 ml) and diethyl vinylphosphonate (19.7 g, 120 mmol) was stirred for 2 days at roomtemperature. Solvent was evaporated and the residue codistilled with ethanol. The resulting tetraethyl 2,2'-(2-hydroxyethylazanediyl)bis(ethane-2,1-diyl)diphosphonate was purified by chromatography on silica gel (CHCl₃-MeOH).

To a solution of triphenylphosphine (6.3 g, 24 mmol) in dry THF (100 ml) cooled to −30° C. under argon atmosphere diisopropylazadicarboxylate (DIAD, 4.4 ml, 23 mmol) was added slowly. The mixture was stirred for 30 minutes and this preformed complex was added to 2-amino-6-chloropurine (3.8 g, 22.6 mmol), dry THF (70 ml) and tetraethyl 2,2'-(2-hydroxyethylazanediyl)bis(ethane-2,1-diyl)diphosphonate (4.3 g, 11.2 mmol) at −30° C. under argon. The resulting mixture was slowly warmed to room temperature and stirred for 48 h. Then water (30 ml) was added and the mixture was heated at 80° C. for 30 h. Solvent was evaporated the residue was codistilled with toluene or ethanol and the crude mixture purified by chromatography on silica gel (MeOH—CHCl₃). Tetraethyl 9-[(N,N-(bis-2-phosphonoethyl))-2-aminoethyl]-2-amino-6-chloropurine was isolated in 79% yield (4.79 g).

This intermediate (2.16 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—CHCl₃) tetraethyl 9-[(N,N-(bis-2-phosphonoethyl))-2-aminoethyl]guanine was obtained in 85% yield (1.77 g).

A mixture of this tetraethyl ester (1.04 g, 2 mmol), acetonitrile (20 ml), dimethylformamide (6 ml), 2,6-lutidine (0.1 ml) and BrSiMe₃ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N,N-(Bis-2-phosphonoethyl))-2-aminoethyl]guanine was obtained as a white solid in 51% yield (0.42 g).

¹H NMR (DMSO-d₆): 8.36 s, 1 H (H-8); 7.98 s, 4.62 t, 2H, J(1',2') 6.0 (H-1'); 3.73 t, 2 H, J(2',1')=6.3 (H-2'); 3.52 dd, 4 H, J=8.2 and 16.4 (H-3' and H-5'); 2.02 m, 4 H (H-4' and H-6'). ¹³C NMR (DMSO-d₆): 156.74 (C-6); 155.08 (C-2); 151.22 (C-4); 138.5 (C-8); 116.32 (C-5); 51.21 (C-2'); 49.44, 2C (C-3' and C-5'); 39.56 (C-1'); 22.78 d, 2C. J(P,C)=129.41 (C-4' and C-6'). Anal. Calcd for C₁₅H₂₃N₆O₄P.2H₂O: C, 29.60; H, 5.42; N, 18.83. Found: C, 29.36; H, 5.37; N, 19.14. MS (ESI−): m/z=409 [M−H]⁻.

Example 12

9-[(N-(2-Phosphonoethyl))-2-aminoethyl]guanine

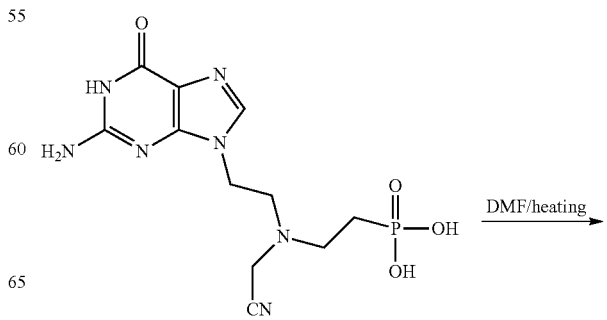

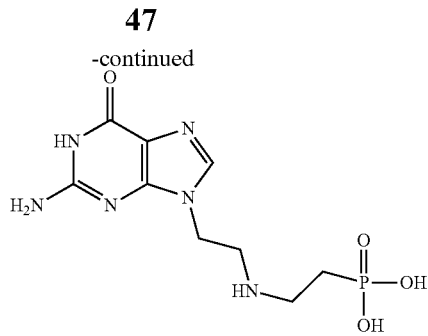

9-[(N-(2-Cyanomethyl)-N-(2-phosphonoethyl))-2-aminoethyl]guanine (Example 4, 170 mg, 0.5 mmol) in dimethylformamide (10 ml) was heated at 120° C. for 3 days. The solvent was then evaporated and the residue codistilled with toluene. The residue was purified by preparative HPLC (water-methanol), yield 30% (45 mg). $^1$H NMR (D$_2$O+NaOD): 7.59 s, 1 H (H-8); 4.05 t, 2 H, J(1',2')=6.3 (H-1'); 2.88 t, 2 H, J(2',1')=6.3 (H-2'); 2.66 dd, 2 H, J=7.2 and 16.3 (H-3'); 1.470 m, 2 H (H-4'). $^{13}$C NMR (D$_2$O+NaOD): 168.68 (C-6); 161.54 (C-2); 151.81 (C-4); 138.94 (C-8); 117.99 (C-5); 47.63, 45.02 and 43.25 (C-2', C-3' and C-1'); 29.82 d, J(P,C)=127.6 (C-4'). Anal. Calcd for $C_{13}H_{21}N_6O_6P.H_2O$: C, 38.43; H, 5.71; N, 20.68. Found: C, 38.51; H, 5.64; N, 20.53. HRMS calcd. for $C_9H_{14}N_6O_4P$: 301.08196; found: 301.08196. MS (ESI–): m/z=301 [M–H]$^-$.

Example 13

9-[(N-(2-Phosphonomethoxyethyl)-N-(2-phosphonoethyl))-2-aminoethyl]guanine

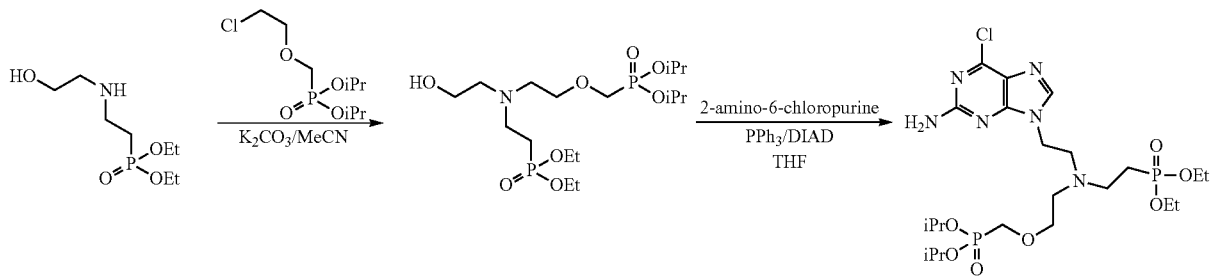

The mixture of diethyl 2-(2-hydroxyethylamino)ethylphosphonate (6 g, 26.7 mmol), KI (0.2 g) and K$_2$CO$_3$ (3.7 g, 26.7 mmol) in dry acetonitrile (80 ml) diisopropyl (2-chloroethoxy)methylphosphonate (7.77 g, 30 mmol) was added. The reaction mixture was heated at 80° C. for 70 h. The solvent was then removed by evaporatation. Water and CHCl$_3$ were added, the organic layer separated, washed with brine and dried over anhydrous MgSO$_4$. After filtration, solvent was evaporated and the residue was purified by column chromatography on silica gel (CHCl$_3$-MeOH), the diethyl diisopropyl (2-((N-hydroxyethyl)(N-2-phosphonomethoxyethyl)amino)ethylphosphonate was obtained in 45% yield (5.37 g).

To a solution of triphenylphosphine (6.3 g, 24 mmol) in dry THF (100 ml) cooled to –30° C. under argon atmosphere diisopropylazadicarboxylate (DIAD, 4.4 ml, 23 mmol) was added slowly. The mixture was stirred for 30 minutes and this preformed complex was added to 2-amino-6-chloropurine (3.8 g, 22.6 mmol), dry THF (70 ml) and diethyl diisopropyl (2-((N-hydroxyethyl)(N-2-phosphonomethoxyethyl)amino) ethylphosphonate (4.65 g, 11.2 mmol) at –30° C. under argon. The resulting mixture was slowly warmed to room temperature and stirred for 48 h. Then water (30 ml) was added and the mixture was heated at 80° C. for 30 h. Solvent was evaporated the residue was codistilled with toluene or ethanol and the crude mixture purified by chromatography on silica gel (MeOH—CHCl$_3$). Diethyl diisopropyl 9-[(N-(2-phosphonomethoxyethyl)-N-(2-phosphonoethyl))-2-aminoethyl]-2-amino-6-chloropurine was isolated in 65% yield (4.36 g).

This intermediate (2.40 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) diethyl diisopropyl 9-[(N-(2-phosphonomethoxyethyl)-N-(2-phosphonoethyl))-2-aminoethyl]guanine was obtained in 97% yield (2.25 g).

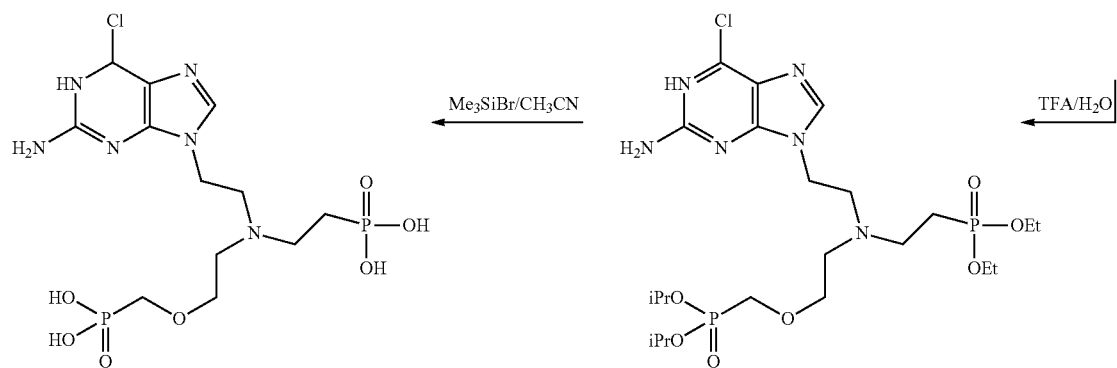

A mixture of this diethyl diisopropylester (1.16 g, 2 mmol), acetonitrile (20 ml) and BrSiMe$_3$ (3 ml) was stirred for 3 days at room temperature. After evaporation and codistillation with acetonitrile, the residue was treated with aqueous methanol (2:1, 30 ml) for 1 h and evaporated. The residue was purified by preparative HPLC. 9-[(N-(2-Phosphonomethoxyethyl)-N-(2-phosphonoethyl))-2-aminoethyl]guanine was obtained as a white foam in 48% yield (0.42 g).

$^1$H NMR (D$_2$O): 8.66 s, 1 H (H-8); 4.68 t, 2 H, J(1',2')=6.4 (H-1'); 3.92 t, 2 H, J(6',5')=5.0 (H-6'); 3.83 t, 2 H, J(2',1')=6.4 (H-2'); 3.67 d, 2 H, J=8.8 (H-7'); 3.57 m, 4 H (H-3' and H-5'); 2.08 m, 2 H (H-4'). $^{13}$C NMR (D$_2$O): 155.07 (C-6); 154.06 (C-2); 149.60 (C-4); 137.24 (C-8); 117.24 (C-5); 65.92 d, J(P,C)=164.3 (C-7'); 64.80 (C-6'); 52.35, 49.80 and 49.15 (C-2', C-3' and C-5'); 38.73 (C-1'); 21.28 d, J(P,C)=123.04 (C-4'). HRMS calcd. for C$_{12}$H$_{21}$N$_6$O$_6$P$_2$: 439.09016; found: 439.09026. MS (ESI): m/z=439 [M–H]$^-$.

Example 14

9[(N-(Phosphonoethyl)-N-(2-phosphonomethyl))-2-aminoethyl]guanine

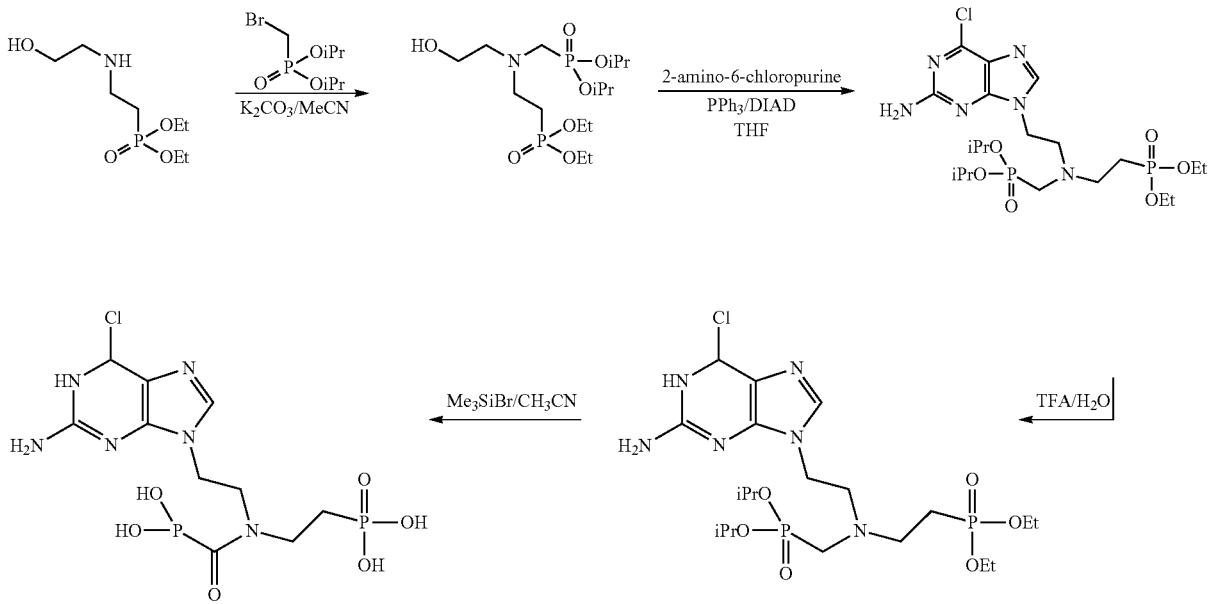

The mixture of diethyl 2-(2-hydroxyethylamino)ethylphosphonate (6 g, 26.7 mmol), KI (0.2 g) and K$_2$CO$_3$ (3.7 g, 26.7 mmol) in dry acetonitrile (80 ml) diisopropyl bromomethylphosphonate (7.77 g, 30 mmol) was added. The reaction mixture was heated at 80° C. for 90 h. The solvent was then removed by evaporatation. Water and CHCl$_3$ were added, the organic layer separated, washed with brine and dried over anhydrous MgSO$_4$. After filtration, solvent was evaporated and the residue was purified by column chromatography on silica gel (CHCl$_3$-MeOH), the diethyl diisopropyl 2-((N-hydroxyethyl)(N-phosphonomethyl)amino)ethylphosphonate was obtained in 61% yield (6.56 g).

To a solution of triphenylphosphine (6.3 g, 24 mmol) in dry THF (100 ml) cooled to –30° C. under argon atmosphere diisopropylazadicarboxylate (DIAD, 4.4 ml, 23 mmol) was added slowly. The mixture was stirred for 30 minutes and this preformed complex was added to 2-amino-6-chloropurine (3.8 g, 22.6 mmol), dry THF (70 ml) and diethyl diisopropyl 2((N-hydroxyethyl)(N-phosphonomethypamino)ethylphosphonate (4.51 g, 11.2 mmol) at –30° C. under argon. The resulting mixture was slowly warmed to room temperature and stirred for 48 h. Then water (30 ml) was added and the mixture was heated at 80° C. for 30 h. Solvent was evaporated the residue was codistilled with toluene or ethanol and the crude mixture purified by chromatography on silica gel (MeOH—CHCl$_3$). Diethyl diisopropyl 9-[(N-(2-phosphonoethyl)-N-(2-phosphonomethyl))-2-aminoethyl]-2-amino-6-chloropurine was isolated in 75% yield (4.66 g).

This intermediate (2.22 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) diethyl diisopropyl 9-[(N-(2-phosphonoethyl)-N-(2-phosphonomethyl))-2-aminoethyl]guanine was obtained in 97% yield (2.08 g).

A mixture of this diethyl diisopropylester (1.07 g, 2 mmol), acetonitrile (20 ml) and BrSiMe$_3$ (3 ml) was stirred for 3 days at room temperature. After evaporation and codistillation with acetonitrile, the residue was treated with aqueous methanol (2:1, 30 ml) for 1 h and evaporated. The residue was purified by preparative HPLC. 9-[(N-(2-Phosphonoethyl)-N-(2-phosphonomethyl))-2-aminoethyl]guanine was obtained as a white foam in 71% yield (0.56 g).

$^1$H NMR (DMSO-d$_6$): 11.53 (NH); 9.04 s, 1 H (H-8); 7.30 (NH$_2$); 4.51 t, 2 H, J(1',2')=6.0 (H-1'); 3.63 t, 2 H, J(2',1')=6.0 (H-2'); 3.50 m, 4 H(H-3' and H-5'); 2.03 in, 2 H (H-4'). $^{13}$C NMR (DMSO-d$_6$): 155.13 (C-6); 153.72 (C-2); 149.66 (C-4); 137.63 (C-8); 115.98 (C-5); 53.91 and 50.01 (C-2' and C-3'); 48.64 d, J(P,C)=146.2 (C-5'); 40.34 (C-1'); 23.06 d, J(P,C)=132.45 (C-4'). HRMS calcd. for C$_{10}$H$_{17}$N$_6$O$_7$P$_2$: 395.06394; found: 395.06342. MS (ESI): m/z=395 [M–H]$^-$.

Example 15

9-[(N-(2-Ethoxy-2-oxoethyl)-N-(2-phosphonoethyl))-2-aminoethyl]hypoxanthine

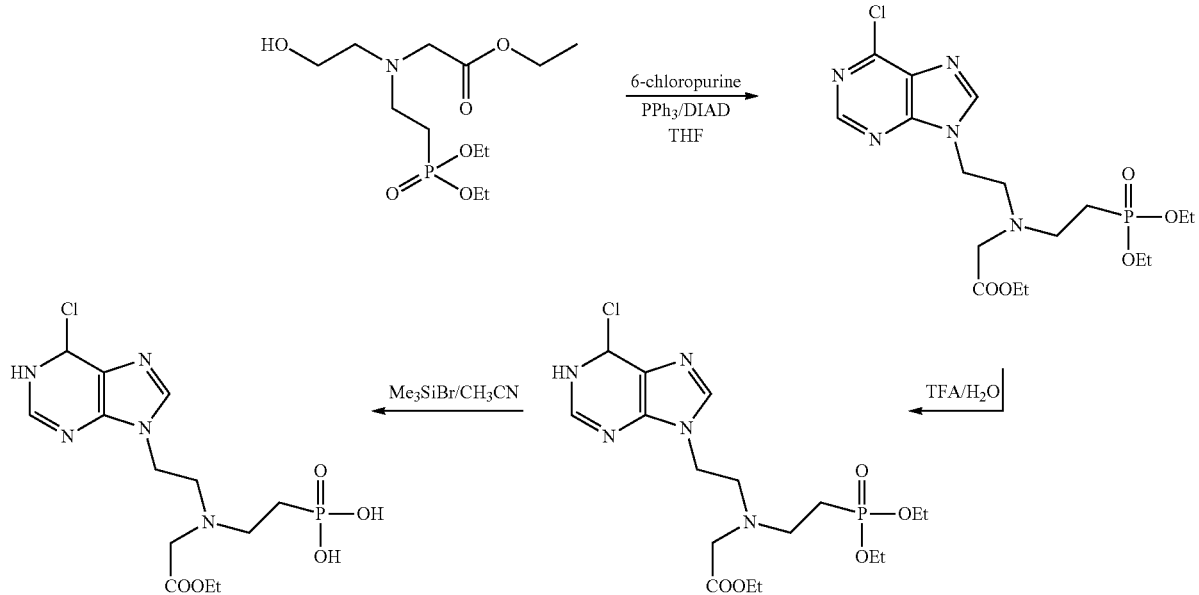

To a solution of triphenylphosphine (6.3 g, 24 mmol) in dry THF (100 ml) cooled to −30° C. under argon atmosphere diisopropylazadicarboxylate (DIAD, 4.4 ml, 23 mmol) was added slowly. The mixture was stirred for 30 minutes and this preformed complex was added to 6-chloropurine (3.5 g, 22.6 mmol), dry THF (70 ml) and ethyl 2-((2-(diethoxyphosphoryl)ethyl)(2-hydroxyethyl)amino)acetate (see Example 1, 3.5 g, 11.2 mmol) at −30° C. under argon. The resulting mixture was slowly warmed to room temperature and stirred for 48 h. Solvent was evaporated and the crude mixture purified by chromatography on silica gel (MeOH—CHCl$_3$). Diethyl 9-[(N-(2-ethoxy-2-oxoethyl)-N-(2-phosphonoethyl))-2-aminoethyl]-6-chloropurine was isolated in 79% yield (3.97 g).

This intermediate (1.79 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) diethyl 9-[(N-(2-ethoxy-2-oxoethyl)-N-(2-phosphonoethyl))-2-aminoethyl]hypoxanthine was obtained in 75% yield (1.29 g).

A mixture of this diethyl ester (0.86 g, 2 mmol), acetonitrile (20 ml). 2.6-lutidine (0.1 ml) and BrSiMe$_3$ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N-(2-Ethoxy-2-oxoethyl)-N-(2-phosphonoethyl))-2-aminoethyl]hypoxanthine was obtained as a white solid in 39% yield (0.29 g).
$^1$H NMR (DMSO-d$_6$): 12.26 s, 1 H (NH); 8.08 s, 1 H and 8.02 s, 1 H (H-2 and H-8); 4.17 t, 2 H, J(1′,2′)=6.0 (H-1′); 4.03 q, 2 H, J=7.1 (Et); 3.34 s, 2 H (H-5′); 2.94 t, 2 H, =6.0 (H-2′); 2.76 m, 2 H (H-3′); 1.48 m, 2 H (H-4′); 1.16 t, 3 H, J=7.1 (Et).
$^{13}$C NMR (DMSO-d$_6$): 170.78 (CO); 156.61 (C-6); 148.30 (C-4); 145.21 (C-2); 140.71 (C-8); 123.60 (C-5); 59.77 (Et); 53.79, 52.16 and 48.34 (C-2′, C-5′ and C-3′); 41.50 (C-1′); 14.02 (Et). Anal. Calcd for C$_{13}$H$_{20}$N$_5$O$_6$P.1/2MeOH: C, 41.65; H, 5.70; N, 17.99. Found: C, 41.53; H, 5.45; N, 17.78. MS (ESI−): m/z=372 [M−H]$^-$.

Example 16

9-[(N-(3-Methoxy-3-oxopropyl)-N-(2-phosphonoethyl))-2-aminoethyl]hypoxanthine

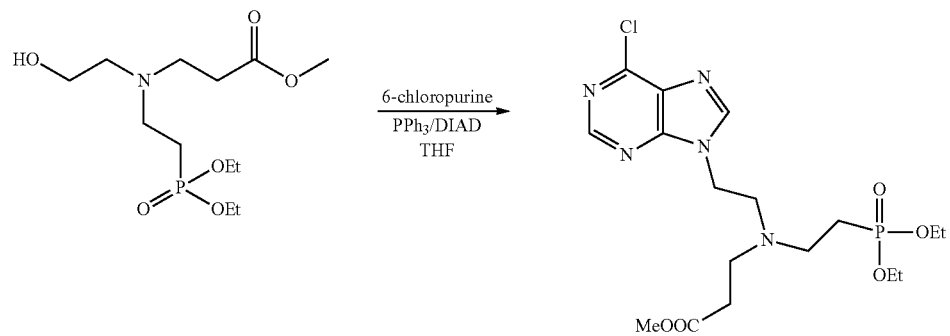

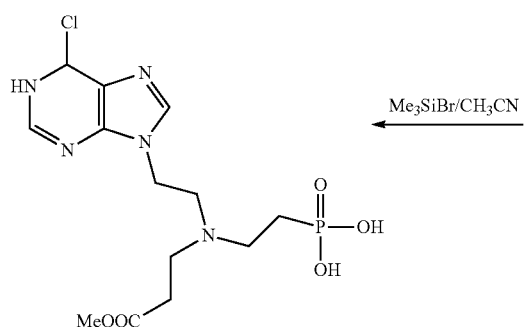 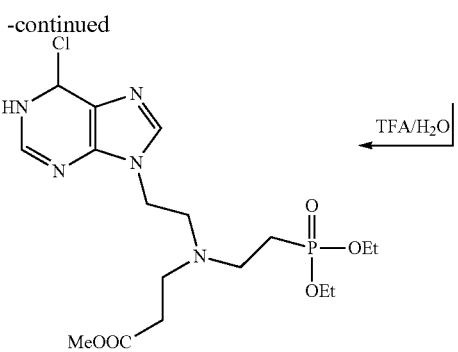

To a solution of triphenylphosphine (6.3 g, 24 mmol) in dry THF (100 ml) cooled to −30° C. under argon atmosphere diisopropylazadicarboxylate (DIAD, 4.4 ml, 23 mmol) was added slowly. The mixture was stirred for 30 minutes and this preformed complex was added to 6-chloropurine (3.5 g, 22.6 mmol), dry THF (70 ml) and 34(2-(diethoxyphosphoryl)ethyl)(2-hydroxyethyl)amino)propanoate (see Example 2, 3.5 g, 11.2 mmol) at −30° C. under argon. The resulting mixture was slowly warmed to room temperature and stirred for 48 h. Solvent was evaporated and the crude mixture purified by chromatography on silica gel (MeOH—CHCl$_3$). Diethyl 9-[(N-(3-methoxy-3-oxopropyl)-N-(2-phosphonoethyl))-2-aminoethyl]-6-chloropurine was isolated in 56% yield (2.81 g).

This intermediate (1.79 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) diethyl 9-[(N-(3-methoxy-3-oxopropyl)-N-(2-phosphonoethyl))-2-aminoethyl]hypoxanthine was obtained in 66% yield (1.13 g).

A mixture of this diethyl ester (0.86 g, 2 mmol), acetonitrile (20 ml), 2,6-lutidine (0.1 nil) and BrSiMe$_3$ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N-(3-Methoxy-3-oxopropyl)-N-(2-phosphonoethyl))-2-aminoethyl] hypoxanthine was obtained as a white foam in 60% yield (0.45 g). $^1$H NMR (DMSO-d$_6$): 12.29 s, 1 H (NH); 8.05 s, 1 H and 8.04 s, 1 H (H-2 and H-8); 4.26 t, 2 H, J(1',2')=6.1 (H-1'); 3.54 s, 3 H (Me); 2.97 t, 2 H, J(2',1')=6.1 (H-2'); 2.86 t, 2 H, J(5',6')=6.8 (11-5'); 2.81 m, 2 H (H-3'); 2.42 t, 2 H, J(6',5')=6.8 (H-6'); 1.67 m, 2 H (H-4'). $^{13}$C NMR (DMSO-d$_6$): 171.68 (CO); 156.51 (C-6); 148.21 (C-4); 145.29 (C-2); 140.47 (C-8); 123.72 (C-5); 51.24 (Me); 51.61, 48.02 and 47.48 (C-2', C-5' and C-3'); 40.64 (C-1'); 30.89 (C-6'); 24.16 d, J(P,C)=132.2 (C-4'). Anal. Calcd for C$_{13}$H$_{20}$N$_5$O$_6$P.3/2H$_2$O: C, 39.00; H, 5.79; N, 17.49. Found: C, 39.00; H, 5.50; N, 17.57. MS (ESI–): m/z=372 [M−H]$^-$.

Example 17

9-[(N-(4-Methoxy-4-oxobutyl)-N-(2-phosphonoethyl))-2-aminoethyl] hypoxanthine

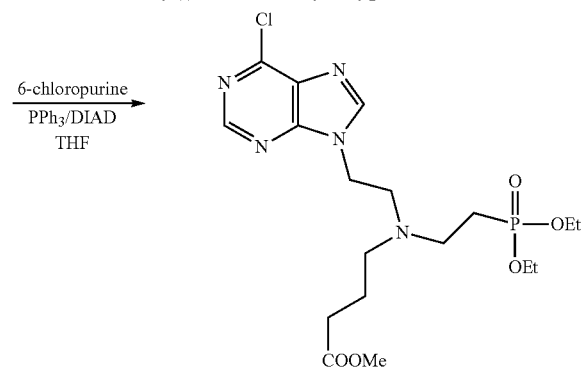

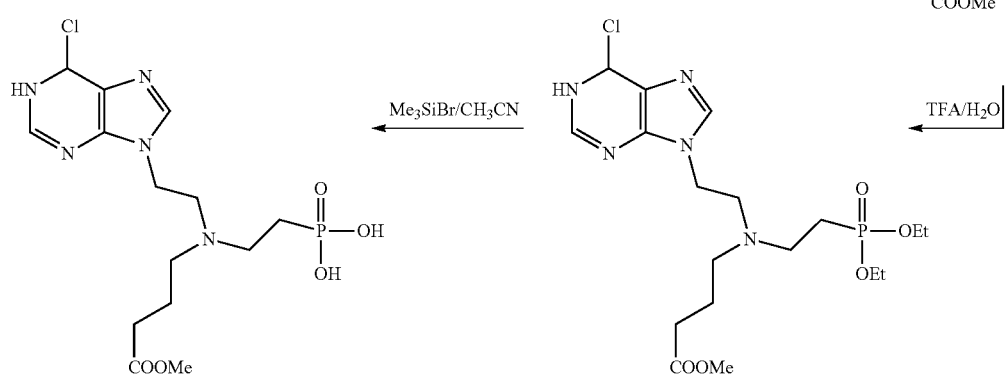

To a solution of triphenylphosphine (6.3 g, 24 mmol) in dry THF (100 ml) cooled to −30° C. under argon atmosphere diisopropylazadicarboxylate (DIAD, 4.4 ml. 23 mmol) was added slowly. The mixture was stirred for 30 minutes and this preformed complex was added to 6-chloropurine (3.5 g, 22.6 mmol), dry THF (70 ml) and methyl 3-((2-(diethoxyphosphoryl)ethyl)(2-hydroxyethyl)amino)butanoate (see Example 3, 3.64 g, 11.2 mmol) at −30° C. under argon. The resulting mixture was slowly warmed to room temperature and stirred for 48 h. Solvent was evaporated and the crude mixture purified by chromatography on silica gel (MeOH—CHCl$_3$). Diethyl 9-[(N-(4-methoxy-4-oxobutyl)-N-(2-phosphonoethyl))-2-aminoethyl]-6-chloropurine was isolated in 83% yield (4.29 g).

This intermediate (1.85 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) diethyl 9-[(N-(4-methoxy-4-oxobutyl)-N-(2-phosphonoethyl))-2-aminoethyl]hypoxanthine was obtained in 62% yield (1.1 g).

A mixture of this diethyl ester (0.89 g, 2 mmol), acetonitrile (20 ml), 2,6-lutidine (0.1 ml) and BrSiMe$_3$ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N-(4-Methoxy-4-oxobutyl)-N-(2-phosphonoethyl))-2-aminoethyl]hypoxanthine was obtained as a white solid in 41% yield (0.32 g). $^1$H NMR (DMSO-d$_6$): 12.30 s, 1 H (NH); 8.08 s, 1 H and 8.03 s, 1 H (H-2 and H-8); 4.26 m, 2 H, (H-1'); 3.55 s, 3 H (Me); 2.96 m, 2 H (H-2'); 2.82 m, 2 H (H-5'); 2.55 m. 2 H (H-3'); 2.14 t, 2 H, J(7',6')=6.8 (H-7'); 1.65 m, 2 H (H-4'); 1.53 m, 2 H (H-6'). $^{13}$C NMR (DMSO-d$_6$): 172.93 (CO); 156.50 (C-6); 148.23 (C-4); 145.26 (C-2); 140.50 (C-8); 123.76 (C-5); 51.07 (Me); 51.58, 51.31 and 47.57 (C-2', C-5' and C-3'); 40.82 (C-1'); 30.32 (C-7'); 24.19 d, J(P,C)=129.4 (C-4'); 21.16 (C-6'). Anal. Calcd for C$_{14}$H$_{22}$N$_5$O$_6$P.H$_2$O: C, 41.48; H, 5.97; N, 17.28. Found: C, 41.79; H, 5.81; N, 17.04. MS (ESI−): m/z=386 [M−H]$^-$.

Example 18

9-[(N-(2-Cyanomethyl)-N-(2-phosphonoethyl))-2-aminoethyl]hypoxanthine

To a solution of triphenylphosphine (6.3 g, 24 mmol) in dry THF (100 ml) cooled to −30° C. under argon atmosphere diisopropylazadicarboxylate (DIAD, 4.4 ml, 23 mmol) was added slowly. The mixture was stirred for 30 minutes and this preformed complex was added to 6-chloropurine (3.5 g, 22.6 mmol), dry THF (70 ml) and diethyl 2-(2-cyanomethylamino)ethylphosphonate (2.96 g, 11.2 mmol) at −30° C. under argon. The resulting mixture was slowly warmed to room temperature and stirred for 48 h. Solvent was evaporated and the crude mixture purified by chromatography on silica gel (MeOH—CHCl$_3$). Diethyl 9-[(N-(2-cyanomethyl)-N-(2-phosphonoethyl))-2-aminoethyl]-6-chloropurine was isolated in 87% yield (3.91 g).

This intermediate (1.60 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) diethyl 9-[(N-(2-cyanomethyl)-N-(2-phosphonoethyl))-2-aminoethyl]hypoxanthine was obtained in 95% yield (1.45 g).

A mixture of this diethyl ester (0.76 g, 2 mmol), acetonitrile (20 ml), dimethylformamide (2 ml), 2,6-lutidine (0.1 ml) and BrSiMe$_3$ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N-(2-Cyanomethyl)-N-(2-phosphonoethyl))-2-aminoethyl]hypoxanthine was obtained as a white solid in 59% yield (0.38 g). $^1$H NMR (DMSO-d$_6$): 12.29 s, 1 H (NH); 8.06 s, 1 H and 8.03 s, 1 H (H-2 and H-8); 4.25 t, 2 H, J(1',2')=5.7 (H-1'); 3.83 s, 2 H (H-5'); 2.85 t, 2 H, J(2',1')=5.7 (H-2'); 2.66 dd, 2 H, J=7.5 and 15.8 (H-3'); 1.52 m, 2 H (H-4'). $^{13}$C NMR (DMSO-d$_6$): 156.51 (C-6); 148.28 (C-4); 145.27 (C-2); 140.44 (C-8); 123.59 (C-5); 116.11 (CN); 52.07 and 48.33 (C-2' and C-3'); 41.22 and 40.82 (C-5' and C-1'); 24.83 d. J(P,C)=134.1 (C-4'). Anal. Calcd for C$_{11}$H$_{15}$N$_6$O$_4$P.2/3H$_2$O: C, 39.06; H, 4.87; N, 24.84. Found: C, 38.92; H, 4.68; N, 24.56. MS (ESI−): m/z=298 [M−H]$^-$.

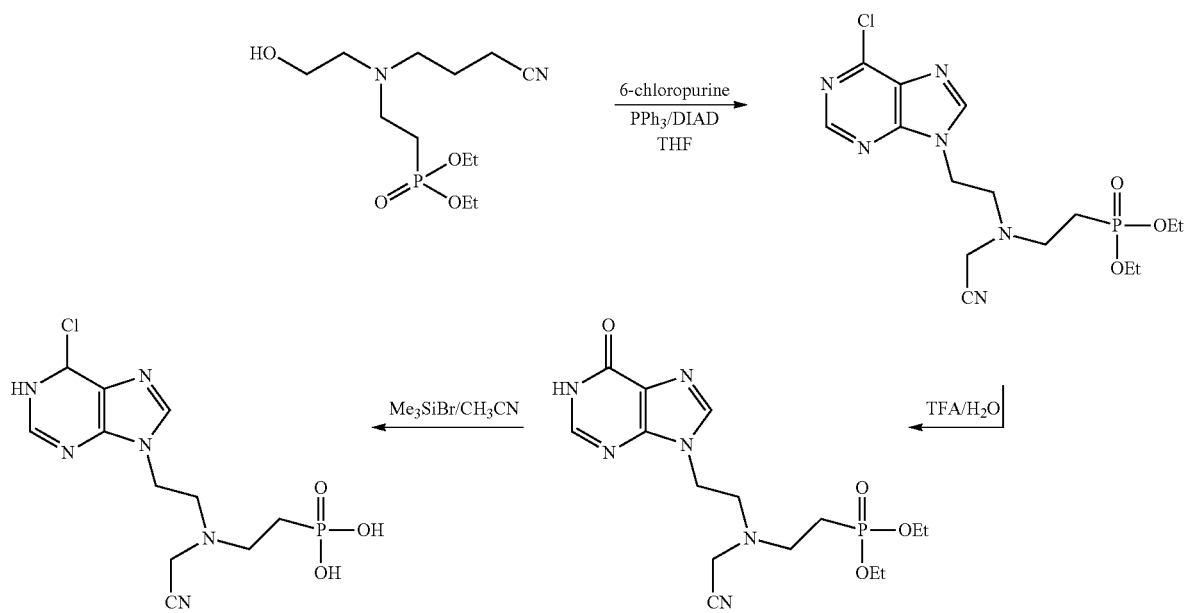

Example 19

9-[(N-(2-Cyanoethyl)-N-(2-phosphonoethyl))-2-aminoethyl]hypoxanthine

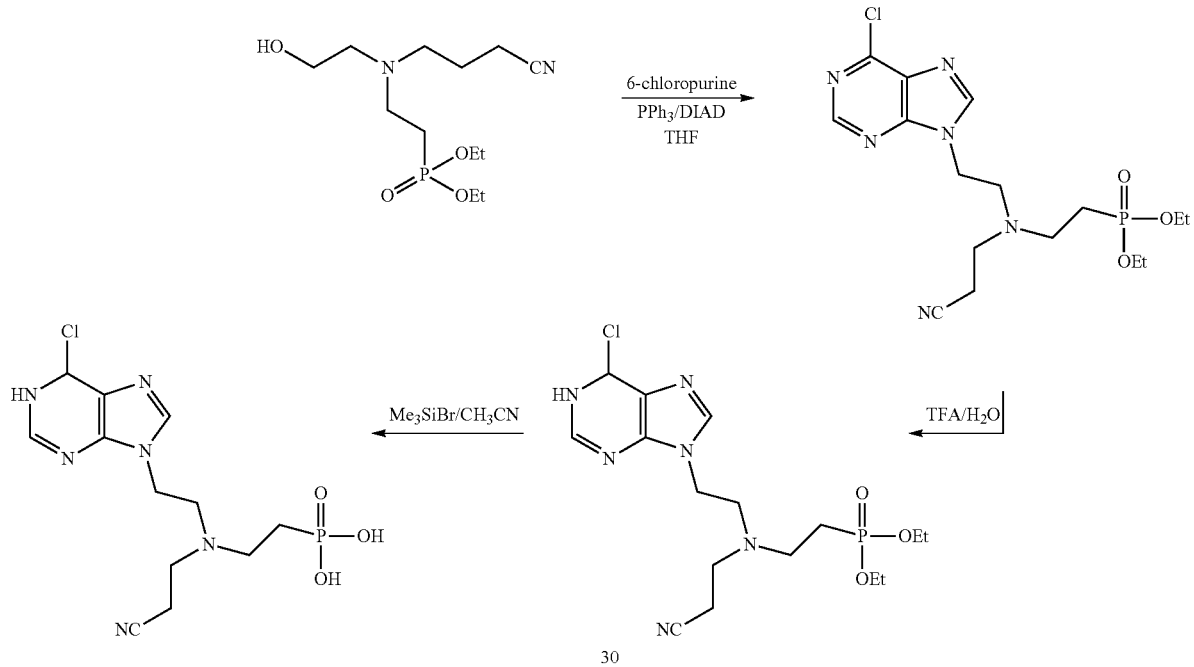

To a solution of triphenylphosphine (6.3 g, 24 mmol) in dry THF (100 ml) cooled to −30° C. under argon atmosphere diisopropylazadicarboxylate (DIAD, 4.4 ml, 23 mmol) was added slowly. The mixture was stirred for 30 minutes and this preformed complex was added to 6-chloropurine (3.5 g, 22.6 mmol), dry THF (70 ml) and diethyl 2-(2-cyanoethylamino) ethylphosphonate (see Example 5, 3.11 g, 11.2 mmol) at −30° C. under argon. The resulting mixture was slowly warmed to moth temperature and stirred for 48 h. Solvent was evaporated and the crude mixture purified by chromatography on silica gel (MeOH—CHCl$_3$). Diethyl 9-[(N-(2-cyanoethyl)-N-(2-phosphonoethyl))-2-aminoethyl]-6-chloropurine was isolated in 85% yield (3.95 g).

This intermediate (1.66 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) diethyl 9-[(N-(2-cyanoethyl)-N-(2-phosphonoethyl))-2-aminoethyl]hypoxanthine was obtained in 95% yield (1.5 g).

A mixture of this diethyl ester (0.79 g, 2 mmol), acetonitrile (20 ml), 2,6-lutidine (0.1 ml) and BrSiMe$_3$ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N-(2-Cyanoethyl)-N-(2-phosphonoethyl))-2-aminoethyl]hypoxanthine was obtained as a white foam in 67% yield (0.46 g). $^1$H NMR (DMSO-d$_6$): 12.26 s, 1 H (NH); 8.09 s, 1 H and 8.03 s, 1 H (H-2 and H-8); 4.18 t, 2 H, J(1',2')=6.2 (H-1'); 2.82 t, 2 H, J(2', 1')=6.2 (H-2'); 2.74 t, 2 H, J(5',6')=6.7 (H-5'); 2.68 m, 2 H (H-3'); 2.60 m, 2 H (H-6'); 1.55 m, 2 H (H-4'). $^{13}$C NMR (DMSO-d$_6$): 156.53 (C-6); 148.24 (C-4); 145.20 (C-2); 140.47 (C-8); 123.68 (C-5); 119.66 (CN); 51.87, 48.23 and 47.13 (C-2', C-5' and C-3'); 41.47 (C-1'); 24.98 d, J(P,C)=131.9 (C-4'); 15.53 (C-6'). Anal. Calcd for C$_{12}$H$_{17}$N$_6$O$_4$P.4/3H$_2$O: C, 39.56; H, 5.44; N, 23.07. Found: C, 39.70; H, 5.27; N, 23.07. MS (ESI-): m/z=339 [M−H]$^-$.

Example 20

9-[(N-(2-Cyanopropyl)-N-(2-phosphonoethyl))-2-aminoethyl]hypoxanthine

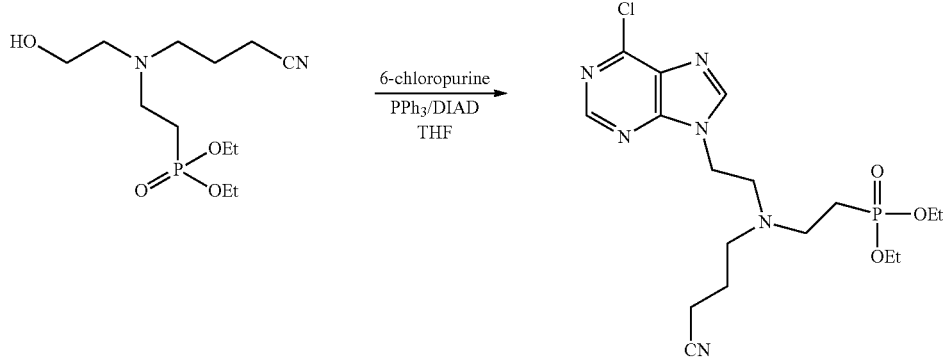

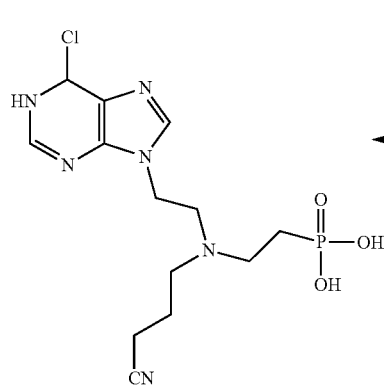
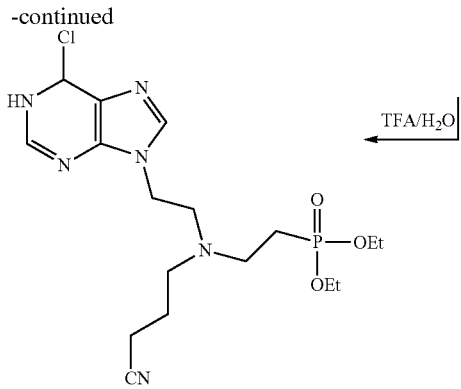

To a solution of triphenylphosphine (6.3 g, 24 mmol) in dry THF (100 ml) cooled to −30° C. under argon atmosphere diisopropylazadicarboxylate (DIAD, 4.4 ml, 23 mmol) was added slowly. The mixture was stirred for 30 minutes and this preformed complex was added to 6-chloropurine (3.5 g, 22.6 mmol), dry THF (70 ml) and diethyl 2-(2-cyanopropylamino) ethylphosphonate (3.27 g, 11.2 mmol) at −30° C. under argon. The resulting mixture was slowly warmed to room temperature and stirred for 48 h. Solvent was evaporated and the crude mixture purified by chromatography on silica gel (MeOH—CHCl$_3$). Diethyl 9-[(N-(2-cyanopropyl)-N-(2-phosphonoethyl))-2-aminoethyl]-6-chloropurine was isolated in 81% yield (3.89 g).

This intermediate (1.72 g, 4 mmol) was dissolved in trifluoroacetic acid (aqueous, 75%. 20 ml) and stirred overnight. The solvent was evaporated and the residue codistilled with water (3×) and ethanol. After chromatography on silica gel (MeOH—CHCl$_3$) diethyl 9-[(N-(2-cyanopropyl)-N-(2-phosphonoethyl))-2-aminoethyl]hypoxanthine was obtained in 76% yield (1.25 g).

A mixture of this diethyl ester (0.85 g, 2 mmol), acetonitrile (20 ml), 2,6-lutidine (0.1 ml) and BrSiMe$_3$ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N-(2-Cyanopropyl)-N-(2-phosphonoethyl))-2-aminoethyl]hypoxanthine was obtained as a white solid in 51% yield (0.36g). $^1$H NMR (DMSO-d$_6$): 12.34 s, 1 H (NH); 8.12 s, 1 H and 8.05 s, 1 H (H-2 and H-8); 4.32 t, 2 H, J(1',2')=6.0 (H-L'); 3.10 t, 2 H, J(2',1')=6.0 (H-2'); 2.92 dd, 2 H, J=7.5 and 15.2 (H-3'); 2.75 t, 2 H, J(5',6')=6.8 (H-5'); 2.38 t, 2 H, J(7',6')=7.2 (H-7'); 1.74 m, 2 H (H-4'); 1.68 m, 2 H(H-6'). NMR (DMSO-d$_6$): 156.45 (C-6); 148.26 (C-4); 145.40 (C-2); 140.40 (C-8); 123.76 (C-5); 120.04 (CN); 51.48, 50.75 and 47.57 (C-2', C-5' and C-3'); 40.23 (C-1'); 23.75 d, J(P,C)=131.5 (C-4'); 21.46 (C-6'); 13.52 (C-6').Anal. Calcd for C$_{13}$H$_{19}$N$_6$O$_4$P.2H$_2$O: C, 40.00; H, 5.94; N, 21.54. Found: C, 40.44; H, 5.85; N, 21.31. MS (ESI−): m/z=353 [M−H]$^−$.

Example 21

9-[(N-(Carboxymethyl)-N-(2-phosphonoethyl))-2-aminoethyl]hypoxanthine

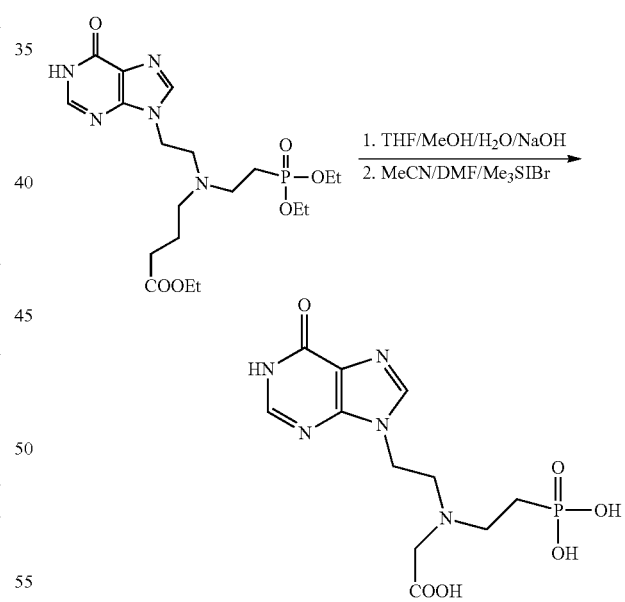

A mixture of diethyl 9[(N-(2-ethoxy-2-oxoethyl)-N-(2-phosphonoethyl))-2-aminoethyl]hypoxanthine (intermediate from Example 15, 0.43 g, 1 mmol), tetrahydrofuran (10 ml), methanol (10 ml) and aqueous NaOH (10 M, 0.2 ml) was refluxed for 2 h and then stirred at room temperature overnight. After evaporation and codistillation with toluene/ethanol and acetonitrile, the residue was dissolved in acetonitrile (20 ml). 2,6-Lutidine (0.1 ml) and BrSiMe$_3$ (1 ml) were added and the mixture was stirred for 2 days at room temperature. After evaporation and codistillation with acetonitrile, the residue was treated with aqueous methanol (2:1, 30 ml) for 1 h, evaporated and codistilled with water. The residue was purified by preparative HPLC (water-methanol). 9-[(N-(Carboxymethyl)-N-(2-phosphonoethyl))-2-aminoethyl]hypoxanthine was obtained as white solid in 35% yield (0.12 g). $^1$H NMR (DMSO-$d_6$): 12.29 s, 1 H (NH); 8.11 s, 1 H and 8.03 s, 1 H (H-2 and H-8); 4.20 t, 2 H, J(1',2')=6.0 (H-1'); 3.35 s, 2 H (H-5'),; 2.97 t, 2 H, J(2',1')=6.0 (H-2'); 2.80 m, 2 H(H-3'); 1.54 m, 2 H (H-4'). $^{13}$C NMR (DMSO-$d_6$): 172.22 (CO); 156.61 (C-6); 148.30 (C-4); 145.32 (C-2); 140.72 (C-8); 123.63 (C-5); 53.86.52.34 and 48.25 (C-2', C-5' and C-3'); 41.39 (C-1'); 26.05 d, J(P,C)=131.4 (C-4').Anal. Calcd for $C_{11}H_{16}N_5O_6P.1/2H_2O$: C, 37.29; H, 4.84; N, 19.77. Found: C, 37.48; H, 4.65; N, 19.49. MS (ESI-): m/z=344 [M-H]$^-$.

Example 22

9-[(N-(2-Carboxyethyl)-N-(2-phosphonoethyl))-2-aminoethyl]hypoxanthine

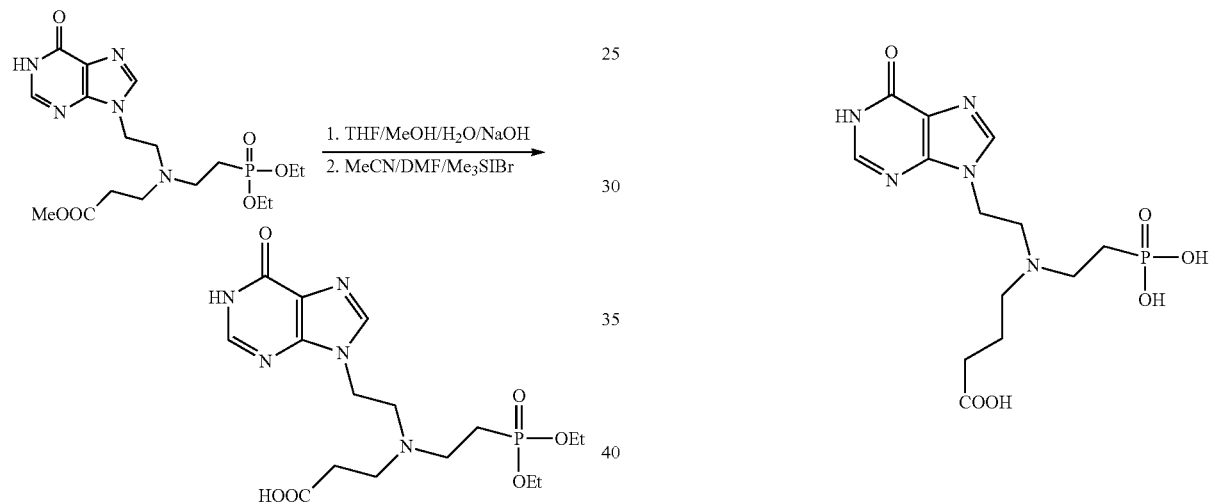

A mixture of diethyl 9-[(N-(2-methoxy-2-oxopropyl)-N-(2-phosphonoethyl))-2-aminoethyl]hypoxanthine (intermediate from Example 16, 0.43 g, 1 mmol), tetrahydrofuran (10 ml), methanol (10 ml) and aqueous NaOH (10 M, 0.2 ml) was refluxed for 2 h and then stirred at room temperature overnight. After evaporation and codistillation with toluene/ethanol and acetonitrile, the residue was dissolved in acetonitrile (20 ml). 2,6-Lutidine (0.1 ml) and BrSiMe$_3$ (1 ml) were added and the mixture was stirred for 2 days at room temperature. After evaporation and codistillation with acetonitrile, the residue was treated with aqueous methanol (2:1, 30 ml) for 1 h, evaporated and codistilled with water. The residue was purified by preparative HPLC (water-methanol). 9-[(N-(Carboxyethyl)-N-(2-phosphonoethyl))-2-aminoethyl]hypoxanthine was obtained as white solid in 60% yield (0.25 g). $^1$H NMR (DMSO-$d_6$): 12.26 s, 1 H (NH); 8.05 s, 1 H and 8.03 s, 1 H (H-2 and H-8); 4.21 t, 2 H, J(1',2')=6.1 (H-1'); 2.86 t, 2 H, J(2',1')=6.1 (H-2'); 2.77 t, 2 H, J(5',6')=6.9 (H-5'); 2.74 m, 2 H(H-3'); 2.30 t, 2 H, J(6',5') 6.9 (H-6'); 1.56 m, 2 H (H-4'). $^{13}$C NMR (DMSO-$d_6$): 173.12 (CO); 156.52 (C-6); 148.21 (C-4); 145.24 (C-2); 140.54 (C-8); 123.68 (C-5); 51.99, 48.29and 47.54 (C-2', C-5' and C-3'); 41.16 (C-1'); 31.58 (C-6'); 24.59 d, J(P,C)=131.6 (C-4'). Anal. Calcd for $C_{12}H_{18}N_5O_6P.5/3H_2O$: C, 37.02; H, 5.52; N, 17.99. Found: C, 37.18; H, 5.55; N, 17.75. MS (ESI-): m/z=358 [M-H]$^-$.

Example 23

9-[(N-(Carboxypropyl)-N-(2-phosphonoethyl))-2-aminoethyl]hypoxanthine

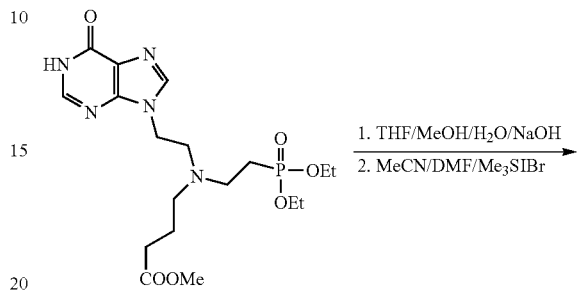

A mixture of diethyl 9-[(N-(4-methoxy-4-oxobutyl)-N-(2-phosphonoethyl))-2-aminoethyl]hypoxanthine (intermediate from Example 17, 0.44 g, 1 mmol), tetrahydrofuran (10 ml), methanol (10 ml) and aqueous NaOH (10 M, 0.2 ml) was refluxed for 2 h and then stirred at room temperature overnight. After evaporation and codistillation with toluene/ethanol and acetonitrile, the residue was dissolved in acetonitrile (20 ml). 2,6-Lutidine (0.1 ml) and BrSiMe$_3$ (1 ml) were added and the mixture was stirred for 2 days at room temperature. After evaporation and codistillation with acetonitrile, the residue was treated with aqueous methanol (2:1, 30 ml) for 1 h, evaporated and codistilled with water. The residue was purified by preparative HPLC (water-methanol). 9-[(N-(Carboxymethyl)-N-(2-phosphonoethyl))-2-aminoethyl]hypoxanthine was obtained as white solid in 56% yield (0.21 g). $^1$H NMR (DMSO-$d_6$): 12.31 s, 1 H (NH); 8.10 s, 1 H and 8.03 s, 1 H (11-2 and H-8); 4.28 t, 2 H, J(1',2')=6.0 (H-1'); 3.00 t, 2 H, 6.0 (H-2'); 2.84 m, 2 H(H-3');2.60 t, 2 H, J(5',6')=6.9 (H-5'); 2.12 t, 2 H, J(7',6')=7.2 (H-7'); 1.65 m, 2 H (H-4'); 1.56 m, 2 H (H-6'). $^{13}$C NMR (DMSO-$d_6$): 174.03 (CO); 156.49 (C-6); 148.25 (C-4); 145.29 (C-2); 140.49 (C-8); 123.74 (C-5); 51.68, 51.48 and 47.72 (C-2', C-5' and C-3'); 40.68 (C-1'); 30.65 (C-7'); 24.20 d, J(P,C)=131.5 (C-4'); 21.12 (C-6').Anal. Calcd for $C_{13}H_{20}N_5O_6P.3/2H_2O$: C, 40.59; H, 6.39; N, 17.75. Found: C, 40.64; H, 6.21; N, 17.62. MS (ESI-): m/z=372 [M-H]$^-$.

Example 24

9-[(N-(2-Hydroxyethyl)-N-(2-phosphonoethyl))-2-aminoethyl]hypoxanthine

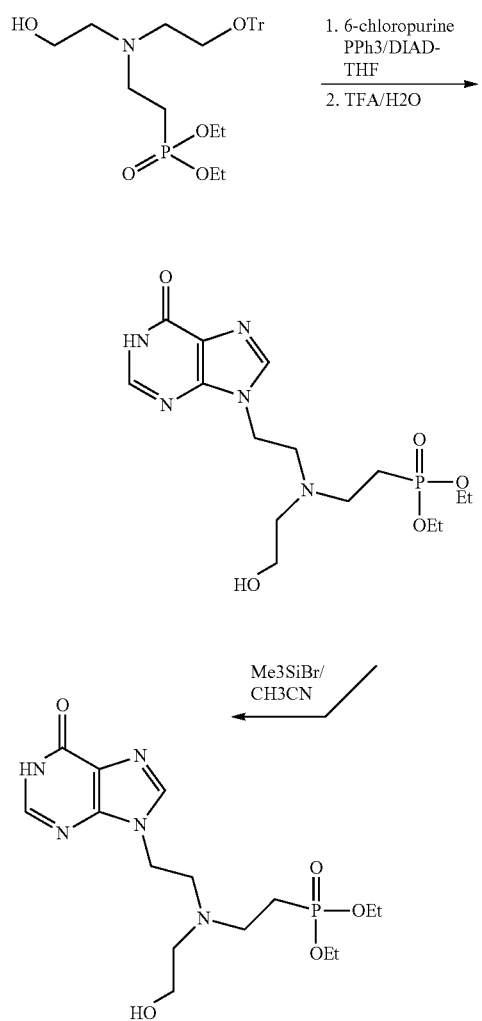

To a solution of triphenylphosphine (6.3 g, 24 mmol) in dry THF (100 ml) cooled to −30° C. under argon atmosphere diisopropylazadicarboxylate (DIAD, 4.4 ml, 23 mmol) was added slowly. The mixture was stirred for 30 minutes and this preformed complex was added to 6-chloropurine (3.5 g, 22.6 mmol), dry THF (70 ml) and diethyl 2((2-hydroxyethyl)(2-(trityloxy)ethyl)amino)ethylphosphonate (see Example 10, 5.72 g, 11.2 mmol) at −30° C. under argon. The resulting mixture was slowly warmed to room temperature and stirred for 48 h. Solvent was evaporated and the crude mixture purified by chromatography on silica gel (MeOH—CHCl$_3$). This intermediate was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) the diethyl 9:[(N-(2-hydroxyethyl)-N-(2-phosphonoethyl))-2-aminoethyl]hypoxanthine was obtained in 60% yield (2.60 g).

A mixture of this diethyl ester (0.77 g, 2 mmol), acetonitrile (20 ml), dimethylformamide (2.5 ml), 2,6-lutidine (0.1 ml) and BrSiMe$_3$ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N-(2-Hydroxyethyl)-N-(2-phosphonoethyl))-2-aminoethyl]hypoxanthine was obtained as a white foam in 36% yield (0.24 g). $^1$H NMR (DMSO-d$_6$): 12.39 s, 1 H (NH); 8.16 s, 1 H and 8.07 s, 1 H (H-2 and H-8); 4.45 t, 2 H, =5.8 (H-1'); 3.60 m, 2 H (H-6'); 3.37 t, 2 H, J(2',1')=5.8 (H-2'); 3.28 m, 2 H(H-3'); 3.04 t, 2 H(H-5'); 1.86 m, 2 H (H-4'). $^{13}$C NMR (DMSO-d$_6$): 156.48 (C-6); 148.25 (C-4); 145.52 (C-2); 140.41 (C-8); 123.82 (C-5); 56.48, 54.51, 51.63 and 48.47 (C-6', C-2', C-5' and C-3'); 23.53 d, J(P,C)=131.2 (C-4'). Anal. Calcd for C$_{11}$H$_{18}$N$_5$O$_5$P: C, 39.88; H, 5.48; N, 21.14. Found: C, 40.23; H, 5.524; N, 20.92. MS (ESI−): m/z=330 [M−H]$^-$.

Example 25

9-[(N,N-(Bis-2-phosphonoethyl))-2-aminoethyl]hypoxanthine

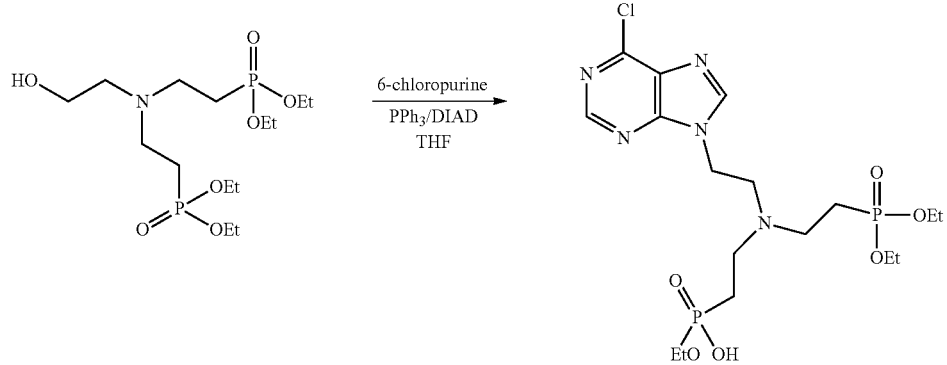

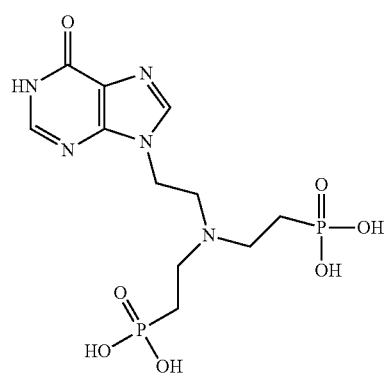 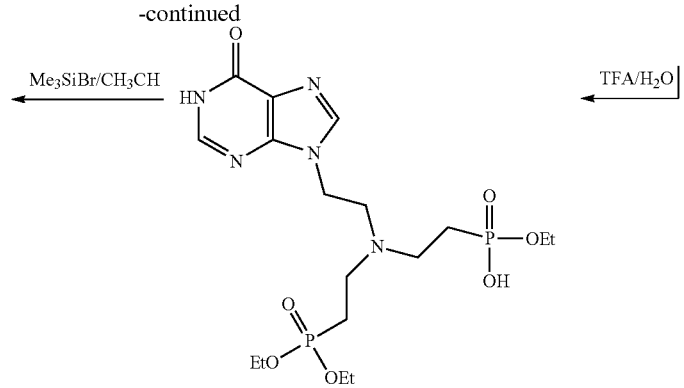

To a solution of triphenylphosphine (6.3 g, 24 mmol) in dry THF (100 ml) cooled to −30° C. under argon atmosphere diisopropylazadicarboxylate (DIAD, 4.4 ml, 23 mmol) was added slowly. The mixture was stirred for 30 minutes and this preformed complex was added to 6-chloropurine (3.5 g, 22.6 mmol), dry THF (70 ml) and tetraethyl 2,2'-2-hydroxyethylazanediyl)bis(ethane-2,1-diypdiphosphonate (see Example 11, 4.3 g, 11.2 mmol) at −30° C. under argon. The resulting mixture was slowly warmed to room temperature and stirred for 48 h. Solvent was evaporated and the crude mixture purified by chromatography on silica gel (MeOH—CHCl$_3$). Tetraethyl 9-[(N,N-(bis-2-phosphonoethyl))-2-aminoethyl]-6-chloropurine was isolated in 80% yield (4.71 g).

This intermediate (2.10 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) tetraethyl 9-[(N,N-(bis-2-phosphonoethyl))-2-aminoethyl]hypoxanthine was obtained in 67% yield (1.36 g).

A mixture of this tetraethyl ester (1.01 g, 2 mmol), acetonitrile (20 ml), 2,6-lutidine (0.1 ml) and BrSiMe$_3$ (2 ml) was stirred for 2 days at room temperature. After evaporation and codistillation with acetonitrile, the residue was treated with aqueous methanol (2:1, 30 ml) for 1 h and evaporated. The residue was purified by preparative HPLC. 9-[(N,N-(Bis-2-phosphonoethyl))-2-aminoethyl]hypoxanthine was obtained as a white solid in 85% yield (0.67 g). $^1$H NMR (DMSO-d$_6$): 12.64 s, 1 H (NH); 8.51 s, 1 H and 8.15 s, 1 H (H-2 and H-8); 4.64 t, 2 H, J(1',2')=6.8 (H-1'); 3.67 t, 2 H, J(2',1')=6.8 (H-2'); 3.35 m, 4 H (H-3' and H-5'); 2.10 m, 4 H (H-4' and H-6'). $^{13}$C NMR (DMSO-d$_6$): 155.78 (C-6); 148.08 (C-4); 146.40 (C-2); 140.15 (C-8); 122.37 (C-5); 49.84 (C-2'); 47.51, 2C (C-3' and C-5'); 38.17 (C-1'); 22.30 d, 2C, J(P,C)=132.4 (C-4' and C-6'). Anal. Calcd for C$_{11}$H$_{19}$N$_5$O$_7$P: C, 33.43; H, 4.85: N, 17.72. Found: C, 33.96; H, 4.71; N, 17.46. MS (ESI-): m/z=394 [M−H]$^-$.

Example 26

9-[(N-(2-Phosphonoethyl))-2-aminoethyl]hypoxanthine

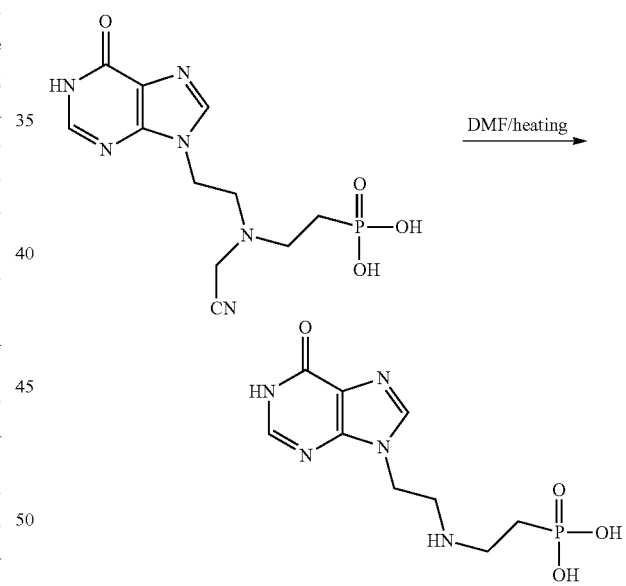

9-[(N-(2-Cyanomethyl)-N-(2-phosphonoethyl))-2-aminoethyl]hypoxanthine (Example 18, 163 mg, 0.5 mmol) in dimethylformamide (10 ml) was heated at 120° C. for 3 days. The solvent was then evaporated and the residue codistilled with toluene. The residue was purified by preparative HPLC (water-methanol), yield 49% (70 mg). $^1$H NMR (D2O+NaOD): 8.04 s, 1 H and 7.88 s, 1 H (H-2 and H-8); 4.21 t, 2 H, J(1',2')=6.2 (H-1'); 2.96 t, 2 H, J(2',1')=6.2 (H-2'); 2.69dd, 2 H, J=7.3 and 16.3 (H-3'); 1.50 m, 2 H (H-4'). $^{13}$C NMR (1520+NaOD): 168.34 (C-6); 154.10 (C-2); 150.33 (C-4); 123.76 (C-5); 47.80, 45.21 and 43.89 (C-2', C-3' and C-1'); 29.99 d, J(P,C)=127.2 (C-4'). Anal. Calcd. for C$_9$H$_{14}$N$_5$O$_4$P.H$_2$O: C, 35.41; H, 5.28; N, 22.94. Found: C, 35.06; H, 5.29; N, 23.39. MS (ESI-): m/z=286 [M−H]$^-$.

Example 27

9-[(N-(2-Phosphonomethoxyethyl)-N-(2-phosphono-ethyl))-2-aminoethyl]hypoxanthine

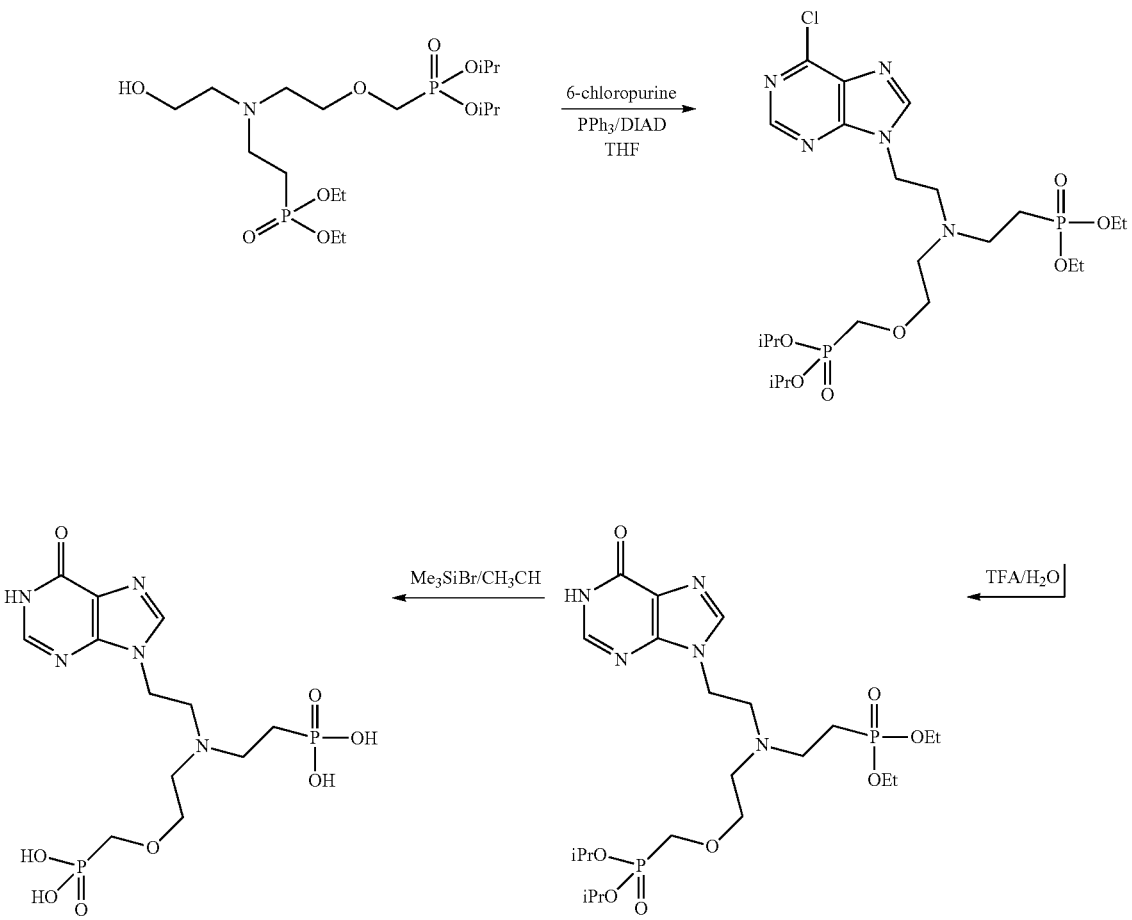

To a solution of triphenylphosphine (6.3 g, 24 mmol) in dry THF (100 ml) cooled to −30° C. under argon atmosphere diisopropylazadicarboxylate (DIAD, 4.4 ml, 23 mmol) was added slowly. The mixture was stirred for 30 minutes and this preformed complex was added to 6-chloropurine (3.8 g, 22.6 mmol), dry THF (70 ml) and diethyl diisopropyl (2-((N-hydroxyethyl)(N-2-phosphonomethoxyethyl)amino)eth-ylphosphonate (see Example 13, 4.65 g, 11.2 mmol) at −30° C. under argon. The resulting mixture was slowly warmed to room temperature and stirred for 48 h. Solvent was evaporated and the crude mixture purified by chromatography on silica gel (MeOH—CHCl$_3$). Diethyl diisopropyl 9-[(N-(2-phosphonomethoxyethyl)-N-(2-phosphonoethyl))-2-amino-ethyl]-6-chloropurine was isolated in 73% yield (4.77 g).

This intermediate (2.34 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) diethyl diisopropyl 9-[(N-(2-phosphonomethoxyethyl)-N-(2-phosphonoethyl))-2-aminoethyl]hypoxanthine was obtained in 97% yield (2.2 g).

A mixture of this diethyl diisopropylester (1.13 g, 2 mmol), acetonitrile (20 ml) and BrSiMe$_3$ (3 ml) was stirred for 3 days at room temperature. After evaporation and codistillation with acetonitrile, the residue was treated with aqueous methanol (2:1, 30 ml) for 1 h and evaporated. The residue was purified by preparative HPLC. 9-[(N-(2-Phosphonomethoxyethyl)-N-(2-phosphonoethyl))-2-aminoethyl]hypoxanthine was obtained as a white foam in 71% yield (0.60 g). $^1$H NMR (DMSO-d$_6$): 12.40 s, 1 H (NH); 8.15 s, 1 H and 8.08 s, 1 H (H-2 and H-8); 4.52 t, 2 H, J(1',2')=6.0 (H-1'); 3.82 m, 2 H, (H-6'); 3.56 m, 4 H (H-2' and H-7'); 3.33 m, 4 H (H-3' and H-5'); 1.90 m, 2 H (11-4'), $^{13}$C NMR (DMSO-d$_6$): 156.48 (C-6); 148.28 (C-4); 145,71 (C-2); 140.30 (C-8); 123.86 (C-5); 66.84 (C-6'); 66.82 d, J(P,C)=157.5 (C-7'); 52.66, 51.55 and 49.44 (C-2', C-3' and C-5'); 38.67 (C-1'); 22.64 d, J(P,C)=131.0 (C-4'). HRMS calcd. for C$_{12}$H$_{20}$N$_5$O$_8$P$_2$: 424.07926; found: 424.07932. MS (ESI): m/z=424 [M−H]$^-$.

Example 28

9-[(N-(Phosphonoethyl)-N-(2-phosphonomethyl))-2-aminoethyl]hypoxanthine

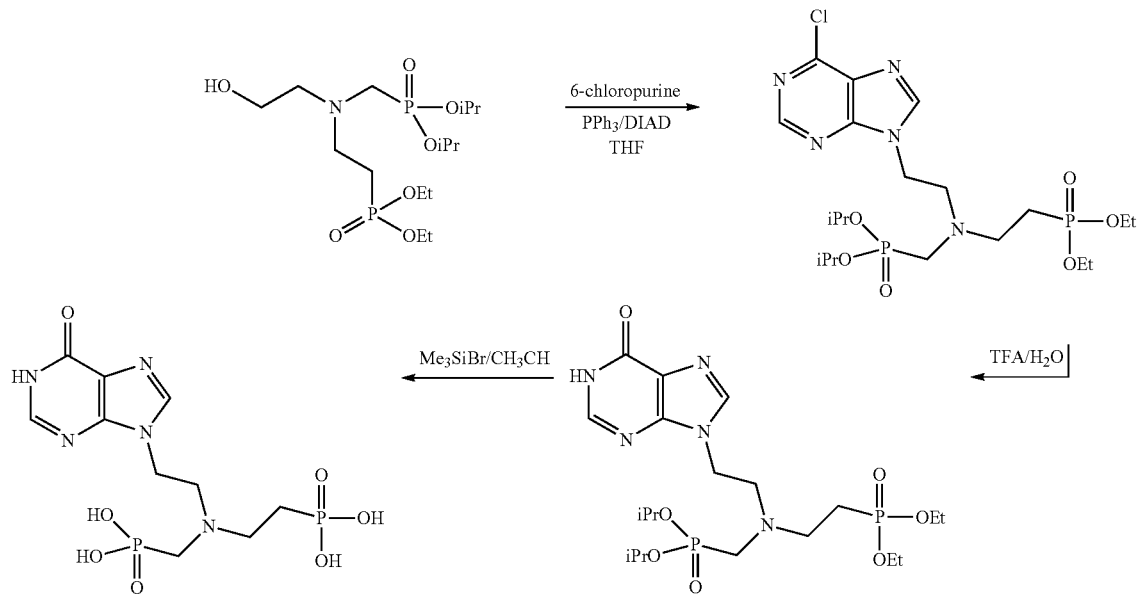

To a solution of triphenylphosphine (6.3 g, 24 mmol) in dry THF (100 ml) cooled to −30° C. under argon atmosphere diisopropylazadicarboxylate (DIAD, 4.4 ml, 23 mmol) was added slowly. The mixture was stirred for 30 minutes and this preformed complex was added to 6-chloropurine (3.5 g, 22.6 mmol), dry THF (70 ml) and diethyl diisopropyl 2-((N-hydroxyethyl)(N-phosphonomethypamino)ethylphosphonate (see Example 14, 4.51 g, 11.2 mmol) at −30° C. under argon. The resulting mixture was slowly warmed to room temperature and stirred for 48 h. Solvent was evaporated and the crude mixture purified by chromatography on silica gel (MeOH—CHCl$_3$). Diethyl diisopropyl 9-[(N-(2-phosphonoethyl)-N-(2-phosphonomethyl))-2-aminoethyl]-6-chloropurine was isolated in 53% yield (3.21 g).

This intermediate (2.16 g, 4 mmol) was dissolved in trifluoroacetic acid (aqueous, 75%, 20 ml) and stirred overnight. The solvent was evaporated and the residue codistilled with water (3×) and ethanol. After chromatography on silica gel (MeOH—CHCl$_3$) diethyl di isopropyl 9-[(N-(2-phosphonoethyl)-N-(2-phosphonomethyl))-2-aminoethyl]hypoxanthine was obtained in 96% yield (2.0 g).

A mixture of this diethyl diisopropylester (1.04 g, 2 mmol), acetonitrile (20 ml) and BrSiMe$_3$ (3 ml) was stirred for 3 days at room temperature. After evaporation and codistillation with acetonitrile, the residue was treated with aqueous methanol (2:1, 30 ml) for 1 h and evaporated. The residue was purified by preparative HPLC. 9-[(N-(2-Phosphonoethyl)-N-(2-phosphonomethyl))-2-aminoethyl]hypoxanthine was obtained as a white foam in 55% yield (0.42 g). $^1$H NMR (DMSO-d$_6$): 12.47 s, 1 H (NH); 8.30 s, 1 H and 8.10 s, 1 H (H-2 and H-8); 4.51 t, 2 H, J(1',2')=6.0 (H-1'); 3.53 t, 2 H, J(2',1')=6.0 (H-2'); 3.35 d, 2 H, J=12.8. (H-5'); 3.50 m, 2 H (H-3'); 1.96 m, 2 H (H-4'). $^{13}$C NMR (DMSO-d$_6$): 156.15 (C-6); 148.15 (C-4); 145.98 (C-2); 140.33 (C-8); 122.99 (C-5); 53.04 and 50.23 (C-2' and C-3'); 48.94 d, J(P,C)=146.4 (C-5'); 23.41 d, J(P,C)=133.6 (C-4'). HRMS calcd. for C$_{10}$H$_{16}$N$_5$O$_7$P$_2$: 380.05304; found: 380.05285. MS (ESI): m/z 380 [M−H]$^−$.

Example 29

(2S,2'S)-isopropyl-2,2'-{[2-((2-cyanoethyl)(2-(hypoxanthine-9-yl)ethyl)amino)ethyl]phosphoryl}bis(azanediyl)bis(3-phenylpropanoate)

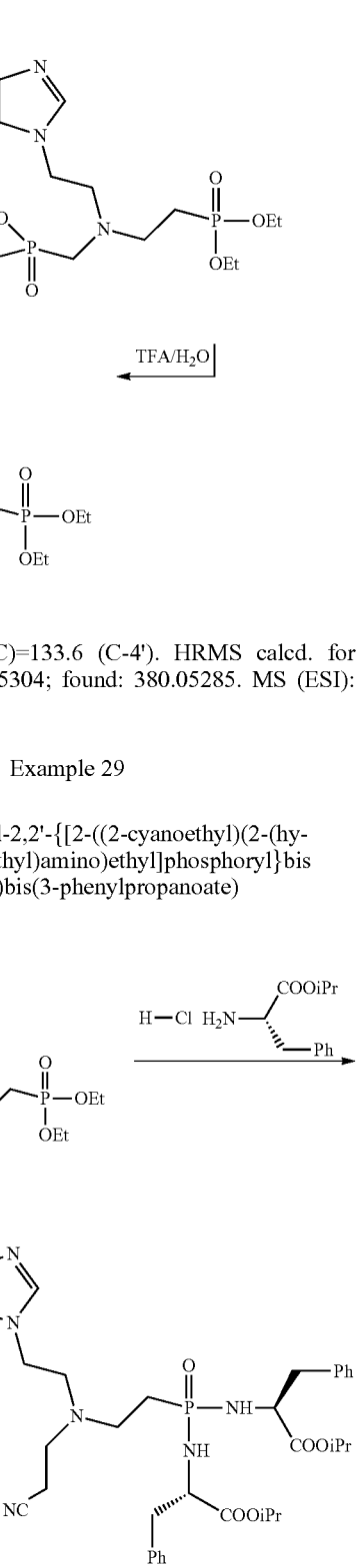

A mixture of diethyl 9-[(N-(2-cyanoethyl)-N-(2-phosphonoethyl))-2-aminoethyl]hypoxanthine (intermediate in Example 19, 0.79 g, 2 mmol), acetonitrile (20 ml) and BrSiMe$_3$ (1.2 ml) an 2,6-lutidine (0.1 ml) was stirred for 2 days at room temperature under argon. After evaporation and codistillation with acetonitrile, the residue was dissolved in pyridine (15 ml) and isopropyl (L)-phenylalamine hydrochloride (1.95 g, 8 mmol) and triethylamine (4 ml) were added. The mixture was heated to 60° C. under argon atmosphere and then solution of Aldrithiol (2.64 g, 12 mmol) and triphenylphosphine (3.14 g, 12 mmol) in dry pyridine (20 ml) was added. The reaction mixture was heated at 60° C. for 24 h, the solvent was evaporated and the residue was purified by column chromatography on silica gel. The phosphoramidate prodrug was obtained as foam in 37% yield (0.53 g). $^1$H NMR (DMSO-d$_6$): 12.28 s, 1 H (NH); 8.06 s, 1 H and 8.02 s, 1 H (H-8 and H-2); 7.20 m, 10 H (Ar); 4.81 m, 2 H (iPr); 4.48 t, 1 H, J=11.6 (NH); 4.13 m, 3 H, (NH and H-1'); 3.94 m, 1 H and 3.85 m, 1 H (CH); 2.84 m, 3 H and 2.73 m, 1 H (CH$_2$Ph); 2.69 t. 2 H, J(2',1')=6.2 (H-2'); 2.61 t, 2 H, J(5',6')=6.7 (H-5'); 2.45 t, 2 H, J(6',5')=6.7 (H-6'); 1.35 m, 2 H (H-4'); 1.17 d, 3 H, 1.06 d, 3 H and 1.01 d, 3 H, J=6.2 (iPr). $^{13}$C NMR (DMSO-d$_6$): 172.93 and 172.74 (CO); 156.86 (C-6); 148.50 (C-4); 145.51 (C-2); 140.69 (C-8); 137.46, 137.39, 129.64, 2C, 129.58, 2C, 128.27, 2C, 128.23, 2C, 126.65 and 126.56 (Ar); 123.98 (C-5); 119.96 (CN); 68.01 and 67.87 (iPr); 54.24 and 54.09 (NHCH); 52.15 (C-2'); 48.13 (C-5'); 46.89 (C-3'); 41.45 (C-1');'24.85 d, J(P,C)=135.2 (C-4'); 21.59 m. 4C (iPr); 15.52 (C-6'). MS (ESI): m/z=719 [M+H]$^+$.

As referred to herein this compound provides a prodrug form of a compound of the invention.

Example 30

(2S,2'S)-isopropyl-2,2'-{[2-((2-(guanine-9-yl)ethyl)(2-cyanoethyl)amino)ethyl]phosphoryl}bis(azanediyl)bis(3-phenylpropanoate)

A mixture of diethyl 9-[(N(2-cyanoethyl)-N-(2-phosphonoethyl))-2-aminoethyl]guanine (intermediate in Example 5, 0.41 g, 1 mmol), acetonitrile (15 ml) and BrSiMe$_3$ (0.6 ml) an 2,6-lutidine (0.05 ml) was stirred for 2 days at room temperature, under argon. After evaporation and codistillation with acetonitrile, the residue was dissolved in pyridine (10 ml) and isopropyl (L)-phenylalamine hydrochloride (1.0 g, 4 mmol) and triethylamine (2 ml) were added. The mixture was heated to 60° C. under argon atmosphere and then solution of Aldrithiol (1.32 g, 6 mmol) and triphenylphosphine (1.6 g, 6 mmol) in dry pyridine (10 ml) was added. The reaction mixture was heated at 60° C. for 24 h, the solvent was evaporated and the residue was purified by column chromatography on silica gel. The phosphoramidate prodrug was obtained as foam in 56% yield (0.82 g). $^1$H NMR (DMSO-d$_6$): 10.57 s, 1 H (NH); 7.66 s, 1 H (H-8); 7.21 m, 10 H (Ar); 6.47 s, 2 H (NH$_2$); 4.80 m, 2 H (iPr); 4.49 t, 1 H, J=11.1 (NH); 4.18 t, 1 H, J=10.6 (NH); 3.91 t, 2 H, J(1',2')=6.5 (H-1'); 3.88 m, 2 H, (NHCH); 2.86 m, 3 H and 2.73 m, 1 H (CH$_2$Ph); 2.61 m. 2 H, (H-2'); 2.61 t, 2 H, J(5',6')=6.7 (H-5'); 2.50 m, 2 H (H-3'); 2.48 t, 2 H, J(6',5')=6.7 (11-6'); 1.39 m. 2 H (H-4'); 1.17 d, 3 H, 1.12 d, 3 H, 1.06 d, 3 H and 1.01 d, 3 H, J=6.2 (iPr). $^{13}$C NMR (DMSO-d$_6$): 172.63 and 172.47 (CO); 156.71 (C-6); 153.40 (C-2); 150.98 (C-4): 137.50 (C-8); 137.17, 137.09, 129.35, 2 C, 129.29, 2 C, 127.98, 2 C, 127.93, 2 C, 126.36 and 126.27 (Ar); 119.77 (CN); 116.29 (C-5); 67.74 and 67.58 (iPr); 53.99 and 53.83 (NHCH); 51.82 (C-2'); 47.95 (C-5'); 46.49 (C-3'); 40.59 (C-1'); 25.39 d, J(P,C)=110.7 (C-4'); 21.30 m, 4 C (iPr); 15.27 (C-6'). MS (ESI): m/z=734 [M+H]$^+$.

As referred to herein this compound provides a prodrug form of a compound of the invention.

Example 31

(2S,2'S)-diethyl-2,2'-{[2-((2-(guanine-9-yl)ethyl)(4-methoxy-4-oxobutyl)amino)ethyl]phosphoryl}bis(azanediyl)bis(3-phenylpropanoate)

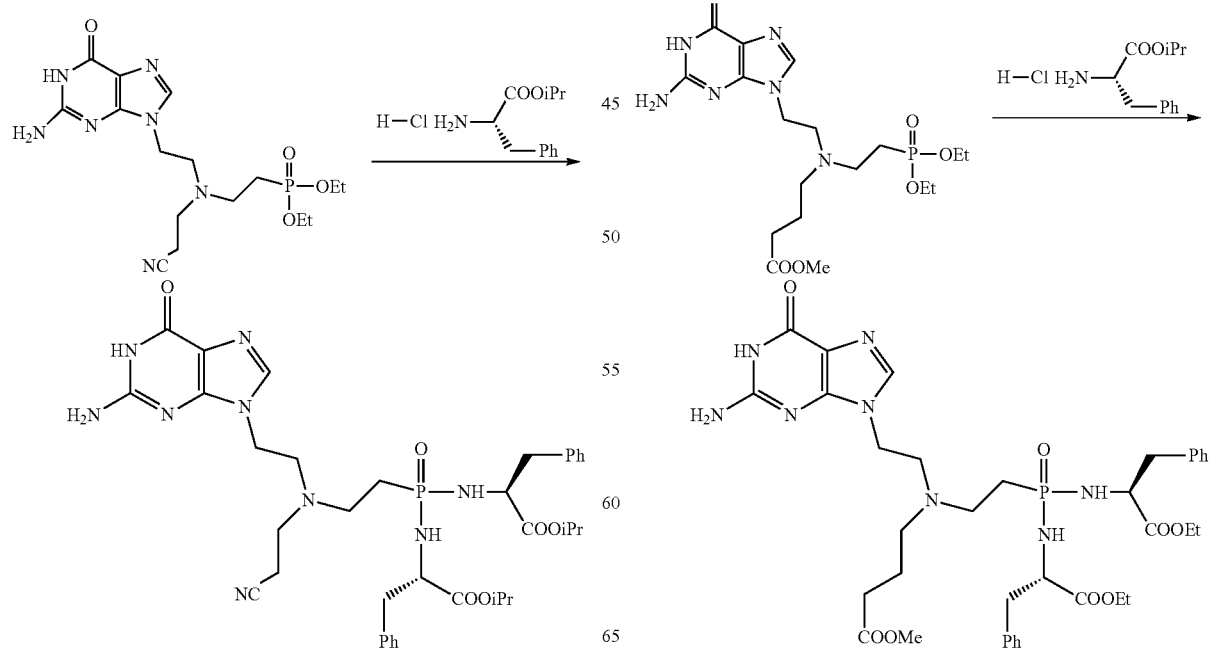

A mixture of diethyl 9-[(N-(4-Methoxy-4-oxobutyl)-N-(2-phosphonoethyl))-2-aminoethyl]guanine (intermediate in Example 3, 0.46 g, 1 mmol), acetonitrile (15 ml) and BrSiMe$_3$ (0.6 ml) an 2,6-lutidine (0.05 ml) was stirred for 2 days at room temperature under argon. After evaporation and codistillation with acetonitrile, the residue was dissolved in pyridine (10 ml) and ethyl (L)-phenylalamine hydrochloride (1.0 g, 4 mmol) and triethylamine (2 ml) were added. The mixture was heated to 60° C. under argon atmosphere and then solution of Aldrithiol (1.32 g, 6 mmol) and triphenylphosphine (1.6 g, 6 mmol) in dry pyridine (10 ml) was added. The reaction mixture was heated at 70° C. for 20 h, the solvent was evaporated and the residue was purified by column chromatography on silica gel. The phosphoramidate prodrug was obtained as foam in 40% yield (0.30 g).

$^1$H NMR (DMSO-d$_6$): 10.53 s, 1 H (NH); 7.61 s, 1 H (H-8); 7.21 m, 10 H (Ar); 6.42 s, 2 H (NH$_2$); 4.53 m, 1 H (NH); 4.20 m, 1 H (NH); 4.02 q, 4 H, J=7.1 (Et); 3.97 m and 3.87 m, 4 H (H-1' and NHCH); 3.56 s, 3 H (Me); 3.88 m, 2 H (NHCH); 2.86 m, 3 H and 2.75 in, 1 H (CH$_2$Ph); 2.54 m, 2 H (H-2'); 2.40 m, 2 H (H-5'); 2.23 m, 2 H (H-3'); 2.11 m, 2 H (H-7'); 1.44 m, 2 H (H-6'); 1.35 m, 2 H (H-4'); 1.12 t, 3 H and 1.06 t, 3 H, J=7.1 (Et). $^{13}$C NMR (DMSO-do): 173.38 and 173.36 (CO); 156.98 (C-6); 153.65 (C-2); 151.23 (C-4); 137.88 (C-8); 137.48, 137.39, 129.59, 2 C, 129.55, 2 C, 128.30, 2 C, 128.25, 2 C, 126.68 and 126.59 (Ar); 116.65 (C-5); 60.52 and 60.42 (Et); 54.27 and 54.14 (NHCH); 51.81 (C-2'); 51.38 (Me); 47.01 (C-5'); 44.10 (C-3'); 30.91 (C-7'); 24.36 d, J(P,C)=124.0 (C-4'); 22.26 (C-6'). 14.13 and 14.07 (Et). HRMS calcd. for C$_{36}$H$_{50}$N$_8$O$_8$P: 753.34837; found: 753.34843. MS (ESI): m/z=753 [M+H]$^+$.

As referred to herein this compound provides a prodrug form of a compound of the invention.

Example 19, 0.41 g, 1 mmol), acetonitrile (15 ml), dimethylformamide (3 ml) and BrSiMe$_3$ (0.6 ml) an 2,6-lutidine (0.05 ml) was stirred for 3 days at room temperature under argon. After evaporation and codistillation with toluene, the residue was dissolved in pyridine (10 ml) and ethyl (L)-phenylalamine hydrochloride (1.0 g, 4 mmol) and triethylamine (2 ml) were added. The mixture was heated to 70° C. under argon atmosphere and then solution of Aldrithiol (1.32 g, 6 mmol) and triphenylphosphine (1.6 g, 6 mmol) in dry pyridine (10 ml) was added. The reaction mixture was heated at 70° C. for 2 days, the solvent was evaporated and the residue was purified by column chromatography on silica gel. The phosphoramidate prodrug was obtained as foam in 58% yield (0.41 g). $^1$H NMR (DMSO-d$_6$): 12.30 s, 1 H (NH); 8.04 s, 1 H and 8.02 s, 1 H (H-8 and H-2); 7.21 m, 10 H (Ar); 4.52 t, 1 H, J=11.6 (NH); 4.20 t, 2 H, J=11.6 (NH); 4.11 t, 2 H, 6.2 (H-2'); 4.03 q, 4 H, J=7.1 (Et); 3.98 m, 1 H and 3.89 m, 1 H (CH); 2.86 in, 3 H and 2.75 m, 1 H (CH$_2$Ph); 2.63 t, 2 H, J(2',1')=6.2 (H-2'); 2.48 m, 1 H and 2.39 m, 1 H (H-3'); 2.30 t, 2 H, J(5',6')=6.7 (H-5'); 2.18 t, 2 H, J(7',6')=7.2 (H-7'); 1.45 m, 2 H (H-6'); 1.36 m, 2 H (H-4'); 1.12 t, 3 H and 1.07 t, 3 H, J=7.1 (Et). $^{13}$C NMR (DMSO-d$_6$): 173.04 and 172.85 (CO); 156.49 (C-6); 147.38 (C-4); 145.20 (C-2); 140.44 (C-8); 137.08, 2 C, 129.27, 2 C, 129.22, 2 C, 127.96, 2 C, 127.93, 2 C, 126.33 and 126.24 (Ar); 120.29 (C-5); 118.24 (CN); 60.20 and 60.11 (Et); 53.87 and 53.81 (NHCH); 51.88 (C-2'); 50.98 (C-5'); 46.63 (C-3'); 42.07 (C-1'); 41.18 (CH$_2$Ph); 22.56 (C-7'); 13.80 and 13.77 (Et); 13.50 (C-6'). HRMS calcd. for C$_{35}$H$_{46}$N$_8$O$_6$P: 705.32724; found: 705.32730. MS (ESI): m/z=705 [M+H]$^+$.

As referred to herein this compound provides a prodrug form of a compound of the invention.

Example 32

(2S,2'S)-diethyl-2,2'-{[2-((3-cyanopropyl)(2-(hypoxanthine-9-yl)ethyl)amino)ethyl]phosphoryl}bis(azanediyl)bis(3-phenylpropanoate)

Example 33

(2S,2'S)-diethyl-2,2'-{[2-((2-(guanine-9-yl)ethyl)(3-methoxy-3-oxopropyl)amino)ethyl]phosphoryl}bis(azanediyl)bis(3-phenylpropanoate)

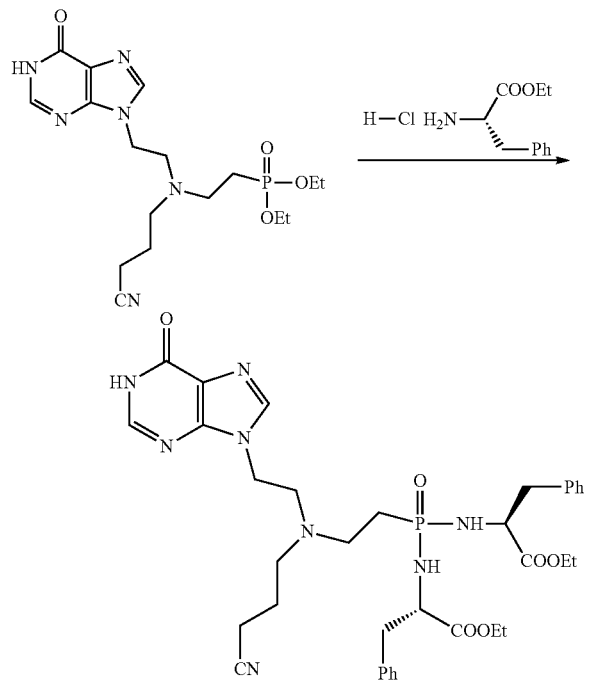

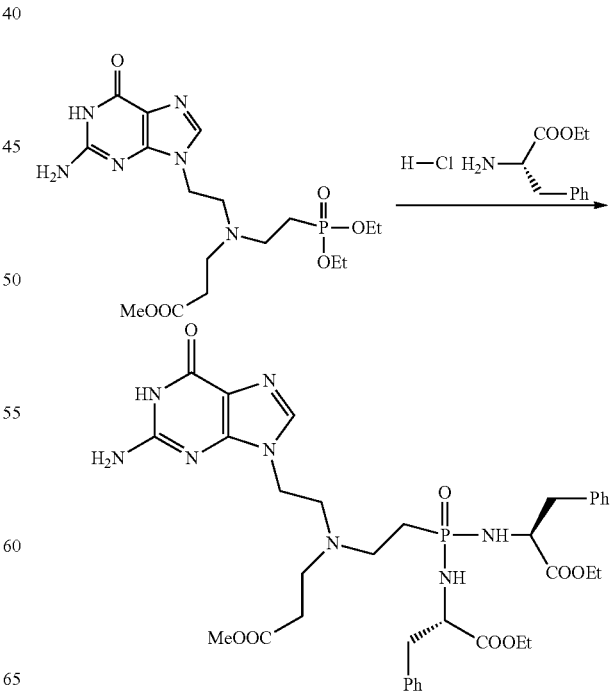

A mixture of diethyl 9-[(N-(2-cyanoethyl)-N-(2-phosphonoethyl))-2-aminoethyl]hypoxanthine (intermediate in A mixture of diethyl 9-[(N-(3-methoxy-3-oxopropyl)-N-(2-phosphonoethyl))-2-aminoethyl]guanine (intermediate in Example 2, 0.44 g, 1 mmol), acetonitrile (15 ml), dimethylformamide (3 ml), BrSiMe$_3$ (0.6 ml) and 2,6-lutidine (0.05 nil) was stirred for 3 days at room temperature under argon. After evaporation and codistillation with toluene, the residue was dissolved in pyridine (10 ml) and ethyl (L)-phenylalamine hydrochloride (1.0 g, 4 mmol) and triethylamine (2 ml) were added. The mixture was heated to 60° C. under argon atmosphere and then solution of Aldrithiol (1.32 g. 6 mmol) and triphenylphosphine (1.6 g, 6 mmol) in dry pyridine (10 ml) was added. The reaction mixture was heated at 70° C. for 2 days, the solvent was evaporated and the residue was purified by column chromatography on silica gel. The phosphoramidate prodrug was obtained as foam in 40% yield (0.30 g). $^1$H NMR (DMSO-d$_6$): 10.55 s, 1 H (NH); 7.59 s, 1 H (H-8); 7.20 m, 10 H (Ar); 6.46 s, 2 H (NH$_2$); 4.54 t, 1 H, J=11.6 (NH); 4.18 t, 1 H. J=11.8 (NH); 4.02 q, 4 H, J=7.3 (Et); 3.97 m, 1 H (NHCH); 3.87 m, 3 H (NHCH and H-1'); 3.55 s, 3 H (Me); 2.87 m, 3 H and 2.71 m, 1 H (CH$_2$Ph); 2.56 m, 2 H (H-2' and H-5'); 2.45 m, 2 H (H-3'); 2.28 t, 2 H, J(6',5')=6.9 (H-6'); 1.37 m, 2 H (H-4'); 1.11 t. 3 H and 1.06 t, 3 H (Et). $^{13}$C NMR (DMSO-d$_6$): 173.08, 172.90 and 172.24 (CO); 156.71 (C-6); 153.32 (C-2); 150.95 (C-4);. 137.60 (C-8); 137.21, 137.11, 129.29, 2 C, 129.24, 2 C, 127.99, 2 C, 127.94, 2 C, 126.36 and 126.27 (Ar); 116.29 (C-5); 60.21 and 60.11 (Et); 53.98 and 53.83 (NHCH); 51.90 (C-2'); 51.12 (Me); 47.91 (C-5'); 46.64 (C-3'); 40.53 (C-1'); 31.54 (C-6'); 13.83 and 13.77 (Et). HRMS calcd. for C$_{35}$H$_{48}$N$_8$O$_8$P: 739.33272; found: 739.33281. MS (ESI): m/z=739 [M+H]$^+$.

As referred to herein this compound provides a prodrug form of a compound of the invention.

Example 34

(2S,2'S)-Diethyl-2,2'-{[2-((3-methoxy-3-oxopropyl)(2-(hypoxanthine-9-yl)ethyl)amino)ethyl]phosphoryl}bis(azanediyl)bis(3-phenylpropanoate)

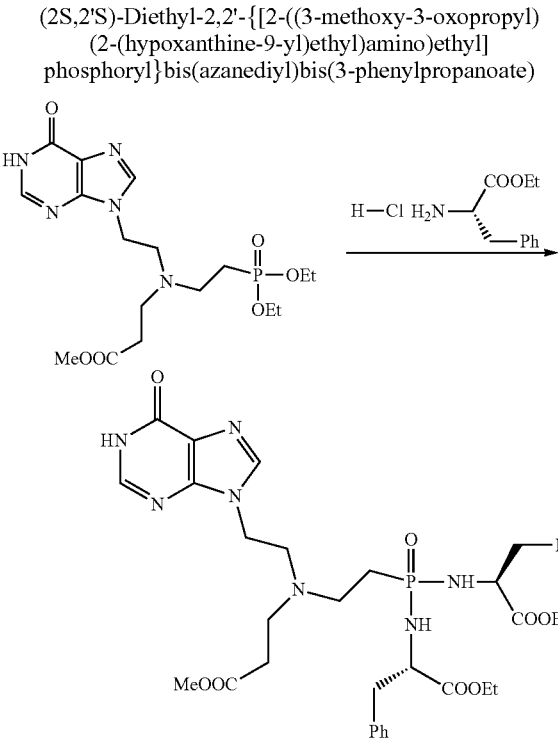

A mixture of diethyl 9-[(N-(3-methoxy-3-oxopropyl)-N-(2-phosphonoethyl))-2-aminoethyl]hypoxanthine (intermediate in Example 16, 0.43 g, 1 mmol), acetonitrile (15 ml), dimethylformamide (3 ml) and BrSiMe$_3$ (0.6 ml) an 2,6-lutidine (0.05 ml) was stirred for 3 days at room temperature under argon. After evaporation and codistillation with toluene, the residue was dissolved in pyridine (10 ml) and ethyl (L)-phenylalamine hydrochloride (1.0 g, 4 mmol) and triethylamine (2 ml) were added. The mixture was heated to 60° C. under argon atmosphere and then a solution of Aldrithiol (1.32 g, 6 mmol) and triphenylphosphine (1.6 g, 6 mmol) in dry pyridine (10 ml) was added. The reaction mixture was heated at 70° C. for 2 days, the solvent was evaporated and the residue was purified by column chromatography on silica gel. The phosphoramidate prodrug was obtained as foam in 85% yield (0.62 g). $^1$H NMR (DMSO-d$_6$): 12.26 s, 1 H (NH); 8.02 s, 1 H and 7.99 s, 1 H (H-8 and H-2); 7.20 m, 10 H (Ar); 4.51 t, 1 H, J=11.2 (NH); 4.19 t, 2 H, J=10.6 (NH); 4.09 t, 2 H, J(1',2')=6.2 (H-2'); 4.02 q, 4 H, J=7.1 (Et); 4.01 m, 1 H and 3.87 m, 1 H (CH); 3.53 s, 3 H (Me); 2.87 m, 3 H and 2.75 m, 1 H (CH$_2$Ph); 2.56 t, 2 H, J(5',6')=7.0 (H-5'); 2.62 t, 2 H, J(2',1')=6.2 (H-2'); 2.43 m, m, 2 H (H-3'); 2.24 t, 2 H, J=7.1 (H-6'); 1.33 m, 2 H (H-4'); 1.11 t, 3 H and 1.06 t, 3 H, J=7.1 (Et). $^{13}$C NMR (DMSO-d$_6$): 173.09, 172.92 and 172.16 (CO); 156.56 (C-6); 148.17 (C-4); 145.17 (C-2); 140.48 (C-8); 137.21, 137.11, 129.30, 2 C, 129.24, 2 C, 127.98, 2 C, 127.94, 2 C, 126.35 and 126.26 (Ar); 123.69 (C-5); 60.21 and 60.11 (Et); 53.94 and 53.82 (NHCH); 51.90 (C-2'); 51.08 (Me); 47.89 (C-5'); 46.76 (C-3'); 41.16 (C-1'); 31.51 (C-7'); 25.92 (C-6'); 21.52, J(P,C)=136.3 (C-4'); 13.83 and 13.78 (Et). HRMS calcd. for C$_{35}$H$_{47}$N$_7$O$_8$P: 724.32182; found: 724.32161. MS (ESI): m/z=724 [M+H]$^+$.

As referred to herein this compound provides a prodrug form of a compound of the invention.

Example 35 tetra-L-Phenylalanine prodrug of 9-[(N,N-(bis-2-phosphonoethyl))-2-aminoethyl]hypoxanthine

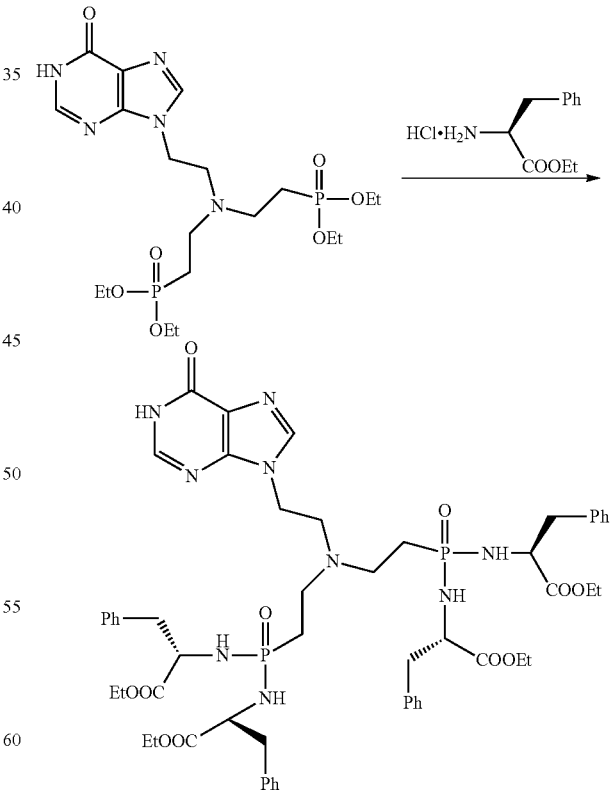

A mixture of diethyl 9-[(N,N-(bis-2-phosphonoethyl))-2-aminoethyl]hypoxanthine (intermediate in Example 25, 0.51 g, 1 mmol), acetonitrile (20 ml), dimethylformamide (2 ml) and BrSiMe$_3$ (2 ml) and 2,6-lutidine (0.1 ml) was stirred for 2 days at room temperature under argon. After evaporation and codistillation with toluene, the residue was dissolved in pyridine (15 ml) and ethyl (L)-phenylalamine hydrochloride (2.5 g, 10 mmol) and triethylamine (5 ml) were added. The mixture was heated to 70° C. under argon atmosphere and then solution of Aldrithiol (3.4 g, 15 mmol) and triphenylphosphine (4 g, 15 mmol) in dry pyridine (15 ml) was added. The reaction mixture was heated at 70° C. for 4 days, the solvent was evaporated and the residue was purified by column chromatography on silica gel and further purified by preparative HPLC. The phosphoramidate prodrug was obtained as foam in 25% yield (0.27 g). $^1$H NMR (DMSO-$d_6$): 12.28 s, 1 H. (NH); 8.00 m, 2 H (H-2 and H-8); 7.19 m, 20 H (Ar); 4.-11-4.52 m, 4 H (NH); 3.75-4.07 m, 14 H (H-1', Et, NHCH); 2.88 m, 6 H and 2.77 m, 2 H (CH$_2$Ph); 2.52 m, 2 H (H-2'); 2.39 m, 4 H (H-3', H-5'); 1.35 m, 4 H (H-4', H-6'); 1.08 m, 12 H (Et). $^{13}$C NMR (DMSO-$d_6$): 173.42, 173.33, 173.19 and 173.15 (CO); 156.84 (C-6); 148.44 (C-4); 145.51(C-2); 140.65 (C-8); 137.43, 2 C, 137.33, 2 C 129.56, 4 C, 129.52. 4 C, 128.28, 4 C, 128.26, 4 C, 126.65, 2 C and 126.62, 2 C (Ar); 123.99 (C-5); 60.51 and 60.42, 4C (Et); 54.22 m, 4 C (NHCH); 51.84 (C-2'); 46.63 and 46.58 (C-3' and C-5'); 41.19 (C-1'); 24.91 d, J(P,C)=144.03 (C-4' and C-6'); 14.11 and 14.07, 4 C (Et). HRMS calcd. for $C_{55}H_{72}N_9O_{11}P_2$: 1096.48265; found: 1096.48260. MS (ESI): m/z=1096 [M+H]$^+$.

As referred to herein this compound provides a prodrug form of a compound of the invention.

Example 36 tetra-L-Phenylalanine prodrug of 9-[(N,N-(bis-2-phosphonoethyl))-2-aminoethyl]guanine

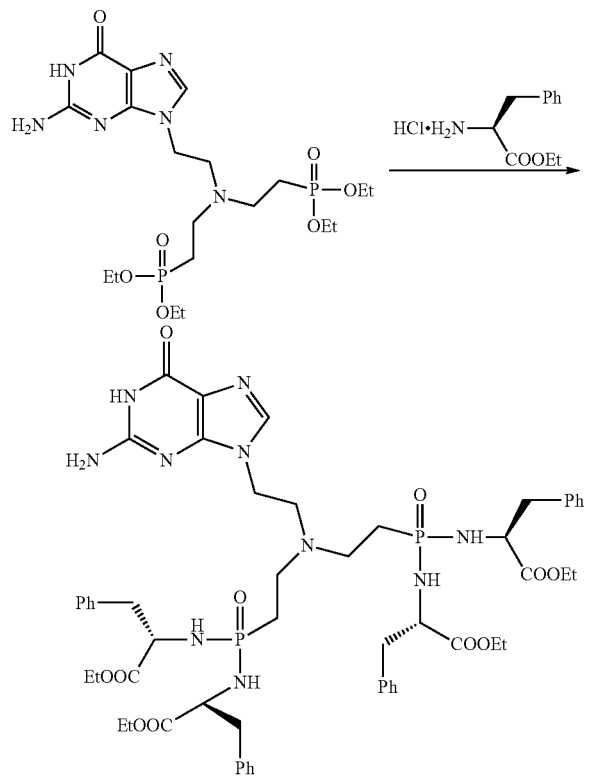

A mixture of diethyl 9-[(N,N-(bis-2-phosphonoethyl))-2-aminoethyl]guanine (intermediate in Example 11, 0.52 g, 1 mmol), acetonitrile (20 ml), dimethylformamide (1 ml) and BrSiMe$_3$ (2 ml) and 2,6-lutidine (0.1 ml) was stirred for 2 days at room temperature under argon. After evaporation and codistillation with toluene, the residue was dissolved in pyridine (15 ml) and ethyl (L)-phenylalamine hydrochloride (2.5 g, 10 mmol) and triethylamine (5 ml) were added. The mixture was heated to 60° C. under argon atmosphere and then solution of Aldrithiol (3.4 g, 15 mmol) and triphenylphosphine (4 g, 15 mmol) in dry pyridine (15 ml) was added. The reaction mixture was heated at 70° C. for 4 days, the solvent was evaporated and the residue was purified by column chromatography on silica gel and further purified by preparative HPLC. The phosphoramidate prodrug was obtained as foam in 43% yield (0.48 g). $^1$H NMR (DMSO-$d_6$): 10.56 s, 1 H (NH): 7.19 s, 1 H (H-8); 7.18 m, 20 H (Ar); 6.47 s, 2 H (NH$_2$); 4.52 t, 1 H, J=11.6 (NH); 4.21 t, 1 H, J=11.0 (NH); 3.96 m, 10 H (H-1', Et); 3.79 m, 4 H, (NHCH); 2.84 m, 6 H and 2.77 m, 2 H (CH$_2$Ph); 2.41 m, 4 H (H-3', H-5'); 1.40 m, 4 H (H-4', H-6'); 1.10 t, 6 H and 1.04 t, 6 H, J=7.2 (Et). $^{13}$C NMR (DMSO-$d_6$): 173.04, 173.02, 172.89 and 172.85 (CO); 156.72 (C-6); 153.36 (C-2); 150.97 (C-4); 137.38 (C-8); 137.12, 2 C, 137.04, 2 C 129.27, 4 C, 129.22, 4 C, 127.99, 4 C, 127.95, 4 C, 126.36, 2 C and 126.29. 2 C (Ar); 116.30 (C-5); 60.21 and 60.12, 4 C (Et); 53.98 m, 4 C (NHCH); 51.46 (C-2'); 46.26 (C-3' and C-5'); 40.00 (C-1'); 25.64 d, J(P,C)=113.61 (C-4' and C-6'); 13.80 m, 4 C (Et). HRMS calcd. for $C_{55}H_{73}N_{10}O_{11}P_2$: 1111.49300; found: 1111.49303. MS (ESI): m/z=1111.5 [M+H]$^+$.

As referred to herein this compound provides a prodrug form of a compound of the invention.

Example 37

S,S'-2,2'-((2-((2-(guanin-9-yl)ethyl)(2-cyanoethyl)amino)ethyl)phosphoryl)-bis(oxy)bis(ethane-2,1-diyl) bis(2,2-dimethylpropanethioate)

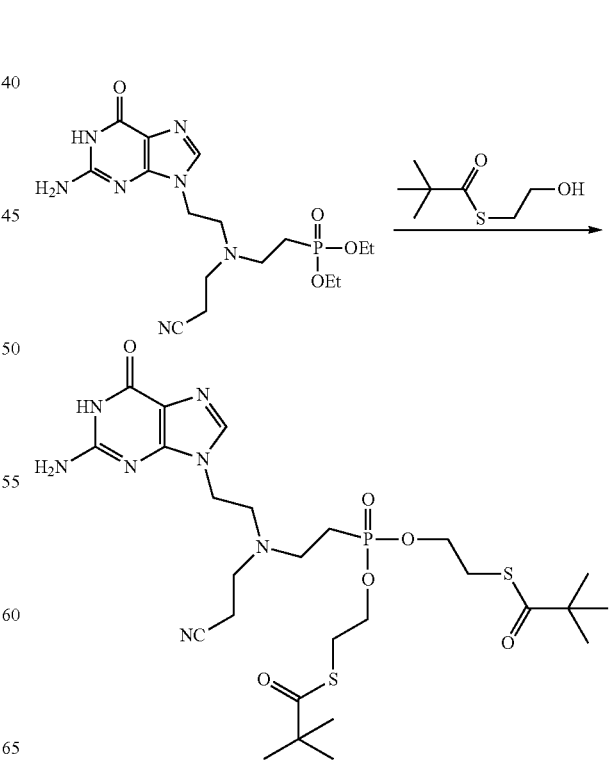

A mixture of diethyl 9-[(N-(2-cyanoethyl)-N-(2-phosphonoethyl))-2-aminoethyl]guanine (intermediate in Example 5, 0.41 g, 1 mmol), acetonitrile (10 ml), dimethylformamide (5 ml) and BrSiMe$_3$ (0.9 ml) was stirred for 3 days at room temperature under argon. After evaporation and codistillation with toluene, the residue was evaporated to dryness with mixture of triethylamine/water (1:1, 10 ml) and then codistilled with EtOH/toluene. The residue was dissolved in pyridine (10 ml) and S-2-hydroxyethyl 2,2-dimethylpropanethioate (0.81 g, 5 mmol) and 2,4,6-triisopropylbenzenesulfonylchloride (1.52 g, 5 mmol) were added.

The mixture was stirred at room temperature for 5 days, the solvent was evaporated and the residue was purified by column chromatography on silica gel and further purified by preparative HPLC. The phosphoramidate prodrug was obtained as foam in 17% yield (110 mg). $^1$H NMR (DMSO-d$_6$): 10.53 s, 1 H (NH); 7.70 s, 1 H (H-8); 6.40 s, 2 H (NH$_2$); 3.98 m, 6 H (H-1', Et); 3.09 t, 4 H, J=6.4 (CH$_2$S); 2.74 m, 6 H (H-2', H-3', H-5'); 2.54 t, 2 H, J(6',5')=6.8 (H-6'); 1.85 m, 2 H (H-4');1.17 s, 18 H (tBu). $^{13}$C NMR (DMSO-d$_6$): 205.05 (CO); 156.73 (C-6); 153.36 (C-2); 151.00 (C-4); 137.69 (C-8); 119.81 (CN); 116.35 (C-5); 63.32 and 63.28 (CH$_2$O); 51.76 (C-2'); 48.15 and 45.91 (C-3' and C-5'); 46.18, 2 C (tBu); 40.91 (C-1'); 28.45 and 28.40 (CH$_2$S); 26.81 (tBu); 22.09 d, J(P,C)=133.9 (C-4'); 15.48 (C-6'). HRMS calcd. for C$_{26}$H$_{43}$N$_7$O$_6$PS$_2$: 644.24484; found: 644.24493. MS (ESI): m/z, 644 [M+H]$^+$.

As referred to herein this compound provides a prodrug form of a compound of the invention.

Example 38

S,S'-2,2'-((2-((2-(guanin-9-yl)ethyl)(3-methoxy-3-oxopropyl)-amino)ethyl)phosphoryl)bis(oxy)bis(ethane-2,1-diyl)bis(2,2-dimethylpropanethioate)

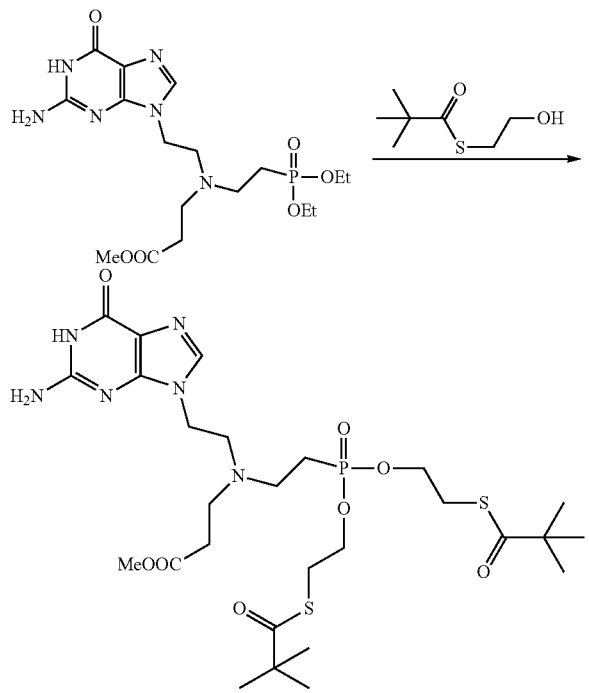

A mixture of diethyl 9-[(N-(3-methoxy-3-oxopropyl)-N-(2-phosphonoethyl))-2-aminoethyl]guanine (intermediate in Example 2, 0.44 g, 1 mmol), acetonitrile (20 ml), dimethylformamide (4 ml) and BrSiMe$_3$ (1 ml) was stirred for 3 days at room temperature under argon. After evaporation and codistillation with toluene, the residue was evaporated to dryness with mixture of triethylamine/water (1:1, 10 ml) and then codistilled with EtOH/toluene. The residue was dissolved in pyridine (10 ml) and S-2-hydroxyethyl 2,2-dimethylpropanethioate (0.81 g, 5 mmol) and 2,4,6-triisopropylbenzenesulfonylchloride (1.8 g, 6 mmol) were added.

The mixture was stirred at room temperature for 5 days, the solvent was evaporated and the residue was purified by column chromatography on silica gel and further purified by preparative HPLC. The phosphoramidate prodrug was obtained as foam in 10% yield (70 mg). $^1$H NMR (DMSO-d$_6$): 10.52 s, 1 H (NH); 7.62 s, 1 H (H-8); 6.40 s, 2 H (NH$_2$); 3.98 m, 6 H (H-1', Et); 3.54 s, 3 H (Me); 3.09 m, 4 H (CH$_2$S); 2.69 m, 6 H (H-2', H-3', H-5'); 2.32 m, 2 H (H-6'); 1.87 m, 2 H (H-4'); 1.17 s, 18 H (Me). HRMS calcd. for C$_{27}$H$_{46}$N$_6$O$_8$PS$_2$: 677.25507; found: 677.25501. MS (ESI): m/z=677 [M+H]$^+$.

As referred to herein this compound provides a prodrug form of a compound of the invention.

Assay Methodology
Determination of K$_i$ Values

The K$_i$ values were determined using a spectrophotometric assay at 25° C., 0.1 M Tris-HCl, 10 mM MgCl$_2$, pH 7.4 (Keough, D. T.; Ng, A. L.; Winzor, D. J.; Emmerson, B. T.; de Jersey, J. Purification and characterization of *Plasmodium falciparum* hypoxanthine-guanine-xanthine phosphoribosyltransferase and comparison with the human enzyme. *Mol. Biochem. Parasitol.* 1999, 98, 29-41; *Plasmodium* vivaxhypoxanthine-guanine phosphoribosyltransferase: a target for anti-malarial chemotherapy. Kerough, D. T. Hockova. D, Krecmerova, M., Naesens, L., Brereton, I. M., de Jersey, J and Guddat, L, W, *Mol. Biochem. Parasitol* (2010) 173: 165-169). The K$_i$ values are K$_{i(app)}$) as they were measured at a single concentration of the second substrate. The concentration of the second substrate (guanine) was saturating: 60 μM. K$_{i(app)}$ was calculated using the equation $$K_{m(app)} = K_m(1+[I]/K_{i(app)})$$

In Vitro Antimalarial Activity
Continuous In Vitro Cultivation of *Plasmodium falciparum* Strains:

The *P. falciparum* laboratory adapted strains utilised (D6: Sierra Leone, Africa, sensitive to chloroquine and pyrimethamine; and W2: Indochina, resistant to chloroquine and pyrimethamine) were in vitro cultured and routinely maintained in RPMI-1640-LPLF complete medium, which contained low concentrations of para-amino benzoic acid (0.0005 mg/L) and folic acid (0.01 mg/L). The low concentration of folic acid in RPMI-1640-LPLF prevents inhibition of the compound if its activity targets the parasite's folate metabolic pathway. Parasites were cultured in human red blood cells (RBCs) in vitro at 37° C. in special gas mixture (5% O$_2$, 5% CO$_2$ and 90% N$_2$) as described Trager and Jensen (1979 *Science* 193: 673-675).

Preparation of Cultivation Medium:
Base cultivation medium consisted of 10.4 g/L RPMI-1640-LPLF powder (Gibco BRL), 5.97 g/L HEPES buffer (MP Biomedicals, USA), 2.0 g/L D-glucose (BDH chemicals, Australia), 0.05 g/L hypoxanthine (Sigma, USA) and 40 mg/L gentamycin (Pfizer, Australia). The pH of the medium was adjusted to 6.9 and the solution was filtered using 0.2 μM pore size (AcroCap, Gelman Science, USA). Complete medium was prepared by adding sodium bicarbonate solution (final concentration, 0.21%) and drug-free heat inactivated human plasma obtained from the Australian Red Cross Blood Service (Brisbane) (final concentration, 10%) to the base RPMI-1640-LPLF. RPMI-1640-LPLF complete medium which lacked [3H]-hypoxanthine ([3H]-RPMI-1640-LPLF) was used during the [3H]-hypoxanthine inhibition growth assay to prevent uptake of hypoxanthine by parasites, as radioactive hypoxanthine uptake is measured as a surrogate marker of growth. All complete medium was used within three days of preparation.

Preparation of Red Blood Cells:

Red blood cells (RBC) were required for *P. falciparum* parasites to proliferate in vitro. O (Rh+) type blood was obtained from the Australian Red Cross Blood Service. The RBC were washed twice in phosphate-buffered saline (PBS) and once in [3H]-RPMI-1640-LPLF complete medium by centrifugation at 1,500×g for 5 minutes. Following the final wash, the haematocrit was measured as the percent of RBC to total culture volume. The haematocrit was adjusted to 50% by removing or adding [3H]-RPMI-LPLF complete medium.

Continuous Cultivation of Parasites:

All *P. falciparum* strains were grown in RPMI-1640-LPLF complete medium at 4% haematocrit and 1% to 8% parasitaemia at 37° C. in sealed flasks in a gas mixture of 5% $O_2$, 5% $CO_2$ and 90% $N_2$ (BOC Gases, Brisbane, Australia). For drug susceptibility assays cultures were routinely synchronised when the majority of parasites (>85%) were at early trophozoite stage. Synchronisation involved removing the more mature erythrocytic parasite stages by lysis, resulting in the retention only of early trophozoite stages. Synchronisation was performed by resuspending the infected red blood cell (iRBC) pellet in 5 to 10 times its volume of 5% D-sorbitol (Bacto Laboratories Pty. Ltd., Australia) for 5 minutes (Lambros and Vanderberg, 1979 *J Parasitol* 65: 418-420). The Mixture was centrifuged (1,500 rpm for 5 min) and the supernatant removed. The iRBC were washed twice using PBS and once using [3H]-RPMI-LPLF plain medium. Following synchronisation, a new culture was prepared with an initial parasitaemia of 1% in RPMI-LPLF complete medium.

Evaluation of In Vitro Antimalarial Activity:

The in vitro antimalarial activities of the compounds and chloroquine were assessed by exposing *P. falciparum* strains to ten serially diluted two-fold concentrations of each compound. Parasite growth was measured by uptake of tritiated [$^3$H]-hypoxanthine into newly synthesised parasitic DNA.

[3H]-Hypoxanthine growth inhibition assay:

The [3H]-hypoxanthine growth inhibition assay (Desjardins et al., 1979 *Antimicrobial Agents Chemother* 16: 710-718) was used to evaluate the in vitro antimalarial activity of the compounds. Briefly, synchronised parasite cultures (>90% rings, 6 to 8 h post invasion) in [3H]-RPMI-LPLF complete medium with 1% parasitaemia and 2% haematocrit were exposed to the compounds at ten two-fold concentrations. Chloroquine was used as a reference drug. Uninfected RBCs at 2% haematocrit were used as background controls. Two drug exposure periods were evaluated (48 h and 96 h). For the 48 h exposure period, the plates were incubated in the gas mixture at 37° C. for approximately 20 h (about 24 h post-invasion). To each well, 0.2 µCi of tritiated hypoxanthine (GE Healthcare, Amersham) solution in [3H] RPMI-1640-LPLF was added. The plates were incubated for a further 24 h at 37° C. in the gas Mixture and then frozen at −20° C. For the 96 h exposure period, the plates were incubated in the gas mixture at 37° C. for approximately 48 h, followed by the addition of 0.2 µCi of tritiated hypoxanthine to each well and a further 48 h of incubation and then frozen at −20° C. Plates were thawed and harvested using Tomtech, Harvester 96 Mach III and radioactive counts were obtained using Wallac TriLux 1450 Microbeta Liquid Scintillation Counter (Perkin Elmer, USA). All assays were performed in triplicate for each strain and at least on two separate occasions.

In Vitro Inhibition Concentrations:

Tritiated hypoxanthine uptake data were analysed in Graphpad Prism V5.0 software (GraphPad Software Inc. USA). The concentrations of the compounds, and chloroquine were transformed into logarithmic values. After subtracting the background values, the data from drug-treated wells were normalised against drug-free control wells. Non-linear regression analysis was carried out of the compound's concentration versus parasitic hypoxanthine incorporation. The in vitro antimalarial activity the compound is defined as inhibitory concentrations ($IC_{50}$) and ($IC_{90}$) that cause 50% and 90% inhibition of parasite growth as determined by measuring [$^3$H]-hypoxanthine incorporation.

Comparative Example

The substitution of the oxygen atom present in acyclic portion of the known PEE compounds by —NH resulted in an increase in the $K_i$ values for human HGPRT and PfHGPRT (Table 1).

TABLE 1

Comparison of the $K_i$ values of the PEE compounds with aza-ANP

| Compound | B = Guanine $K_i$ (µM) | | | B = Hypoxanthine $K_i$ (µM) | | |
|---|---|---|---|---|---|---|
| | human | Pf | Pv | human | Pf | Pv |
| 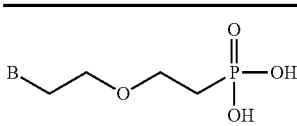 | 1 ± 0.5 | 0.1 ± 0.02 | ND$^a$ | 3.6 ± 0.2 | 0.3 ± 0.04 | ND$^a$ |
| 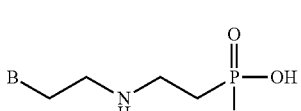 | 3 ± 0.6 | 16 ± 1 | 11 ± 0.6 | 40 ± 2 | ≥200 | ≥250 |

$^a$ND = not determined

These aza-ANPs are also weak inhibitors for PvHGPRT. The $K_i$ for the guanine derivative is 11 μM and, similar to that found for PfHGXPRT, for the hypoxanthine derivative the $K_i$ is ≥200 μM. Without wishing to be bound by theory, the substitution of the partially negatively charged oxygen atom by the positively charged nitrogen may change the conformation of the linker resulting in different interactions between the ligand and the active site amino acid residues.

It was thus unexpected that when the nitrogen atom of the aza-ANPs was substituted with a second tail that the binding affinity improved. In particular there was a decrease in the $K_i$ values as shown in Table 2 when a second phosphonate group was attached by an ethylene linker to the nitrogen atom as shown:

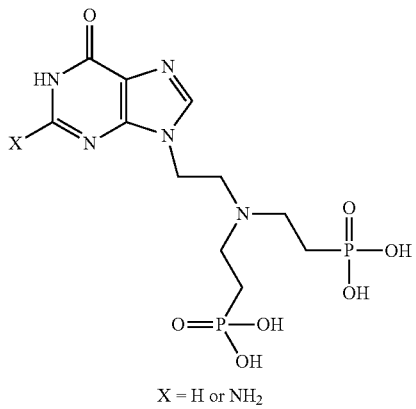

X = H or NH₂

TABLE 2

The decrease in the $K_i$ value when the proton attached to the nitrogen atom in the linker is replaced by a phosphonate group

| Enzyme | $K_i$ ratio (proto:phosphonatoethyl) Guanine as the base | $K_i$ ratio (proto:phosphonatoethyl) Hypoxanthine as the base |
|---|---|---|
| Human HGPRT | 15-fold | 13-fold |
| PfHGXPRT | 53-fold | >500-fold |
| PvHGPRT | 12-fold | >20-fold |

The inhibition constants for a range of further compounds bearing a tertiary amine tail are shown in Table 3.

These results suggest that the guanine-based ANPs are more active than the hypoxanthine-based ANP against human. HGPRT and PvHGPRT and that PfHGXPRT does not exhibit such base discrimination. A number of the compounds display significantly better inhibition of parasicidal enzyme HG(X)PRT over human HGPRT, particularly those with a ethylenecarbomethoxy or ethylenecarboxy side chain.

TABLE 3

$K_i$ values of N-branched ANPs for the human HGPRT, PfHGXPRT and PvHGPRT

| Substituent R | B = Guanine $K_i$ (μM) human | Pf | Pv | B = Hypoxanthine $K_i$ (μM) human | Pf | Pv |
|---|---|---|---|---|---|---|
| ⋯COOEt | 0.1 ± 0.02 | 1.7 ± 0.3 | 1.5 ± 0.4 | 2.6 ± 0.5 | 1.9 ± 0.4 | 11 ± 1 |
| ⋯COOMe | 0.5 ± 0.1 | 0.1 ± 0.02 | 4 ± 0.5 | ≥200 | 0.1 ± 0.03 | 21 ± 2 |
| ⋯COOMe | 0.1 ± 0.02 | 1.3 ± 0.1 | ≥200 | 22 ± 3 | ≥220 | ≥250 |
| ⋯CN | ND$^a$ | ND$^a$ | ND$^a$ | 35± | ≥250 | 47 ± 5 |
| ⋯CN | 0.07 ± 0.02 | 0.2 ± 0.03 | 0.3 ± 0.03 | 2.4 ± 0.2 | 0.2 ± 0.05 | 0.7 ± 0.06 |

TABLE 3-continued $K_i$ values of N-branched ANPs for the human HGPRT, PfHGXPRT and PvHGPRT

|  | B = Guanine $K_i$ (μM) | | | B = Hypoxanthine $K_i$ (μM) | | |
|---|---|---|---|---|---|---|
| Substituent R | human | Pf | Pv | human | Pf | Pv |
| ⁓CN (butyronitrile) | 0.6 ± 0.1 | 4 ± 0.05 | 8 ± 1 | 29 ± 2 | 6 ± 0.06 | ≥230 |
| ⁓COOH (acetic acid) | 1.4 ± 0.2 | 0.7 ± 0.1 | 28 ± 1 | 32 ± 2 | 0.6 ± 0.06 | 178 ± 10 |
| ⁓COOH (propionic acid) | 0.15 ± 0.04 | 0.2 ± 0.03 | 0.05 ± 0.004 | ≥240 | 0.4 ± 0.03 | 41 ± 5 |
| ⁓COOH (butyric acid) | 0.1 ± 0.02 | 0.1 ± 0.01 | 25 ± 4 | 5.4 ± 0.2 | ≥210 | 1.6 ± 0.2 |
| ⁓OH | 0.07 ± 0.005 | 0.2 ± 0.04 | 1.4 ± 0.1 | 5.5 ± 0.4 | 2.6 ± 0.4 | 21 ± 3 |
| ⁓P(O)(OH)₂ | 0.2 ± 0.006 | 0.3 ± 0.05 | 0.9 ± 0.1 | 3.0 ± 0.6 | 0.4 ± 0.1 | 13 ± 3 |

$^a$ND, not determined.

A number of compounds displayed significant decreases in $IC_{50}$ when the phosphonate group was masked, such as in the form of a prodrug. As shown in Table 5, derivatisation of two cyano compounds into the corresponding isopropoxy phenylalanine phosphoramidate prodrugs led to a significant increase in activity in a cell-based assay. Two of these compounds have been tested as inhibitors of *E. coli* XGPRT (Table 4).

TABLE 4

$K_i$ values for two ANPs with *E. coli* XGPRT

| Compound | $K_i$ (μM) XGPRT |
|---|---|
| 1 | 0.4 |
| 2 | 27 |

TABLE 4-continued $K_i$ values for two ANPs with *E. coli* XGPRT

| Compound | $K_i$ (μM) XGPRT |
|---|---|

1

TABLE 4-continued

K$_i$ values for two ANPs with E. coli XGPRT

| Compound | K$_i$ (µM) XGPRT |
|---|---|

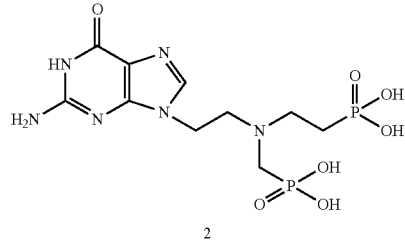 [SMILES: Nc1nc2c(ncn2CCN(CCP(=O)(O)O)CP(=O)(O)O)c(=O)[nH]1]

2

TABLE 5(a)

Cell culture data for compounds of the invention and prodrug forms thereof

| Compound | IC$_{50}$ | D6 IC$_{90}$ | IC$_{50}$ µM | W2 IC$_{90}$ |
|---|---|---|---|---|
| 3 | ND | ND | ND | ND |
| 4 | 8.6 ± 1.5 | 24.5 ± 3.5 | 5.7 ± 3.9 | 32.5 ± 3.5 |
| 5 | ND | ND | ND | ND |
| 6 | 4.2 ± 1.4 | 10.6 ± 1.8 | 5.5 ± 1.6 | 16.1 ± 0.1 |

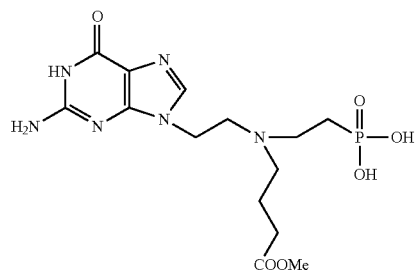

Compound 3
K$_i$ (µM): 0.1 (Hu); 1.3 (Pf); ≥200 (Pv)

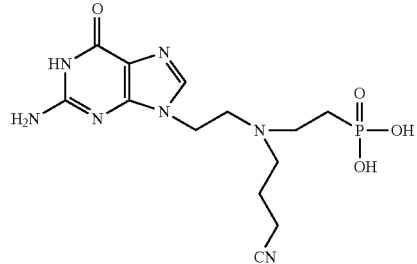

Compound 5
0.6 (Hu); 4 (Pf); 8 (Pv)

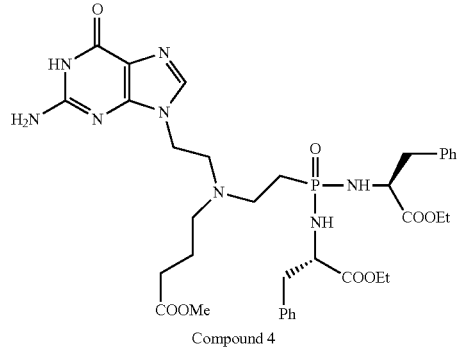 [SMILES: CCOC(=O)[C@H](Cc1ccccc1)NP(=O)(CCN(CCCC(=O)OC)CCn1cnc2c(=O)[nH]c(N)nc21)N[C@@H](Cc1ccccc1)C(=O)OCC]

Compound 4

TABLE 5(a)-continued

Cell culture data for compounds of the invention and prodrug forms thereof

| Compound | IC$_{50}$ | D6 IC$_{90}$ | IC$_{50}$ µM | W2 IC$_{90}$ |
|---|---|---|---|---|

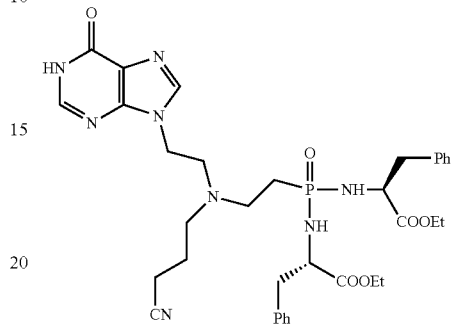

Compound 6

TABLE 5(b)

Cell culture data for compounds of the invention and prodrug forms thereof

| Compound | IC$_{50}$ | D6 IC$_{90}$ | IC$_{50}$ µM | W2 IC$_{90}$ |
|---|---|---|---|---|
| 7 | ND | ND | ND | ND |
| 8 | 3.5 ± 1.0 | 8.6 ± 1.4 | 2.9 ± 1.1 | 15.9 ± 4.5 |
| 9 | ND | ND | ND | ND |
| 10 | 11.8 ± 1.6 | 30 ± 2.9 | 5.6 ± 1.8 | 37.5 ± 3.5 |

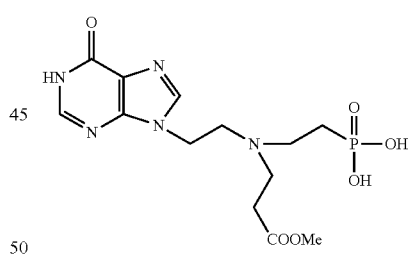

Compound 7
K$_i$ (µM): ≥200 (Hu); 0.1 (Pf); 21 (Pv)

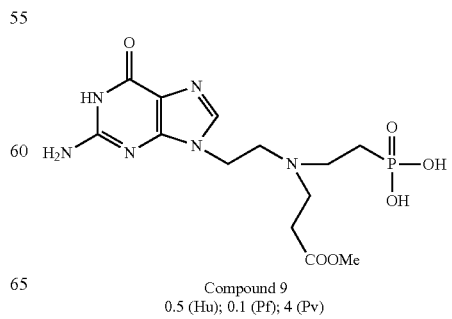

Compound 9
0.5 (Hu); 0.1 (Pf); 4 (Pv)

TABLE 5(b)-continued

Cell culture data for compounds of the invention and prodrug forms thereof

| Compound | IC$_{50}$ | D6 IC$_{90}$ | IC$_{50}$ µM | W2 IC$_{90}$ |
|---|---|---|---|---|

Compound 8

Compound 10

TABLE 5(c)

Cell culture data for compounds of the invention and prodrug forms thereof

| Compound | IC$_{50}$ | D6 IC$_{90}$ | IC$_{50}$ µM | W2 IC$_{90}$ |
|---|---|---|---|---|
| 11 | ~145 | NA | NA | NA |
| 12 | 6.4 ± 0.9 | 10.2 ± 1.6 | 10.4 ± 2.0 | 21.2 ± 1.0 |
| 13 | 75 | 215 | NA | NA |
| 14 | 12.3 ± 1.6 | 18.7 ± 1.7 | 19.3 ± 7.5 | 48.0 ± 13.6 |

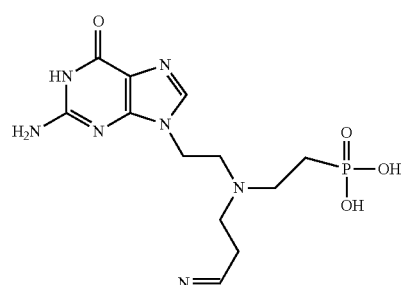

Compound 11
K$_i$ (µM): 0.07 (Hu); 0.2 (Pf); 0.3 (Pv)

TABLE 5(c)-continued

Cell culture data for compounds of the invention and prodrug forms thereof

| Compound | IC$_{50}$ | D6 IC$_{90}$ | IC$_{50}$ µM | W2 IC$_{90}$ |
|---|---|---|---|---|

Compound 13
2.4 (Hu); 0.3 (Pf); 0.7 (Pv)

Compound 12

Compound 14

ND = not tested in the cell based assay
Na = No inhibition of growth detected in the assay Inhibition of *Mycobacterium tuberculosis*

In a further study, *M. tuberculosis* H37Ra (ATCC 25177) was grown in Middlebrook 7H9 broth medium supplemented with OADC, 0.5% glycerol and 0.05% Tween-80. Freshly seeded cultures were grown at 37° C., for approximately 14 days, to mid-exponential phase (OD600 0.4-0.8) for use in inhibition assays. The potency of the inhibitors was measured by a resazurin reduction microplate assay, with some alterations. *M. tuberculosis*, grown to mid-exponential phase (OD600 0.4-0.8), was diluted to OD600 0.001 in 7H19S media (Middlebrook 7H9 with OADC, 0.5% glycerol, 0.75% tween-80, 1% tryptone) containing 0.5% DMSO. 96-well microtitre plates were setup with 100 µL of inhibitors, serially diluted into 7H9S media. 100 µL of diluted *M. tuberculosis*, representing ~2×10$^4$ CFU/mL was added to each well. Plates were incubated for five days at 37° C. in a humidified incubator prior to the addition of 30 µL of a 0.02% resazurin solution and 12.5 µL of 20% Tween 80 to each well. Sample fluorescence was measured 30 h later on a CytoFluor multi-well plate reader (PerSeptive Biosciences) with an excitation wavelength of 530 nm and emission read at 580 nm. Changes in fluorescence relative to positive control wells (H37Ra with no inhibitor) minus negative control wells (no H37Ra) were plotted for determination of $IC_{50}$.

According to this protocol, the following compound displayed an $IC_{50}$ value of 60 μM:

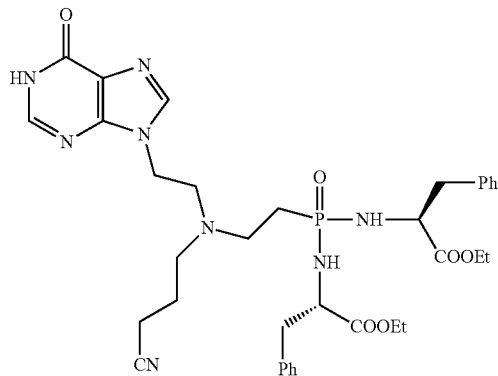 [SMILES: CCOC(=O)[C@H](Cc1ccccc1)NP(=O)(CCN(CCCC#N)CCn1cnc2c(=O)[nH]cnc21)N[C@@H](Cc1ccccc1)C(=O)OCC]

The invention claimed is:
1. A compound of formula:

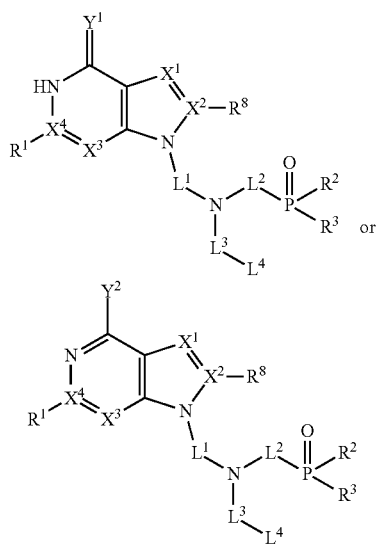

wherein:
- $L^1$ and $L^2$ are each independently selected from $C_{1-4}$alkylene, $C_{2-4}$alkenylene and $C_{2-4}$alkynylene wherein each $C_{1-4}$alkylene, $C_{2-4}$alkenylene or $C_{3-4}$alkynylene $L^1$ and/or $L^2$ is independently optionally substituted with one or more $C_{1-4}$alkyl, $C_{2-4}$alkenyl or $C_{2-4}$alkynyl;
- $L^3$ is selected from $C_{1-7}$alkylene, $C_{2-7}$alkynylene and $C_{2-7}$alkynylene wherein each $C_{1-4}$alkylene $C_{2-4}$alkenylene or $C_{3-4}$alkynylene $L^3$ is optionally substituted with one or more groups selected from OH, $C_{1-4}$alkyl, $C_{2-4}$alkenyl or $C_{2-4}$alkynyl;
- $R^1$ is alkyl, aryl, heteroaryl, alkenyl, alkynyl, arylalkyl, heteroarylalkyl, $NR^7_2$, halogen, $OR^7$, H or $NH_2$;
- $R^2$ and $R^3$ are independently selected from OH, $OR^7$, $SR^7$, $NHR^7$, $NR^7_2$, and $R^p$;
- $R^4$ is $NH_2$, NHOH, $N_3$, $NHR^7$, $NR^7_2$, $C(O)NHR^7$, $C(O)NR^7_2$, SH, $SR^7$, CHO, alkyl, alkenyl, alkynyl, aryl, heteroaryl, cycloalkyl, heterocycloalkyl wherein $R^4$ is optionally substituted with one or more OH, $CH_2OH$, $C(O)R^7$, $OR^7$, $COOR^7$, CN, COOH, OH, and/or $P(O)R^5R^6$ or $R^4$ is —O—$C_{1-2}$alkylene-$P(O)R^5R^6$;
- $R^5$ and $R^6$ are independently selected from OH, $OR^7$, $SR^7$, $NHR^7$, $NR^7_2$, and $R^p$;
- $R^8$ is selected from H, alkyl, aryl, heteroaryl, $NR^7_2$, halogen, $OR^7$;
- wherein $R^p$ is selected from an amino acid residue, an optionally substituted alkoxy group and $RCOSCH_2CH_2O$— (SATE), wherein R is $C_{1-4}$alkyl and
- wherein the or each $R^7$, where present, is independently selected from alkyl, alkenyl, alkynyl, aryl, acyl and arylalkyl, $R^7$ optionally containing one or more heteroatoms;
- $X^1$ is N;
- $X^2$ is C;
- $X^3$ is N;
- $X^4$ is C;
- $Y^1$ where present is selected from S and O, and $Y^2$ where present is selected from halogen;
- wherein the combined number of carbon atoms in $L^1$ and $L^2$ excluding the number of carbon atoms in the optional substituent(s), where present, is between 3 and 5; and
- wherein the combined number of non-hydrogen atoms in $L^3$ and $R^4$ excluding the number of atoms in the optional substituent(s), where present, and excluding the number of atoms in $R^5$ and $R^6$ is less than or equal to 8, or a pharmaceutically acceptable salt thereof.

2. A compound according to claim 1 of formula:

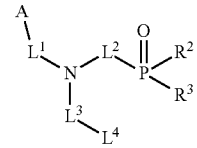

wherein A is:

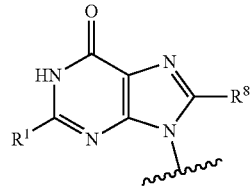

and wherein:
- $L^1$ and $L^2$ are each independently selected from $C_{1-4}$alkylene, $C_{2-4}$alkenylene and $C_{2-4}$alkynylene wherein each $C_{1-4}$alkylene, $C_{2-4}$alkenylene or $C_{3-4}$alkynylene $L^1$ and/or $L^2$ is independently optionally substituted with one or more $C_{1-4}$alkyl;
- $L^3$ is selected from $C_{1-7}$alkylene, $C_{2-7}$alkenylene and $C_{2-7}$alkynylene wherein each $C_{1-4}$alkylene, $C_{2-4}$alkenylene or $C_{3-4}$alkynylene $L^3$ is optionally substituted with one or more groups selected from OH and $C_{1-4}$alkyl;
- $R^1$ where present is alkyl, aryl, heteroaryl, alkenyl, alkynyl, arylalkyl, heteroarylalkyl, $NR^7_2$, halogen, $OR^7$, H or $NH_2$;
- $R^2$ and $R^3$ are independently selected from OH, $OR^7$, $SR^7$, $NHR^7$, $NR^7_2$, and $R^p$;

$R^4$ is $NH_2$, NHOH, $N_3$, $NHR^7$, $NR^7_2$, $C(O)NHR^7$, $C(O)NR^7_2$, SH, $SR^7$, CHO, alkyl, alkenyl, alkynyl, aryl, heteroaryl, cycloalkyl, heterocycloalkyl wherein $R^4$ is optionally substituted with one or more OH $CH_2OH$, $C(O)R^7$, $OR^7$, $COOR^7$, CN, COOH, OH, and/or $P(O)R^5R^6$ or $R^4$ is —O—$C_{1-2}$alkylene-$P(O)R^5R^6$;

$R^5$ and $R^6$ are independently selected from OH, $OR^7$, $SR^7$, $NHR^7$, $NR^7_2$, and $R^p$;

$R^8$ is selected from H, alkyl, aryl, heteroaryl, $NR^7_2$, halogen, $OR^7$;

wherein $R^p$ is selected from an amino acid residue, an optionally substituted alkoxy group and $RCOSCH_2CH_2O$— (SATE), wherein R is $C_{1-4}$alkyl and wherein the or each $R^7$, where present, is independently selected from alkyl, alkenyl, alkynyl, aryl, acyl and arylalkyl optionally containing one or more heteroatoms;

wherein the combined number of carbon atoms in $L^1$ and $L^2$ excluding the number of carbon atoms in the optional substituent(s), where present, is between 3 and 5; and wherein the combined number of non-hydrogen atoms in $L^3$ and $R^4$ excluding the number of atoms in the optional substituent(s), where present, and excluding the number of atoms in $R^5$ and $R^6$ is less than or equal to 8, or a pharmaceutically acceptable salt thereof.

3. A compound according to claim 1 of formula:

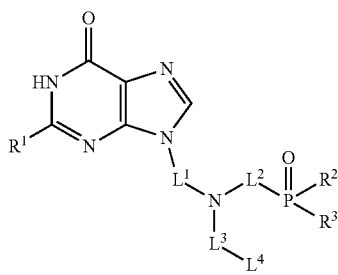

wherein:
$L^1$ and $L^2$ are each independently selected from $C_{1-4}$alkylene optionally substituted with one or more $C_{1-4}$alkyl;
$L^3$ is selected from $C_{1-7}$alkylene optionally substituted with one or more groups selected from OH and $C_{1-4}$alkyl;
$R^1$ is H or $NH_2$;
$R^2$ and $R^3$ are independently selected from OH, $OR^7$, $SR^7$, $NHR^7$, $NR^7_2$, and $R^p$;
$R^4$ is $NH_2$, NHOH, $N_3$, $NHR^7$, $NR^7_2$, $C(O)NHR^7$, $C(O)NR^7_2$, SH, $SR^7$, CHO, alkyl, alkenyl, alkynyl, aryl, heteroaryl, cycloalkyl, heterocycloalkyl optionally substituted with one or more OH and/or $CH_2OH$, $C(O)R^7$, $OR^7$, $COOR^7$, CN, COOH, OH, $P(O)R^5R^6$ or —O—$C_{1-2}$alkylene-$P(O)R^5R^6$;

$R^5$ and $R^6$ are independently selected from OH, $OR^7$, $SR^7$, $NHR^7$, $NR^7_2$, and $R^p$, wherein $R^p$ is selected from an amino acid residue, an optionally substituted alkoxy group and $RCOSCH_2CH_2O$— (SATE) wherein R is $C_{1-4}$alkyl and wherein the or each $R^7$, where present, is independently selected from alkyl, alkenyl, alkynyl, aryl, acyl and arylalkyl optionally containing one or more heteroatoms;

wherein the combined number of carbon atoms in $L^1$ and $L^2$ excluding the number of carbon atoms in the optional substituent(s), where present, is between 3 and 5; and wherein the combined number of non-hydrogen atoms in $L^3$ and $R^4$ excluding $R^5$ and $R^6$ is less than or equal to 8, or a pharmaceutically acceptable salt thereof.

4. The compound according to claim 1 wherein the combined number of carbon atoms in $L^1$ and $L^2$ excluding the number of carbon atoms in the optional substituent(s), where present, is 4.

5. The compound according to claim 1 wherein $L^1$ and/or $L^2$ are ethylene.

6. The compound according to claim 1 wherein $R^2$, $R^3$, $R^5$ and $R^6$ are independently selected from OH, $OR^7$ and $R^p$.

7. The compound according to claim 1 wherein $R^7$ is $C_{1-3}$alkyl.

8. The compound according to claim 1 wherein $R^p$ is selected from an amino acid residue and an optionally substituted alkoxy group.

9. The compound according to claim 8 wherein $R^p$ is $RCOSCH_2CH_2O$— (SATE), wherein R is $C_{1-4}$alkyl.

10. A compound according to claim 2, or a pharmaceutically acceptable salt thereof, for use in the treatment of malaria, tuberculosis or a uropathogenic *Escherichia coli* infection.

11. A pharmaceutical composition comprising a therapeutically effective amount of a compound according to claim 2, or a pharmaceutically acceptable salt thereof, together with at least one pharmaceutically acceptable carrier or diluent.

12. A combination comprising a therapeutically effective amount of a compound according to claim 2, or a pharmaceutically acceptable salt thereof, together with at least one other therapeutic agent.

13. A method of treating malaria, tuberculosis or a uropathogenic *Escherichia coli* infection comprising administering a therapeutically effective amount of a compound according to claim 2, or a pharmaceutically acceptable salt thereof, to a subject in need thereof.

14. The method according to claim 13 wherein the microbial infection is caused by one or more of *Plasmodium falciparum*, *Plasmodium vivax*, *Mycobacterium tuberculosis*, or a uropathogenic *Escherichia coli*.

* * * * *